(12) United States Patent
Alsop et al.

(10) Patent No.: US 10,421,808 B2
(45) Date of Patent: Sep. 24, 2019

(54) BAK BINDING PROTEINS

(71) Applicant: THE WALTER AND ELIZA HALL INSTITUTE OF MEDICAL RESEARCH WEHI, Parkville, Victoria (AU)

(72) Inventors: Amber Alsop, Parkville (AU); Khatira Anwari, Parkville (AU); Grant Dewson, Parkville (AU); Sweta Iyer, Parkville (AU); Ruth Kluck, Parkville (AU)

(73) Assignee: The Walter and Eliza Hall Institute of Medical Research, Melbourne, Victoria (AU)

( * ) Notice: Subject to any disclaimer, the term of this patent is extended or adjusted under 35 U.S.C. 154(b) by 62 days.

(21) Appl. No.: 15/313,761

(22) PCT Filed: May 20, 2015

(86) PCT No.: PCT/AU2015/000290
§ 371 (c)(1),
(2) Date: Nov. 23, 2016

(87) PCT Pub. No.: WO2015/176104
PCT Pub. Date: Nov. 26, 2015

(65) Prior Publication Data
US 2017/0334988 A1 Nov. 23, 2017

Related U.S. Application Data

(60) Provisional application No. 62/002,212, filed on May 23, 2014.

(30) Foreign Application Priority Data

May 23, 2014 (AU) ................................ 2014202830

(51) Int. Cl.
| | |
|---|---|
| *C07K 16/18* | (2006.01) |
| *C07K 14/705* | (2006.01) |
| *C07K 16/28* | (2006.01) |
| *A61K 47/68* | (2017.01) |
| *G01N 33/574* | (2006.01) |
| *G01N 33/68* | (2006.01) |
| *A61K 39/395* | (2006.01) |

(52) U.S. Cl.
CPC .......... *C07K 16/28* (2013.01); *A61K 47/6849* (2017.08); *C07K 16/18* (2013.01); *G01N 33/57492* (2013.01); *G01N 33/6854* (2013.01); *G01N 33/6872* (2013.01); *A61K 39/3955* (2013.01); *C07K 2317/34* (2013.01); *C07K 2317/52* (2013.01); *C07K 2317/524* (2013.01); *C07K 2317/526* (2013.01); *C07K 2317/54* (2013.01); *C07K 2317/55* (2013.01); *C07K 2317/56* (2013.01); *C07K 2317/565* (2013.01); *C07K 2317/622* (2013.01); *C07K 2317/626* (2013.01); *C07K 2317/73* (2013.01); *C07K 2317/75* (2013.01); *C07K 2317/92* (2013.01); *G01N 2333/705* (2013.01); *G01N 2500/02* (2013.01); *G01N 2500/20* (2013.01)

(58) Field of Classification Search
CPC .......... A61K 2039/505; A61K 39/3955; A61K 39/39558; C07K 2317/92; C07K 2317/56; C07K 2317/565; C07K 2317/622; C07K 2317/75; C07K 16/18; C07K 16/22; C07K 16/30; C07K 2317/73; C07K 2317/569

See application file for complete search history.

(56) References Cited

U.S. PATENT DOCUMENTS

| | | | | |
|---|---|---|---|---|
| 2004/0171809 A1* | 9/2004 | Korsmeyer | ........ | C07K 14/4747 530/350 |
| 2006/0198832 A1* | 9/2006 | Satterthwait | ....... | C07K 14/4702 424/94.2 |

FOREIGN PATENT DOCUMENTS

WO WO-2003062828 A2 * 7/2003

OTHER PUBLICATIONS

Pang et al. Bak conformational changes induced by ligand binding: insight into BH3 domain binding and Bak homo-oligomerization. Scientific Reports 2: 257, 2012 (9 total pages).*
Brorson et al. Mutational analysis of avidity and fine specificity of anti-levan antibodies. J Immunol 163: 6694-6701, 1999.*
Brummell et al. Probing the combining site of an anti-carbohydrate antibody by saturation-mutagenesis: role of the heavy-chain CDR3 residues. Biochem 32(4): 1180-1187, 1993 (abstract).*
Burks et al. In vitro scanning saturation mutagenesis of an antibody binding pocket. Proc Natl Acad Sci USA 94: 412-417, 1997.*
Cassett et al. A peptide mimetic of an anti-CD4 monoclonal antibody by rationale design. Biochem Biophys Res Comm 307: 198-205, 2003.*
Chen et al. J Mol Biol 293: 865-881, 1999.*
Colman (Research in Immunol. 145:33-36, 1994.*
De Pascalis et al. Grafting and "abbreviated" complementarity-determining regions containing specificity-determining residues essential for ligand contact to engineer a less immunogenic humanized monoclonal antibody. J Immunol 169: 3076-3084, 2002.*
Griffiths et al. Cell damage-induced conformational changes of the pro-apoptotic protein Bak in vivo precede the onset of apoptosis. J Cell Biol 44(5): 903-914, 1999.*
Holm et al. Functional mapping and single chain construction of the anti-cytokeratin 8 monoclonal antibody TS1. Mol Immunol 44: 1075-1084, 2007.*
Jang et al. The structural basis for DNA binding by an anti-DNA autobody. Mol Immunol 35: 1207-1217, 1998.*

(Continued)

*Primary Examiner* — Bridget E Bunner
(74) *Attorney, Agent, or Firm* — Hoffmann & Baron, LLP

(57) ABSTRACT

The present disclosure provides Bak binding proteins that change the conformation of Bak and uses thereof.

18 Claims, 13 Drawing Sheets
(6 of 13 Drawing Sheet(s) Filed in Color)
Specification includes a Sequence Listing.

(56) References Cited

OTHER PUBLICATIONS

Kobayashi et al. Tryptophan H33 plays an important role in pyrimidine (6-4) pyrimidone photoproduct binding by a high-affinity antibody. Protein Engineering 12(10): 879-884, 1999.*
Letai et al. Distinct BH3 domains either sensitize or activate mitochondrial apoptosis, serving as prototype cancer therapeutics. Cancer Cell 2: 183-192, 2002.*
Lloyd et al. Modelling the human immune response: performance of a 10×11 human antibody repertoire against a broad panel of therapeutically relevant antigens. Protein Engineer Design Selection 22(3): 159-168, 2009.*
MacCallum et al. Antibody-antigen interactions: contact analysis and binding site topography. J Mol Biol 262: 732-745, 1996.*
Paul, William E., Fundamental Immunology, 3rd Edition, Raven Press, New York, Chapt. 8, pp. 292-295 (1993).*
Ren et al. BID, BIM, and PUMA are essential for activation of the Bax-and BAK-dependent cell death program. Science 330: 1390-1393, 2010.*
Rudikoff et al. Single amino acid substitution altering antigen-binding specificity. Proc Natl Acad Sci USA 79: 1979-1983, 1982.*
Vajdos et al. Comprehensive functional maps of the antigen-binding site of an anti-ErbB2 antibody obtained with shotgun scanning mutagenesis. J Mol Biol 320: 415-428, 2002.*
Wei et al. tBID, a membrane-targeted death ligand, oligomerizes BAK to release cytochrome c. Genes Develop 14: 2060-2071, 2000.*
Westphal et al. Molecular biology of Bax and Bak activation and action. Biochim Biophys Acta 1813: 521-531, 2011.*
Westphal et al. Building blocks of the apoptotic pore: how Bax and Bak are activated and oligomerize during apoptosis. Cell Death Different 21: 196-205, published online Oct. 25, 2013.*
Wu et al. Humanization of a murine monoclonal antibody by simultaneous optimization of framework and CDR residues. J Mol Biol 294: 151-162, 1999.*

* cited by examiner

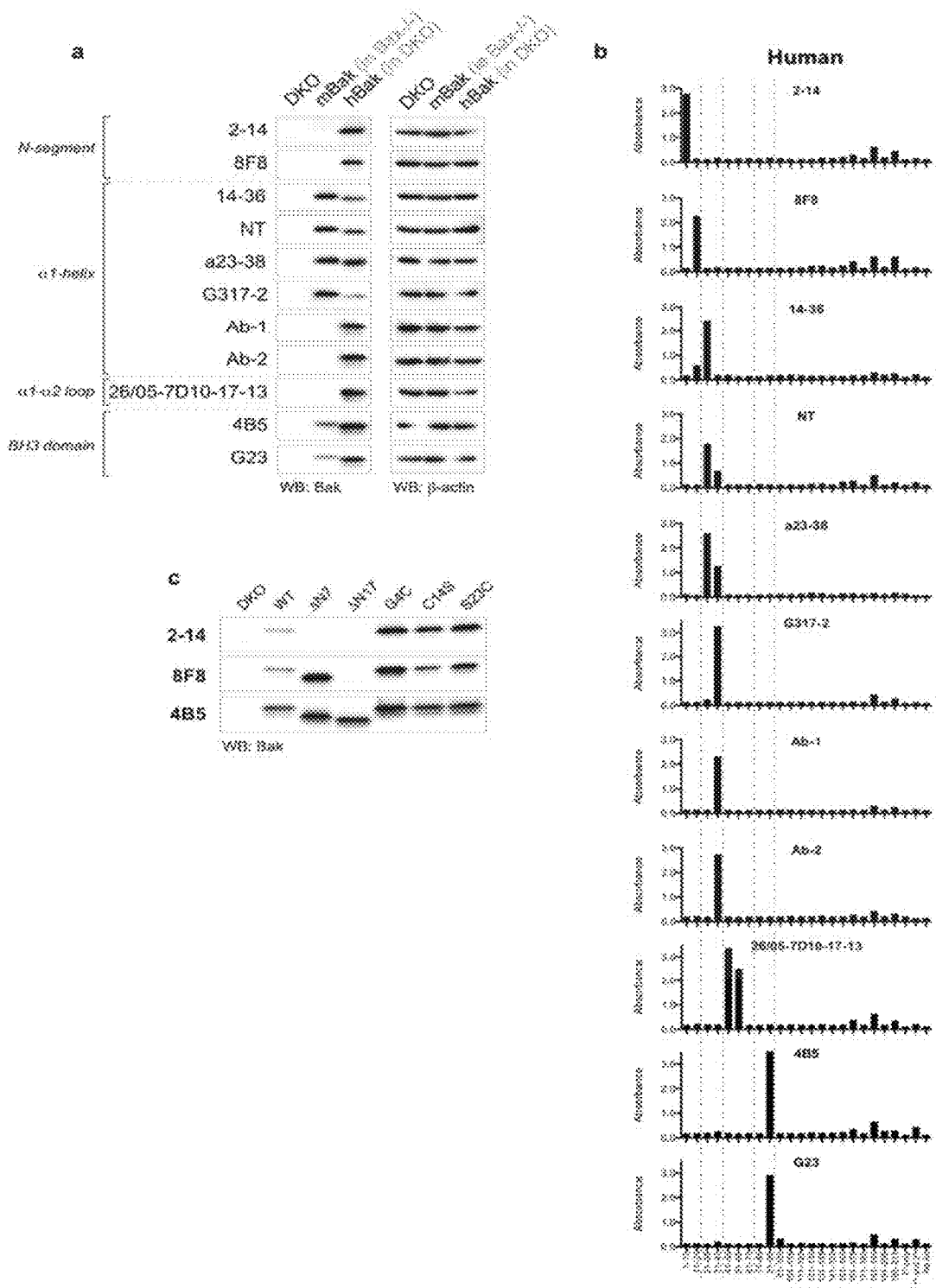
Figures 2a-c

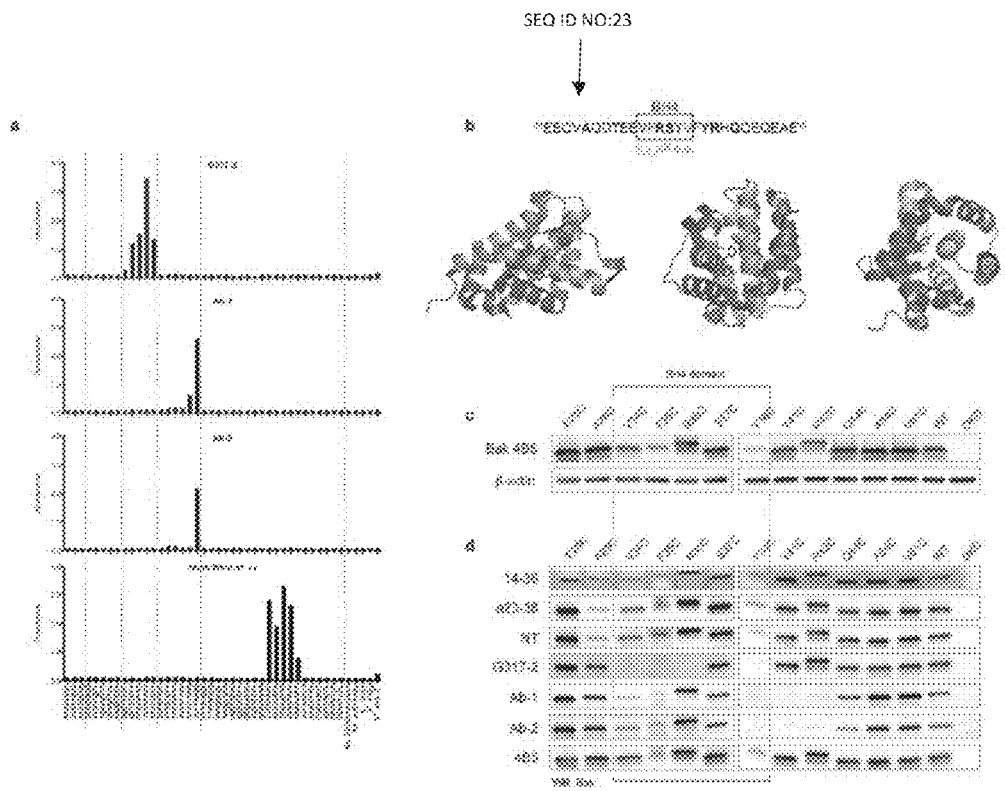
Figures 3a-d
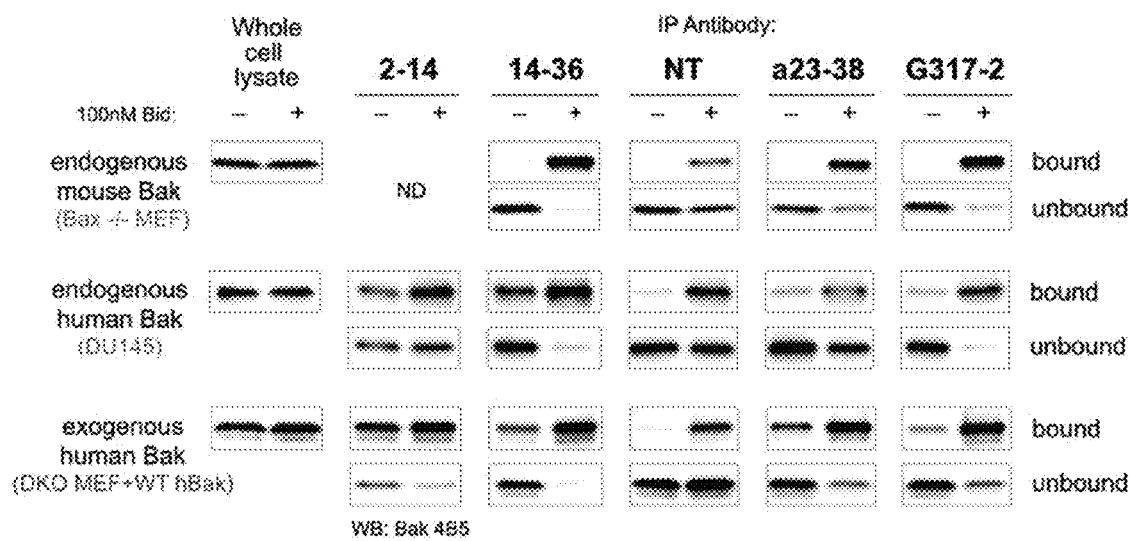
Figure 4

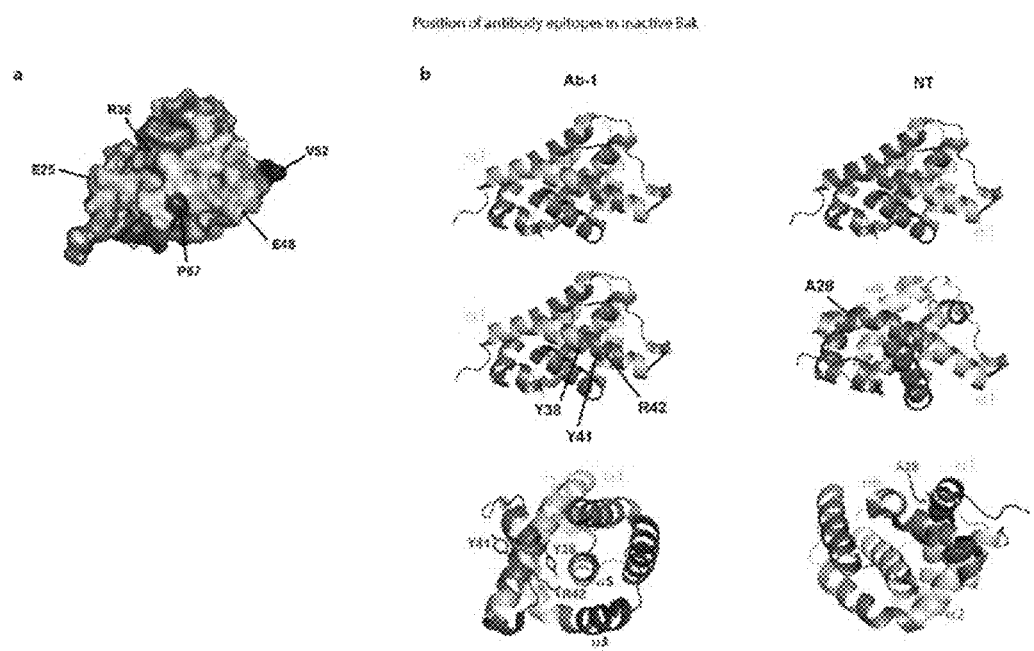
Figures 10a-b
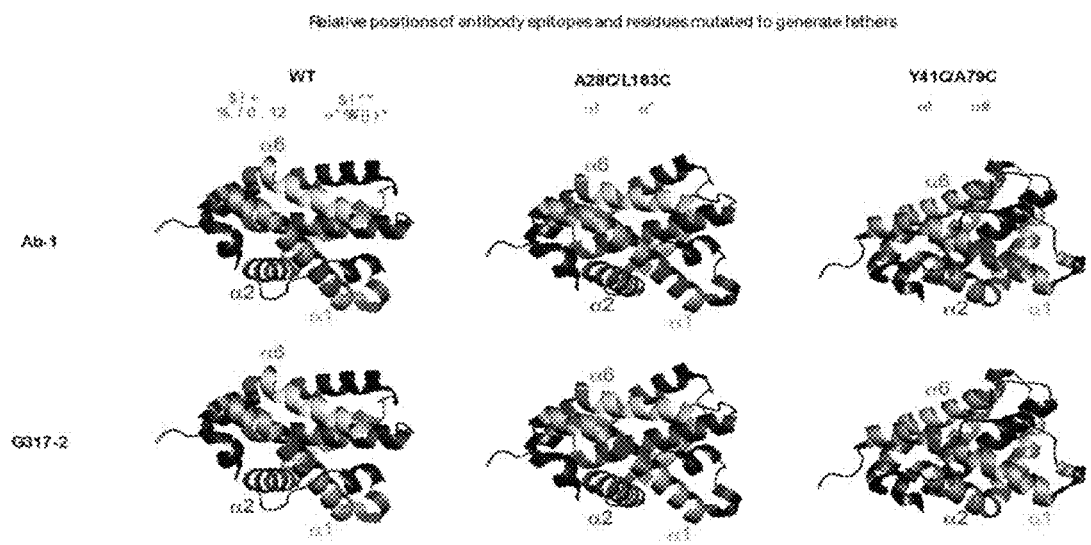
Figure 11

Figures 17a-d

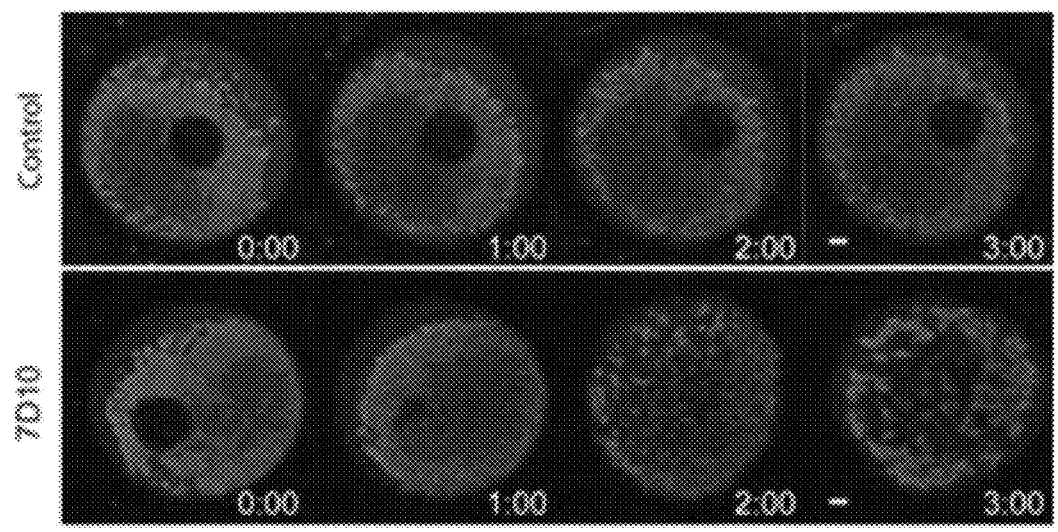
Figure 18
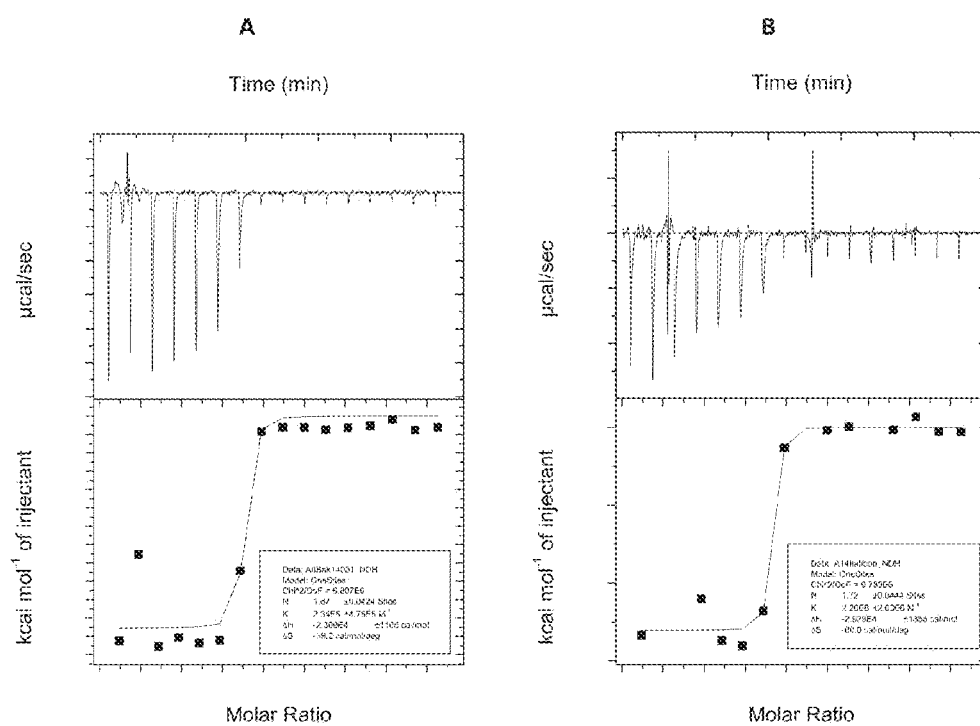
Figures 19a-b

SEQUENCE LISTING

```
<160> NUMBER OF SEQ ID NOS: 22

<210> SEQ ID NO 1
<211> LENGTH: 10
<212> TYPE: PRT
<213> ORGANISM: Artificial Sequence
<220> FEATURE:
<223> OTHER INFORMATION: Synthesized sequence

<400> SEQUENCE: 1

Gly Phe Thr Phe Ser Asn Leu Ala Met Ala
1               5                   10

<210> SEQ ID NO 2
<211> LENGTH: 17
<212> TYPE: PRT
<213> ORGANISM: Artificial Sequence
<220> FEATURE:
<223> OTHER INFORMATION: Synthesized sequence

<400> SEQUENCE: 2

Ser Ile Ser Pro Ala Gly Ile Thr Thr Tyr Tyr Arg Asp Ser Val Lys
1               5                   10                  15

Gly

<210> SEQ ID NO 3
<211> LENGTH: 10
<212> TYPE: PRT
<213> ORGANISM: Artificial Sequence
<220> FEATURE:
<223> OTHER INFORMATION: Synthesized sequence

<400> SEQUENCE: 3

His Thr Gly Lys Ser Ser Phe Phe Asp Tyr
1               5                   10

<210> SEQ ID NO 4
<211> LENGTH: 11
<212> TYPE: PRT
<213> ORGANISM: Artificial Sequence
<220> FEATURE:
<223> OTHER INFORMATION: Synthesized sequence
```

<400> SEQUENCE: 4

Lys Ala Thr Glu Asn Ile Asn Thr Tyr Leu Ala
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Synthesized sequence

<400> SEQUENCE: 5

Ser Gly Ser Thr Leu Gln Ser
1               5

<210> SEQ ID NO 6
<211> LENGTH: 9
<212> TYPE: PRT
<213> ORGANISM: Artificial Sequence
<220> FEATURE:
<223> OTHER INFORMATION: Synthesized sequence

<400> SEQUENCE: 6

Gln Gln His Asn Glu Tyr Pro Leu Thr
1               5

<210> SEQ ID NO 7
<211> LENGTH: 138
<212> TYPE: PRT
<213> ORGANISM: Artificial Sequence
<220> FEATURE:
<223> OTHER INFORMATION: Synthesized sequence

<400> SEQUENCE: 7

Met Asp Phe Arg Leu Ser Leu Ala Phe Leu Val Leu Ile Lys Ala
1               5                   10                  15

Val Gln Cys Glu Val Glu Leu Val Glu Ser Gly Gly Asp Leu Val Gln
            20                  25                  30

Pro Gly Arg Ser Leu Lys Leu Ser Cys Ala Ala Ser Gly Phe Thr Phe
        35                  40                  45

Ser Asn Leu Ala Met Ala Trp Val Arg Gln Thr Pro Thr Lys Gly Leu
    50                  55                  60

Glu Trp Val Ala Ser Ile Ser Pro Ala Gly Ile Thr Thr Tyr Tyr Arg
65                  70                  75                  80

Asp Ser Val Lys Gly Arg Phe Thr Ile Ser Arg Asp Asn Ala Arg Asn
                85                  90                  95

Thr Gln Tyr Leu Gln Met Asp Ser Leu Arg Ser Glu Asp Thr Ala Thr
            100                 105                 110

Tyr Tyr Cys Ala Arg His Thr Gly Lys Ser Ser Phe Phe Asp Tyr Trp
        115                 120                 125

Gly Gln Gly Val Met Val Thr Val Ser Ser
    130                 135

<210> SEQ ID NO 8
<211> LENGTH: 127
<212> TYPE: PRT
<213> ORGANISM: Artificial Sequence
<220> FEATURE:
<223> OTHER INFORMATION: Synthesized sequence

<400> SEQUENCE: 8

```
Met Arg Val Gln Ile Gln Phe Leu Gly Leu Leu Leu Trp Thr Ser
1               5                   10                  15

Val Val Gln Cys Asp Val Gln Met Thr Gln Ser Pro Tyr Leu Ala
            20                  25                  30

Ala Ser Pro Gly Glu Ser Val Ser Ile Ser Cys Lys Ala Thr Glu Asn
        35                  40                  45

Ile Asn Thr Tyr Leu Ala Trp Tyr Gln Ala Lys Pro Gly Lys Thr Thr
    50                  55                  60

Lys Leu Leu Leu Tyr Ser Gly Ser Thr Leu Gln Ser Gly Thr Pro Ser
65                  70                  75                  80

Arg Phe Ser Gly Ser Gly Ser Gly Thr Asp Phe Thr Leu Thr Ile Ser
                85                  90                  95

Ser Leu Glu Pro Glu Asp Phe Ala Val Tyr Tyr Cys Gln Gln His Asn
            100                 105                 110

Glu Tyr Pro Leu Thr Phe Gly Ser Gly Thr Lys Leu Glu Ile Lys
        115                 120                 125
```

<210> SEQ ID NO 9
<211> LENGTH: 7
<212> TYPE: PRT
<213> ORGANISM: Artificial Sequence
<220> FEATURE:
<223> OTHER INFORMATION: Synthesized sequence

<400> SEQUENCE: 9

```
Gly Val Ala Ala Pro Ala Asp
1               5
```

<210> SEQ ID NO 10
<211> LENGTH: 5
<212> TYPE: PRT
<213> ORGANISM: Artificial Sequence
<220> FEATURE:
<223> OTHER INFORMATION: Synthesized sequence

<400> SEQUENCE: 10

```
Gly Val Ala Ala Pro
1               5
```

<210> SEQ ID NO 11
<211> LENGTH: 414
<212> TYPE: DNA
<213> ORGANISM: Artificial Sequence
<220> FEATURE:
<223> OTHER INFORMATION: Synthesized sequence

<400> SEQUENCE: 11

```
atggacttca ggctcagctt ggcgttcctt gtccttttaa taaaagctgt ccagtgtgag      60
gtggagctgg tcgagtctgg gggagactta gtgcagcctg gaggtccct gaaactctcc     120 tgtgcagcct caggattcac tttcagtaac ttagccatgg cctgggtccg ccagactcca    180
acgaagggtc tggagtgggt cgcatccatt agtcctgctg gtattaccac ctactatcga    240
gactccgtga agggccgatt cactattccc agagataatg caagaaacac ccaatacttg    300
cagatggaca gtctgaggtc tgaggacacg gccacttatt actgtgccag acataccgga    360
aagtcctcct tctttgatta ctggggccaa ggagtcatgg tcacagtctc ctca          414
```

<210> SEQ ID NO 12
<211> LENGTH: 381
<212> TYPE: DNA
<213> ORGANISM: Artificial Sequence

```
<220> FEATURE:
<223> OTHER INFORMATION: Synthesized sequence

<400> SEQUENCE: 12
atgagggtcc agattcagtt tctggggctc cttctgctct ggacatcagt tgtccagtgt    60
gatgtccaaa tgacccagtc tccatcttat cttgctgcgt ctcctggaga aagtgtttcc   120
atcagttgca aggcaactga aaacattaac acatacttag cctggtatca ggcgaaacct   180
gggaaaacga ctaagcttct tctctactct gggtcaactt tgcaatctgg aactccatcg   240
agattcagtg gcagtgggtc tggaacagac ttcacgctca ccatcagcag cctggagcct   300
gaagattttg cagtctacta ctgtcaacaa cataatgaat accctctcac gttcggttct   360
gggaccaagc tggagatcaa a                                             381

<210> SEQ ID NO 13
<211> LENGTH: 7
<212> TYPE: PRT
<213> ORGANISM: Artificial Sequence
<220> FEATURE:
<223> OTHER INFORMATION: mutated amino acid sequence of an epitope
      within the alpha1-alpha2 loop of Bak (P55X)
<220> FEATURE:
<221> NAME/KEY: misc_feature
<222> LOCATION: (5)..(5)
<223> OTHER INFORMATION: Xaa can be any naturally occurring amino acid

<400> SEQUENCE: 13

Gly Val Ala Ala Xaa Ala Asp
1               5

<210> SEQ ID NO 14
<211> LENGTH: 7
<212> TYPE: PRT
<213> ORGANISM: Artificial Sequence
<220> FEATURE:
<223> OTHER INFORMATION: mutated amino acid sequence of an epitope
      within the alpha1-alpha2 loop of Bak (P55C)

<400> SEQUENCE: 14

Gly Val Ala Ala Cys Ala Asp
1               5

<210> SEQ ID NO 15
<211> LENGTH: 7
<212> TYPE: PRT
<213> ORGANISM: Artificial Sequence
<220> FEATURE:
<223> OTHER INFORMATION: mutated amino acid sequence of an epitope
      within the alpha1-alpha2 loop of Bak (G51X)
<220> FEATURE:
<221> NAME/KEY: misc_feature
<222> LOCATION: (1)..(1)
<223> OTHER INFORMATION: Xaa can be any naturally occurring amino acid

<400> SEQUENCE: 15

Xaa Val Ala Ala Pro Ala Asp
1               5

<210> SEQ ID NO 16
<211> LENGTH: 7
<212> TYPE: PRT
<213> ORGANISM: Artificial Sequence
<220> FEATURE:
<223> OTHER INFORMATION: mutated amino acid sequence of an epitope
      within the alpha1-alpha2 loop of Bak (G51C)

<400> SEQUENCE: 16
```

Cys Val Ala Ala Pro Ala Asp
1               5

<210> SEQ ID NO 17
<211> LENGTH: 51
<212> TYPE: PRT
<213> ORGANISM: drosophila

<400> SEQUENCE: 17

Cys Tyr Ser Ala Arg Gly Gly Leu Asn Ile Leu Glu Leu Tyr Ser Ile
1               5                   10                  15

Leu Glu Thr Arg Pro Pro His Glu Gly Leu Asn Ala Ser Asn Ala Arg
            20                  25                  30

Gly Ala Arg Gly Met Glu Thr Leu Tyr Ser Thr Arg Pro Leu Tyr Ser
        35                  40                  45

Leu Tyr Ser
    50

<210> SEQ ID NO 18
<211> LENGTH: 7
<212> TYPE: PRT
<213> ORGANISM: Homo sapiens

<400> SEQUENCE: 18

Thr Glu Glu Val Phe Arg Ser
1               5

<210> SEQ ID NO 19
<211> LENGTH: 5
<212> TYPE: PRT
<213> ORGANISM: Homo sapiens

<400> SEQUENCE: 19

Glu Glu Val Phe Arg
1               5

<210> SEQ ID NO 20
<211> LENGTH: 8
<212> TYPE: PRT
<213> ORGANISM: Homo sapiens

<400> SEQUENCE: 20

Tyr Val Phe Tyr Arg His Gln Gln
1               5

<210> SEQ ID NO 21
<211> LENGTH: 24
<212> TYPE: PRT
<213> ORGANISM: Homo sapiens

<400> SEQUENCE: 21

Glu Gln Glu Ala Glu Gly Val Ala Ala Pro Ala Asp Pro Glu Met Val
1               5                   10                  15

Thr Leu Pro Leu Gln Pro Ser Ser
            20

<210> SEQ ID NO 22
<211> LENGTH: 26
<212> TYPE: PRT
<213> ORGANISM: Homo sapiens

<400> SEQUENCE: 22

-continued

```
Asp Met Arg Pro Glu Ile Trp Ile Ala Gln Glu Leu Arg Arg Ile Gly
1               5                   10                  15

Asp Glu Phe Asn Ala Tyr Tyr Ala Arg Arg
            20              25
```

BAK BINDING PROTEINS

CROSS REFERENCE TO RELATED APPLICATIONS

The present application is a National Stage Application claiming the priority of co-pending PCT Application No. PCT/AU2015/000290 filed May 20, 2015, which in turn, claims priority from Australian Application No. 201402830 filed May 23, 2014 and U.S. Provisional Application Ser. No. 62/002,212 filed May 23, 2014. Applicants claim the benefits of 35 U.S.C. § 120 as to the PCT application, priority under 35 U.S.C. § 119(a-d) as to the said Australian application, and priority under 35 U.S.C. § 119(e) as to the said U.S. Provisional application, and the entire disclosures of all applications are incorporated herein by reference in their entireties.

FIELD

The present application relates to Bak binding proteins.

INTRODUCTION

Apoptosis is essential for normal development and tissue homeostasis, and its perturbed regulation contributes to pathological conditions such as cancer (Czabotar et al., Nat Rev Mol Cell Biol, 15, 49-63, 2013). It is regulated principally by interactions within the Bcl-2 family of proteins, whose members fall into three subclasses. The pro-survival proteins (e.g. Bcl-2, Bcl-xL, Mcl-1) sequester the pro-apoptotic members. The eight or more pro-apoptotic BH3-only proteins (e.g. Bid and Bim) transduce specific types of cellular stress signals and engage other family members. Finally, Bak and Bax are the critical effectors of apoptosis (Lindsten et al., Mol cell, 6, 1389-1399, 2000, Wei et al., Science, 29, 727-730, 2001). Once activated, they form oligomers that permeabilize the mitochondrial outer membrane triggering caspase-driven cell demolition.

Bak activation during apoptosis involves a change from the "non-activated" conformation to several "activated" states (Westphal et al, Biochem Biophys Acta, 1813, 521-31, 2014). The structures of non-activated Bak resembles that of the pro-survival proteins: 9 α-helices form a tight bundle with a surface hydrophobic groove and a buried BH3 domain.

No antibody has previously been reported to activate Bak. It will be clear to the skilled artisan based on the foregoing that there is a need in the art for binding proteins (e.g., antibodies and antibody-derived proteins) that can change the conformation of Bak, in particular binding proteins that can change the conformation of Bak from non-activated to an activated conformation. Such proteins might be useful in inducing apoptosis and treating conditions such as cancer.

SUMMARY

The present disclosure is based on the unexpected production of Bak binding proteins that can change the conformation of Bak. Accordingly, the present disclosure provides a Bak binding protein having an antigen binding domain, wherein the antigen binding domain binds to or specifically binds to Bak, and wherein, upon binding of the antigen binding domain to Bak changes the conformation of Bak.

In an example, the Bak binding protein changes the conformation of Bak from a non-activated to an activated conformation.

One example of a binding protein identified by the present inventors that changes the conformation of Bak from a non-activated to an activated conformation is 26/05-7D10-17-13, an antibody that has a light chain variable region ($V_L$) comprising a sequence set forth in SEQ ID NO: 8 and a heavy chain variable region ($V_H$) comprising a sequence set forth in SEQ ID NO: 7. The inventors are not aware of a previously reported antibody that activates Bak.

Accordingly, the present disclosure also provides a Bak binding protein having an antigen binding domain, wherein the binding domain binds to or specifically binds to an epitope of Bak that is specifically bound by antibody 26/05-7D10-17-13 or that competes with antibody 26/05-7D10-17-13 for binding to Bak, wherein the antibody 26/05-7D10-17-13 has a light chain variable region ($V_L$) comprising a sequence set forth in SEQ ID NO: 8 and a heavy chain variable region ($V_H$) comprising a sequence set forth in SEQ ID NO: 7.

The present disclosure is also based on the unexpected finding that Bak can be activated by binding proteins that bind to epitopes within the α1-α2 loop of Bak. Accordingly, in an example, the Bak binding proteins binding domain binds to or specifically binds to an epitope within the α1-α2 loop of Bak.

In another example, the binding domain binds an epitope comprising a sequence at least about 70% or 80% or 85% or 86% or 90% or 95% or 99% identical to SEQ ID NO: 9. In another example, the binding domain binds an epitope comprising a sequence at least about 70% or 80% or 85% or 86% or 90% or 95% or 99% identical to SEQ ID NO: 10.

In another example, the binding domain binds an epitope comprising a sequence identical to SEQ ID NO: 9 or SEQ ID NO: 10.

In another example, the binding domain binds an epitope comprising a sequence identical to SEQ ID NO: 10.

In another example, the $K_D$ of the Bak binding protein for a polypeptide comprising a sequence set forth in SEQ ID NO: 9 or SEQ ID NO: 10 is about 5 nM or less, when the $K_D$ is determined by Isothermal Titration Microcalorimetry (e.g. using a MicroCal iTC 200 instrument from GE). In another example, the $K_D$ of the Bak binding protein for a polypeptide comprising a sequence set forth in SEQ ID NO: 9 or SEQ ID NO: 10 is about 4.5 nM or less, when the $K_D$ is determined by Isothermal Titration Microcalorimetry (e.g. using a MicroCal iTC 200 instrument from GE). In another example, the $K_D$ of the Bak binding protein for a polypeptide comprising a sequence set forth in SEQ ID NO: 9 or SEQ ID NO: 10 is at least about 2 nM, at least about 2.5 nM, at least about 3 nM, at least about 3.5 nM, at least about 4 nM, when the $K_D$ is determined by Isothermal Titration Microcalorimetry (e.g. using a MicroCal iTC 200 instrument from GE).

In another example, the $K_D$ of the Bak binding protein for full length human Bak (SwissProt Accession No. Q16611.1) is at least about 200 pM or less, at least about 250 pM, at least about 300 pM, at least about 350 pM, at least about 400 pM, at least about 450 pM, when the $K_D$ is determined by Surface Plasmon Resonance (e.g. using a BIAcore 3000 instrument).

In another example, the $K_D$ of the Bak binding protein for human BakΔC25 (residues 1-186 of SwissProt Accession No. Q16611.1) is at least about 200 pM or less, at least about 250 pM, at least about 300 pM, at least about 350 pM, at least about 400 pM, at least about 450 pM, when the $K_D$ is determined by Surface Plasmon Resonance (e.g. using a BIAcore 3000 instrument).

In another example, the $K_D$ of the Bak binding protein for full length human Bak (SwissProt Accession No. Q16611.1) is about 466 pM or less, when the $K_D$ is determined by Surface Plasmon Resonance (e.g. using a BIAcore 3000 instrument).

In another example, the $K_D$ of the Bak binding protein for human BakΔC25 (residues 1-186 of SwissProt Accession No. Q16611.1) is about 466 pM or less, when the $K_D$ is determined by Surface Plasmon Resonance (e.g. using a BIAcore 3000 instrument).

In another example, the $K_D$ of the Bak binding protein for Bak peptide residues E46 to S69 of human Bak is at least about 1.5 nM, at least about 2.0 nM, at least about 2.5 nM, at least about 2.7 nM, when the $K_D$ is determined by Surface Plasmon Resonance.

In another example, the $K_D$ of the Bak binding protein for Bak peptide residues E46 to S69 of human Bak is about 2.9 nM, when the $K_D$ is determined by Surface Plasmon Resonance (e.g. using a BIAcore 3000 instrument).

In another example, the Bak binding protein has one or more of the following activities:
  i) increases cytochrome c release;
  ii) promotes or induces apoptosis;
  iii) reduces or inhibits inactivation of Bak.

In another example, the Bak binding protein binds to one or more or all of the following mutant polypeptides:
  (i) a mutant polypeptide comprising a sequence set forth in SEQ ID NO: 13 (P55X), wherein X is any amino acid other than proline;
  (ii) a mutant polypeptide comprising a sequence set forth in SEQ ID NO: 14 (P55C) that has not been oligmerised by tBid;
  (iii) a mutant polypeptide comprising a sequence set forth in SEQ ID NO: 14 (P55C) that has been oligmerised by tBid;
  (iv) a mutant polypeptide comprising a sequence set forth in SEQ ID NO: 15 (G51X) wherein X is any other amino acid; or
  (v) a mutant polypeptide comprising a sequence set forth in SEQ ID NO: 16 (G51C) that has not been oligmerised by tBid;
at a level that is reduced compared to the level of binding of the Bak binding protein to a polypeptide comprising a sequence set forth in SEQ ID NO: 9 or SEQ ID NO: 10.

In another example, the Bak binding protein is an immunoglobulin or a Bak binding fragment thereof.

In another example, the Bak binding protein is a:
  i) heavy chain immunoglobulin;
  ii) V-like protein;
  iii) adnectin;
  iv) anticalin;
  v) affibody;
  vi) avimer; or
  vii) DARpin.

In another example, the antigen binding domain of the Bak binding protein comprises at least one of:
  (i) a heavy chain variable region ($V_H$) comprising a complementarity determining region (CDR) 1 comprising a sequence at least about 90% identical to SEQ ID NO: 1, a CDR2 comprising a sequence at least about 90% identical to SEQ ID NO: 2 and a CDR3 comprising a sequence at least about 90% identical to SEQ ID NO: 3;
  (ii) a $V_H$ comprising a sequence at least about 89% or 90% or 91% or 92% or 93% or 94% or 95% or 96% or 97% or 98% or 99% identical to a sequence set forth in SEQ ID NOs: 7;
  (iii) a light chain variable region ($V_L$) comprising a CDR 1 comprising a sequence at least about 90% identical to SEQ ID NO: 4, a CDR2 comprising a sequence at least about 90% identical to SEQ ID NO: 5 and a CDR3 comprising a sequence at least about 90% identical to SEQ ID NO: 6;
  (iv) a $V_1$ comprising a sequence at least about 89% or 90% or 91% or 92% or 93% or 94% or 95% or 96% or 97% or 98% or 99% identical to a sequence set forth in SEQ ID NOs: 8;
  (v) a $V_H$ as set forth in (i) and a $V_L$ as set forth in (iii);
  (vi) a $V_H$ as set forth in (i) and a $V_L$ as set forth in (iv);
  (vii) a $V_H$ as set forth in (ii) and a $V_L$ as set forth in (iii); or
  (viii) a $V_H$ as set forth in (ii) and a $V_L$ as set forth in (iv).

In another example, the antigen binding domain of the Bak binding protein comprises at least one of:
  (i) a heavy chain variable region ($V_H$) comprising a CDR 1 comprising a sequence identical to SEQ ID NO: 1, a CDR2 comprising a sequence identical to SEQ ID NO: 2 and a CDR3 comprising a sequence identical to SEQ ID NO: 3; and/or
  (ii) a light chain variable region ($V_L$) comprising a CDR 1 comprising a sequence identical to SEQ ID NO: 4, a CDR2 comprising a sequence identical to SEQ ID NO: 5 and a CDR3 comprising a sequence identical to SEQ ID NO: 6.

In another example, the Bak binding protein comprises an antigen binding domain having a $V_H$ and $V_L$ and wherein, if the $V_H$ and $V_L$ are in a single polypeptide chain, the Bak binding protein is:
  (i) a single chain Fv fragment (scFv);
  (ii) a dimeric scFv (di-scFv); or
  (iii) one of (i) or (ii) linked to a constant region of an antibody, Fc or a heavy chain constant domain ($C_H$) 2 and/or $C_H$3; or
if the $V_H$ and $V_L$ are in separate polypeptide chains the protein is:
  (i) a diabody;
  (ii) a triabody;
  (iii) a tetrabody;
  (iv) a Fab;
  (v) a F(ab')$_2$;
  (vi) a Fv;
  (vii) one of (i) to (vi) linked to a constant region of an antibody, Fc or a heavy chain constant domain ($C_H$) 2 and/or $C_H$3; or
  (ix) an antibody.

In another example, the Bak binding protein is a Bak binding antibody.

In another example, the Bak binding antibody has an antigen binding domain, wherein the antigen binding domain binds to or specifically binds to Bak, and wherein, upon binding of the antigen binding domain to Bak changes the conformation of Bak and wherein, the antigen binding domain comprises at least one of:
  (i) a heavy chain variable region ($V_H$) comprising a CDR 1 comprising a sequence at least about 90% identical to SEQ ID NO: 1, a CDR2 comprising a sequence at least about 90% identical to SEQ ID NO: 2 and a CDR3 comprising a sequence at least about 90% identical to SEQ ID NO: 3;

(ii) a $V_H$ comprising a sequence at least about 89% or 90% or 91% or 92% or 93% or 94% or 95% or 96% or 97% or 98% or 99% identical to a sequence set forth in SEQ ID NOs: 7;

(iii) a light chain variable region ($V_L$) comprising a CDR 1 comprising a sequence at least about 90% identical to SEQ ID NO: 4, a CDR2 comprising a sequence at least about 90% identical to SEQ ID NO: 5 and a CDR3 comprising a sequence at least about 90% identical to SEQ ID NO: 6;

(iv) a $V_L$ comprising a sequence at least about 89% or 90% or 91% or 92% or 93% or 94% or 95% or 96% or 97% or 98% or 99% identical to a sequence set forth in SEQ ID NOs: 8;

(v) a $V_H$ as set forth in (i) and a $V_L$ as set forth in (iii);
(vi) a $V_H$ as set forth in (i) and a $V_L$ as set forth in (iv);
(vii) a $V_H$ as set forth in (ii) and a $V_L$ as set forth in (iii); or
(viii) a $V_H$ as set forth in (ii) and a $V_L$ as set forth in (iv).

In another example, the antigen binding domain of the Bak binding antibody comprises:

(i) a heavy chain variable region ($V_H$) comprising a CDR 1 comprising a sequence set forth in SEQ ID NO: 1, a CDR2 comprising a sequence set forth in SEQ ID NO: 2 and a CDR3 comprising a sequence set forth in SEQ ID NO: 3; and (ii) a light chain variable region ($V_L$) comprising a CDR 1 comprising a sequence set forth in SEQ ID NO: 4, a CDR2 comprising a sequence set forth in SEQ ID NO: 5 and a CDR3 comprising a sequence set forth in SEQ ID NO: 6.

In another example, the antigen binding domain of the Bak binding antibody comprises:

(i) a $V_L$ comprising a sequence set forth in SEQ ID NOs: 7;
(ii) a $V_L$ comprising a sequence set forth in SEQ ID NOs: 8.

In another example, the Bak binding antibody is 26/05-7D10-17-13.

In another example, the Bak binding protein or Bak binding antibody is conjugated to another compound.

In another example, the Bak binding antibody is 26/05-7D10-17-13 produced by the hybridoma deposited with ECACC on 16 Apr. 2015 under the provisions of the Budapest Treaty under deposit accession number 15041601.

In another example, the present disclosure provides a nucleic acid encoding the above exemplified Bak binding proteins, antibodies or polypeptides thereof.

In another example, the present disclosure provides a nucleic acid comprising a sequence at least about 89% or 90% or 91% or 92% or 93% or 94% or 95% or 96% or 97% or 98% or 99% identical to a sequence set forth in SEQ ID NO: 11.

In another example, the present disclosure provides a nucleic acid comprising a sequence at least about 89% or 90% or 91% or 92% or 93% or 94% or 95% or 96% or 97% or 98% or 99% identical to a sequence set forth in SEQ ID NO: 12.

In another example, the present disclosure provides a nucleic acid comprising the sequence set forth in SEQ ID NO: 11 and/or SEQ ID NO: 12.

In another example, the present disclosure provides an expression construct comprising the above exemplified nucleic acids.

In another example, the present disclosure provides an isolated or recombinant cell expressing the above exemplified Bak binding proteins or antibodies.

In another example, the present disclosure provides a composition comprising the above exemplified Bak binding proteins or antibodies and a pharmaceutically acceptable carrier.

In another example, the present disclosure provides a method for treating or preventing a hyperproliferative disorder (e.g. cancer) in a subject, the method comprising administering the above exemplified Bak binding proteins, antibodies or composition.

In another example, the present disclosure provides use of the above exemplified Bak binding proteins, antibodies or composition in the manufacture of a medicament for the treatment of a hyperproliferative disorder (e.g. cancer).

In another example, the present disclosure provides the above exemplified Bak binding proteins, antibodies or composition for use in the treatment of a hyperproliferative disorder (e.g. cancer).

In another example, the present disclosure provides an in-vitro method of activating Bak in a cell, the method comprising:
 i) contacting a cell with the above exemplified binding proteins or antibodies; and
 ii) optionally, detecting activation of Bak.

In another example, the present disclosure provides an in-vitro method of inducing apoptosis in a cell the method comprising contacting a cell with the above exemplified binding proteins or antibodies and, optionally detecting if apoptosis is induced.

In another example, the present disclosure provides a method of identifying a molecule that changes the conformation of Bak, the method comprising:
 i) contacting Bak or a fragment thereof comprising the α1-α2 loop with the molecule in the presence of antibody 26/05-7D10-17-13 or that competes with antibody 26/05-7D10-17-13 for binding to Bak, wherein the antibody 26/05-7D10-17-13 has a light chain variable region ($V_L$) comprising a sequence set forth in SEQ ID NO: 8 and a heavy chain variable region ($V_H$) comprising a sequence set forth in SEQ ID NO: 7;
 ii) identifying a molecule that binds to Bak or the fragment thereof and competitively inhibits binding of antibody 26/05-7D10-17-13 to the Bak or fragment thereof; and
 iii) optionally, determining whether the molecule identified in step ii) changes the conformation of Bak.

In another example, the present disclosure provides a method of identifying a molecule that binds the α1-α2 loop of Bak, the method comprising:
 i) contacting Bak or a fragment thereof comprising the α1-α2 loop with the molecule in the presence of antibody 26/05-7D10-17-13 or that competes with antibody 26/05-7D10-17-13 for binding to Bak, wherein the antibody 26/05-7D10-17-13 has a light chain variable region ($V_L$) comprising a sequence set forth in SEQ ID NO: 8 and a heavy chain variable region ($V_H$) comprising a sequence set forth in SEQ ID NO: 7; and
 ii) identifying a molecule that binds to Bak or the fragment thereof and competitively inhibits binding of antibody 26/05-7D10-17-13 to the Bak or fragment thereof.

In another example of the above method of identifying a molecule that binds the α1-α2 loop of Bak, the method screens for molecules that bind an epitope of Bak comprising a sequence at least about 70% or 80% or 85% or 86% or 90% or 95% or 99% identical to SEQ ID NO: 9.

In another example of the above method of identifying a molecule that binds the α1-α2 loop of Bak, the method screens for molecules that bind an epitope of Bak comprising a sequence at least about 70% or 80% or 85% or 86% or 90% or 95% or 99% identical to SEQ ID NO: 10.

In another example of the above method of identifying a molecule that binds the α1-α2 loop of Bak, the method screens for molecules that bind an epitope of Bak comprising a sequence set forth in SEQ ID NO: 9 or SEQ ID NO: 10.

In another example of the above method of identifying a molecule that binds the α1-α2 loop of Bak, the method additionally comprises isolating the identified molecule and, optionally, formulating the isolated molecule with a pharmaceutically acceptable carrier.

In another example, Bak binding proteins encompassed by the present disclosure are isolated and/or purified from a cell.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some figures contain coloured representations or entities. Coloured versions of the figures are available from the Patentee upon request or from an appropriate Patent Office. A fee may be imposed if obtained from a Patent Office.

FIG. 2A-2C: N-terminal epitope localization (A) Bak antibodies recognize linear epitopes in human Bak, but only a subset recognize mouse Bak. Whole cell lysates from MEFs expressing no Bak (bax-/-bak-/- (DKO)), mouse Bak (bax -/-) or WT human Bak (in DKO) were analysed by western blot (n=2) using the indicated antibodies. Blots were re-probed with B-actin to compare loading. (B) Most Bak epitopes map to peptides from the N-terminus. Histograms showing immunoreactivity of Bak antibodies towards biotinylated 15-mer hBak peptides, as determined by ELISA. X-axis labels indicate residue number or control reaction conditions. Data are representative of at least three independent experiments. (C) The epitopes of antibodies binding in the Bak N-segment are distinct. 2-14 and 8F8, which bound to peptides corresponding to N-segment residues in (B), were tested by western blot (n=2) for their ability to bind N-terminally-truncated or single residue mutants of hBak (as indicated) expressed in DKO MEFs. Based on loss of signal, residues 1-7 are required for the 2-14 antibody to bind Bak whereas residues 8-17 are required for the 8F8 antibody to bind Bak (as also shown in Dewson et al., Mol Cell, 36, 696-703, 2009). Binding by 4B5 is shown as a reference for expression levels of various mutants, since its epitope in the BH3 domain is C-terminal to the N-segment (see Dewson et al., Mol Cell, 30, 369-380, 2008, FIG. 1b).

FIG. 3A-3D: Epitopes in α1 and residues of α1 important for Bak function. (A) Precise positioning of the G317-2, Ab-1, Ab-2 and 26/05-7D10-17-13 epitopes. Histograms showing immunoreactivity of Bak antibodies towards biotinylated 8-mer peptides that collectively span residues 20-65 of human Bak, as determined by ELISA. X-axis labels indicate peptide sequence or control reaction conditions. Data are representative of at least three independent experiments. (B) Diagrams showing the position of the BH4 domain (Kvansakul et al., Cell Death Differ, 15, 1564-1571, 2008) in the Bak α1 sequence (SEQ ID NO:23) and structure of inactive Bak (2IMS, Moldoveanu et al., Molecular Cell 24, 677-688, 2006). Residues in bold were mutagenized for experiments illustrated in C and D. Three different orientations of the structure are shown. Note the hydrophobic side-chains of the BH4 domain (red) within α1 (yellow) point towards α5 (pink) and α6 (cyan) residues in the core of Bak. (C) Hydrophobic residues in the BH4 domain are important for Bak function. Whole cell lysates from DKO MEFs expressing Bak mutants with cysteine substitutions at different positions in α1 (as indicated) were analysed by western blot (n=2) using anti-Bak 4B5, since its epitope is C-terminal to the α1 helix (see Dewson et al., Mol Cell, 30, 369-380, 2008, FIG. 1b). Y38C, F35C and, to a lesser extent, V34C exhibited consistently weaker signals than other α1 mutants. Note, E25C migrated a little faster and R36C and R42C slightly slower than WT hBak, due to their cysteine substitutions changing the overall net charge of Bak. Blots were re-probed with B-actin to compare loading. (D) Three sets of Bak α1 residues (A28, V34-R36, & S37-Q44) are important for antibody binding. The ability of antibodies (as indicated on the left) to bind Bak mutants with cysteine substitutions at different positions in α1 (as indicated above) was compared by western blotting (n=3); lysates from DKO MEFs expressing no Bak, WT Bak or mutations C-terminal to α1 (A54C, V61C) were included as negative and positive controls. Based on diminished signals (compared to binding by 4B5), A28 is required for NT, a23-38, and 14-36 binding; V34-R36, & Y38 are required for G317-2 binding; S37-Q44 are required for Ab-1 and Ab-2 binding.

FIG. 4: Ability of antibodies to recognize Bak in different conformations. Membrane fractions from cells expressing Bak (as indicated) were incubated (30 min, 30° C.) with (+) or without (−) Bid, solubilized with digitonin, and incubated with the Bak antibodies shown. Bak in immunoprecipitates and whole cell lysate controls was detected by western blot using the 4B5 antibody. Data are representative of at least two independent experiments ND, not done.

C.), 10 uM Bim peptide (30° C.) or heat (44° C.). Supernatant and pellet fractions were collected and analysed by western blot (n=3). Note that all stimuli caused efficient release of cytochrome c into the supernatant only in the absence of CuPhe. (D) G317-2, but not Ab-1, can bind to activated Y41CA79C Bak. Membrane fractions from DKO MEF expressing human Bak (as indicated) were treated as in FIG. 3 (n=3). (E) G317-2 can substitute for Ab-1 in intracellular FACS assays for Bak activation. Digitonin-permeabilized DKO MEFs expressing WT human Bak or the A28C/L163C and Y41C/A79C double mutants were treated with (solid line) or without (filled histograms) 100 nM Bid (30° C., 30 min) and incubated with Ab-1 or G317-2. Primary antibody binding was detected by incubation with RPE-labelled secondary antibody. Dotted lines show signals for cells incubated without primary antibody (and are the same in G317-2 and Ab-1 plots for each form of Bak). Doublets and debris have been excluded by gating using FSC and SSC. In the top two rows the signal profiles for G317-2 and Ab-1 in cells expressing WT Bak and A28C/L163C are highly similar. In contrast, Ab-1 is completely unable to bind to BIDactivated Y41C/A79C, unlike G317-2. The bottom row of FACS plots shows the proportion of non-permeabilized cells expressing GFP as a marker of Bak expression. Note, the profiles of Bid-treated cells (except for Y41C/A79C and Ab-1) closely match the GFP expression levels, indicating all cells expressing Bak responded to Bid. (F) Mouse Bak activation can be measured by intracellular FACS using G317-2. Bax-/- MEFs treated as in E.

FIG. 6A-6D: BH4 exposure. (A) Tethering the α1 and α2 helices allows α1 movement. Permeabilized DKO MEFs expressing Y41C/A79C Bak were incubated with (Tethered) or without (Untethered) 200 uM CuPhe, then treated for 30 min with (black lines) or without (filled histograms) 100 nM Bid (30° C.), 10 uM Bim peptide (30° C.) or heat (44° C.), and stained with G317-2 as in FIG. 4E. Representative FACS signals are shown on the right, with responses to stimuli quantified on the left. Data in graph are mean and standard deviation of at least 3 independent FACS experiments. (B) Tethering the α1 and α6 helices completely blocks α1 movement. DKO Mefs expressing A28C/L163C Bak were assayed as in (A). (C) Tethering the N-segment to the α6-7 loop restrains, but does not block, movement of α1. DKO Mefs expressing WT Bak were assayed as in (A). (D) Comparison of mean fluorescent intensities (MFI) of tethered and untethered BID-treated G317-2-positive cell populations graphed in (A) and (C). Lines connect data from the same experiment.

Figure 7:
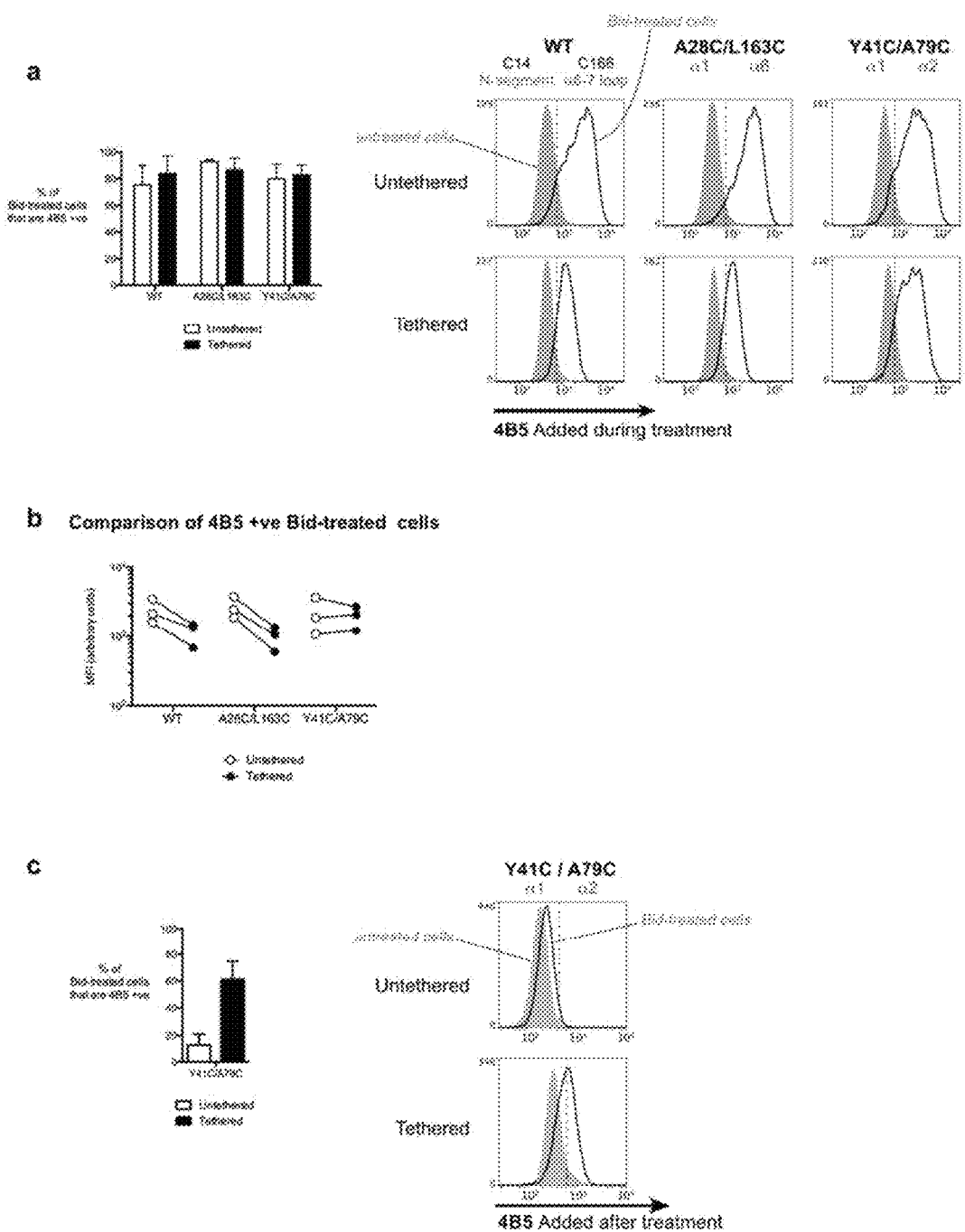

FIG. 7A-7C: BH3 exposure precedes BH4 exposure. (A) Permeabilized DKO Mefs expressing Bak (as indicated) were treated with CuPhe and Bid as in FIG. 5(A). BH3 exposure was detected by addition of 4B5 to cells prior to Bid. After Bid treatment, 4B5 binding was detected by incubating with RPE-labelled secondary antibody. Doublets and debris have been excluded by gating using FSC and SSC. Representative FACS signals are shown on the right, with responses of treated cells quantified on the left. Data in graph are mean and standard deviation of at least 3 independent FACS experiments. (B) Comparison of mean fluorescent intensities (MFIs) of tethered and untethered BIDtreated 4B5-positive cell populations graphed in (A). Lines connect data from the same experiment. (C) The α1-α2 tether allows α1 to move but prevents dimerization via BH3:groove interaction. Permeabilized DKO MEF expressing Bak (as indicated) were treated with CuPhe and Bid as in FIG. 5(A) and subsequently incubated with 4B5. Note, the 4B5 epitope is usually inaccessible after Bid-treatment, as it is part of the BH3:groove interface (Dewson et al., Mol Cell, 36, 696-703, 2008). 4B5 binding was detected by incubation with RPE-labelled secondary antibody. Doublets and debris have been excluded by gating using FSC and SSC. Representative FACS signals are shown on the right, with responses of treated cells quantified on the left. Data in graph are mean and standard deviation of at least 3 independent FACS experiments.

Figure 8:
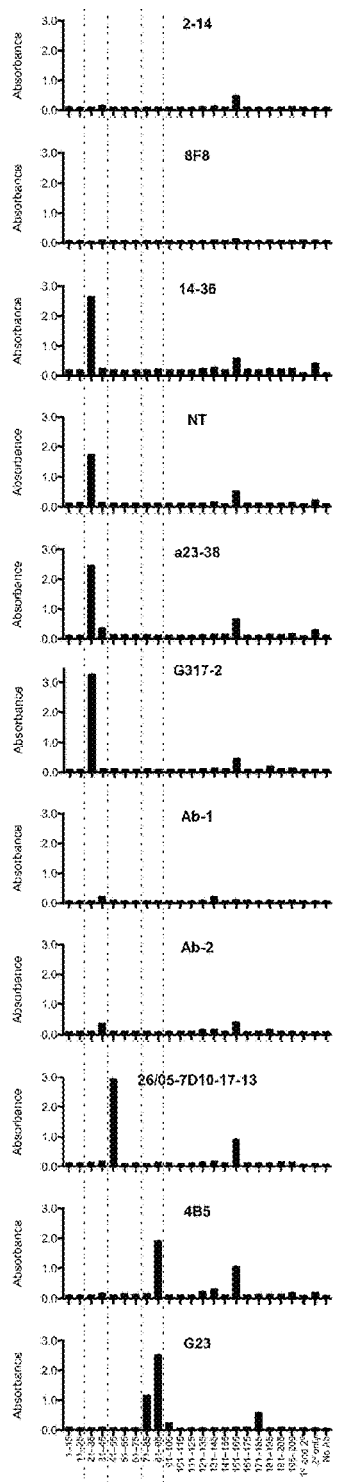

FIG. 8: Binding of antibodies to mouse Bak peptides. Histograms showing immunoreactivity of Bak antibodies towards biotinylated 15-mer mBak peptides, as determined by ELISA. X-axis labels indicate residue number or control reaction conditions. Data are representative of at least three independent experiments.

Figure 9:
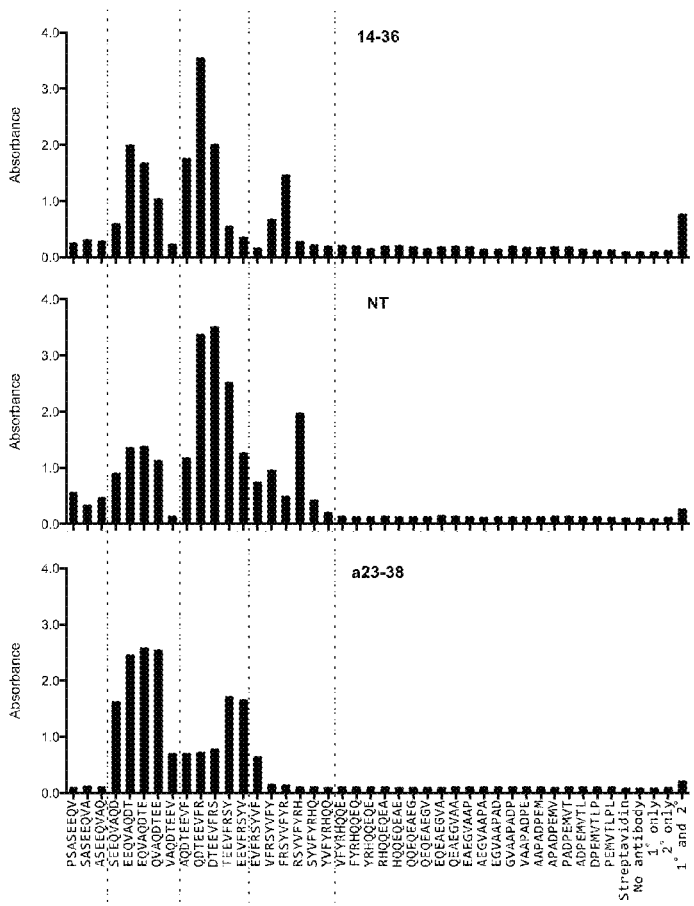

FIG. 9: α1 binding patterns for polyclonal Bak antibodies. Histograms showing immunoreactivity of Bak antibodies towards biotinylated 8-mer peptides that collectively span residues 20-65 of human Bak, as determined by ELISA. X-axis labels indicate peptide sequence or control reaction conditions. Data are representative of at least three independent experiments.

FIG. 10A-10B: Position of epitopes in inactive Bak structure. (A) The α1-α2 loop and many α1 residues are exposed at the surface of inactive Bak. Residues comprising the α1 helix are marked in yellow/orange, while residues in the α1-α2 loop required for 26/05-7D10-17-13 binding are marked in shades of blue. Top panel: Cartoon of alpha helices in the 2IMS structure of inactive Bak (Moldoveanu et al., Molecular Cell 24, 677-688, 2006). Bottom panel: surface representation of the 2IMS structure in the same orientation as in the top panel. Note, selected residues highlighted with darker colours show their position relative to the α1-α2 loop. (B) Position in the inactive Bak structure (2IMS) of key residues in cryptic α1 epitopes. Residues comprising the α1 helix are marked in yellow, while residues in the epitopes are marked in blue. Labelled residues highlighted in red in the lower panels are required for antibody binding. Note how they predominantly face toward other helices rather than the surface of the protein. To assist with orientation in some views selected helices are coloured as follows: α2—lilac, α5—pink, α6—cyan.

FIG. 11: Position of the Ab-1 and G317-2 epitopes relative to tether residues. The Ab-1 and G317-2 epitopes (blue) and native or cysteine-substituted residues (red) are depicted in the 2IMS inactive Bak structure. Helices are coloured as follows: α1—yellow, α2—lilac, α6—cyan. Note: (i) in Y41C/A79C Bak the Y41 residue is clearly visible in the center of the Ab-1 epitope; (ii) since the structure was derived from calpain-truncated Bak (Moldoveanu et al., Molecular Cell 24, 677-688, 2006), in the case of WT Bak the most N terminal residue present (S21) is marked red as a surrogate for C14; (iii) for each form of Bak the orientation of the structures has been varied slightly to maximize visibility of the salient features.

Figure 12:
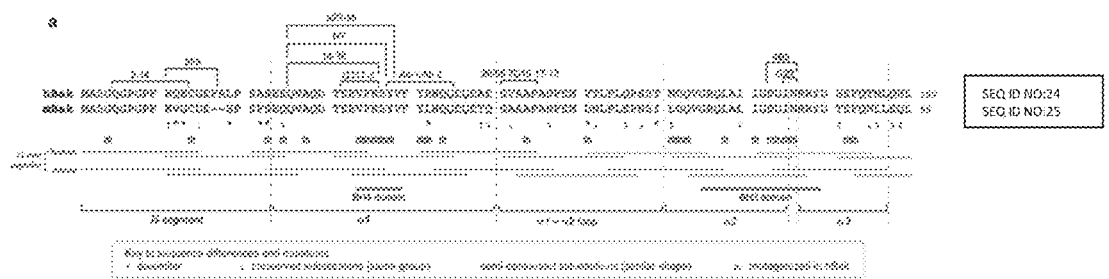

FIG. 12: Summary of epitope mapping data. The noted hBAK sequence corresponds to SEQ ID NO: 24 and mBak sequence corresponds to SEQ ID NO: 25.

Figure 13:
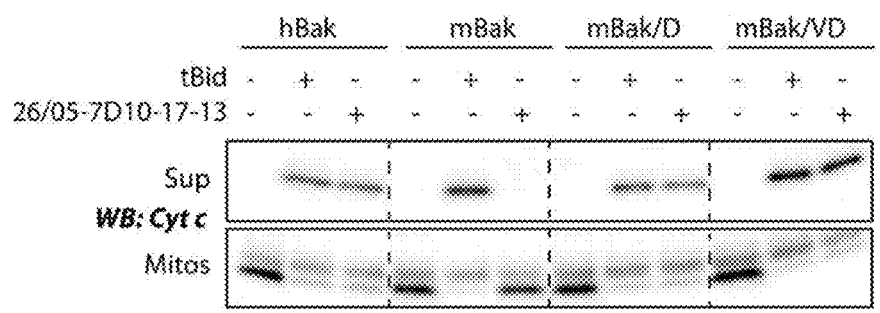

FIG. 13: Mitochondrial membrane fractions incubated with either tBid or 26/05-7D10-17-13 and tested for cytochrome c release.

Figure 14:
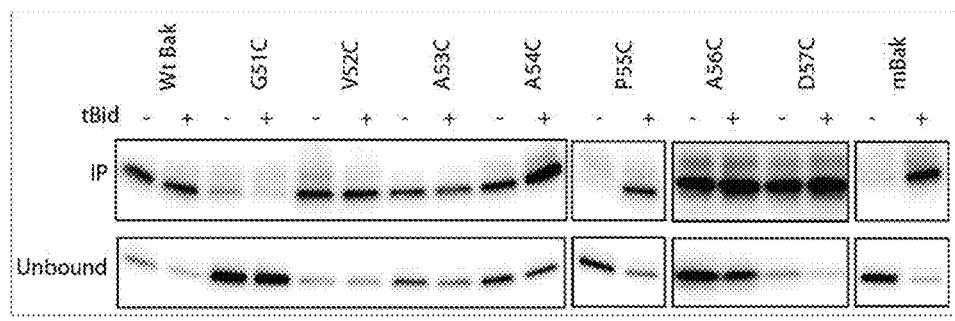

FIG. 14: Immunoprecipitation of Bak by 26/05-7D10-17-13 requires G51, and generally increases after Bak is activated by tBid. Membranes expressing the indicated Bak variants were incubated with or without tBid then immunoprecipitated with 26/05-7D10-17-13.

Figure 15:
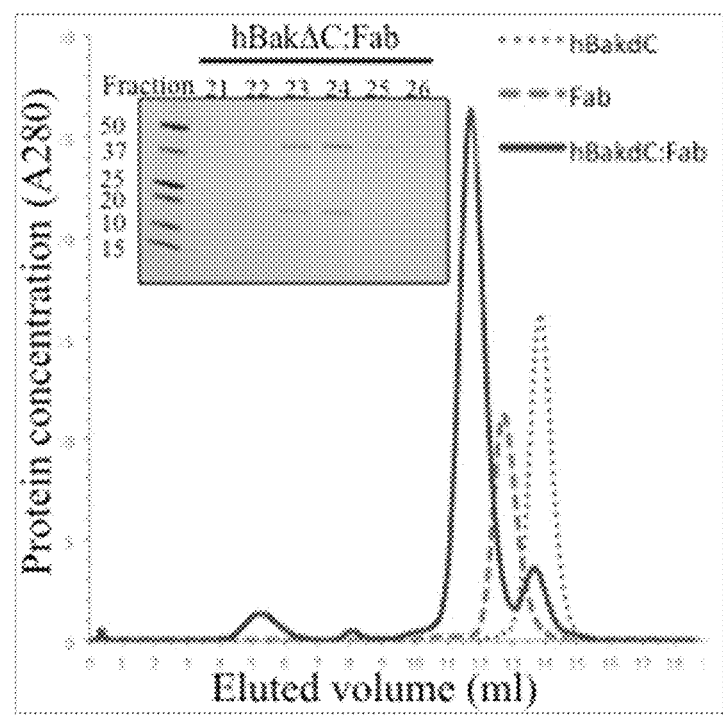

FIG. 15: Complex of Bak bound to 26/05-7D10-17-13 Fab purified for structural studies. The mixture of hBakΔC and Fab at a 1.5:1 ratio migrates as a single peak corresponding to a higher molecular weight fraction. Inset, SDS-PAGE analysis of protein fractions corresponding to the hBakAC:Fab peak.

Figure 16:
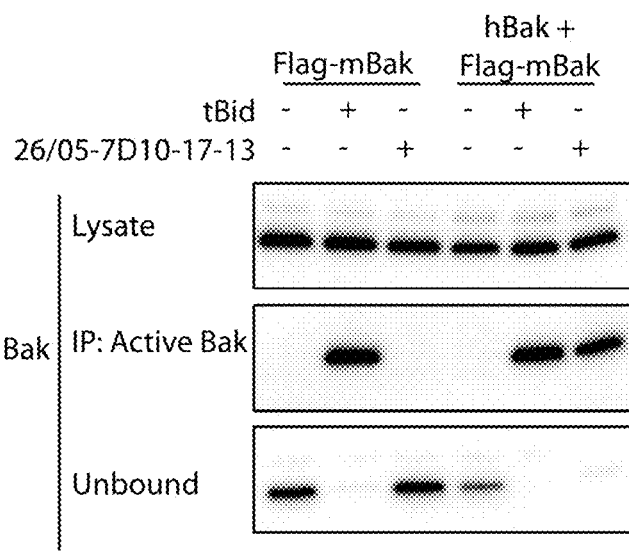

FIG. 16: Auto-activation can occur from human Bak to mouse Bak, at mitochondria. While 26/05-7D10-17-13 cannot activate mouse Bak (lane 3), human Bak activated by 26/05-7D10-17-13 can activate mouse Bak (lane 6).

FIG. 17A-17D: The 26/05-7D10-17-13 Fab activates Bak with similar stoichiometry. (a) Papain cleavage of the 26/05-7D10-17-13 rat MAb generates ~40 kD Fab and ~25 kD Fc fragments. (b) Purification of Fab and Fc by Mono S. Fractions collected from the Mono S chromatographic separation (upper panel) were analysed by nonreducing SDS-PAGE and Coomassie staining (lower panel). NaCl gradient (0-500 mM) is indicated by the sloping line. (c) The 26/05-7D10-17-13 Fab induces Bak conformation change and oligomerisation. Permeabilized Bak−/−Bax−/− MEFs stably expressing human Bak were permeabilized and incubated with tBid, the 26/05-7D10-17-13 MAb or the 26/05-7D10-17-13 Fab. Aliquots incubated with proteinase K (upper panel) show increased susceptibility after activation. (Both Ab and Fab mask one of two cleavage sites.) Aliquots were also exposed to oxidant (CuPhe, lower panel) and western blotted for Bak to distinguish monomers (M), intramolecular-linked monomers (Mx) and dimers (D). (d) Stoichiometry of Bak activation by both Ab and Fab is around 1:10. Membrane fractions were incubated as in c, but with the Ab and Fab serially diluted. Note that Bak is present at ~2 nm.

Coomassie staining (lower panel). NaCl gradient (0-500 mM) is indicated by the sloping line. (c) The 26/05-7D10-17-13 Fab induces Bak conformation change and oligomerisation. Permeabilized Bak−/−Bax−/− MEFs stably expressing human Bak were permeabilized and incubated with tBid, the 26/05-7D10-17-13 MAb or the 26/05-7D10-17-13 Fab. Aliquots incubated with proteinase K (upper panel) show increased susceptibility after activation. (Both Ab and Fab mask one of two cleavage sites.) Aliquots were also exposed to oxidant (CuPhe, lower panel) and western blotted for Bak to distinguish monomers (M), intramolecular-linked monomers (Mx) and dimers (D). (d) Stoichiometry of Bak activation by both Ab and Fab is around 1:10. Membrane fractions were incubated as in c, but with the Ab and Fab serially diluted. Note that Bak is present at ~2 nm.

FIG. 18: 26/05-7D10-17-13 induces dramatic changes in mitochondrial morphology in human oocytes. Control oocytes labelled with TMRM (which stains mitochondria) shows a consistent pattern of mitochondrial labelling during the time course of imaging. In contrast oocytes injected with 26/05-7D10-17-13 Fab show a dramatic reorganisation and aggregation of mitochondria. Represented images from 10 control and 9 26/05-7D10-17-13-injected oocytes. Images are of single Z-slices, time is h:mm after microinjection, scale bar=10 μm.

FIG. 19A-19B: Isothermal Titration Microcalorimetry binding profile of 26/05-7D10-17-13 with loop peptide ($^{46}$EQEAEGVAAPADPEMVTLPLQPSS$^{69}$; SEQ ID NO: 21) at 25° C. A) Titration with Ab at 5 μM and peptide at 100 μM. $K_D$ is <4.3 nM; B) Titration with Ab at 2.5 μM and peptide at 50 μM. $K_D$ is <4 nM. Top panel shows data obtained for automatic injections, 2.43 μl each of loop peptide. The bottom panel shows the integrated curve showing experimental (•) points and the best fit (-)

KEY TO SEQUENCE LISTING

SEQ ID NO: 1 is an amino acid sequence of complementarity determining region 1 of the heavy chain of 26/05-7D10-17-13 (CDR1).

SEQ ID NO: 2 is an amino acid sequence of complementarity determining region 2 of the heavy chain of 26/05-7D10-17-13 (CDR2).

SEQ ID NO: 3 is an amino acid sequence of complementarity determining region 3 of the heavy chain of 26/05-7D10-17-13 (CDR3).

SEQ ID NO: 4 is an amino acid sequence of complementarity determining region 1 of the light chain of 26/05-7D10-17-13 (CDR1).

SEQ ID NO: 5 is an amino acid sequence of complementarity determining region 2 of the light chain of 26/05-7D10-17-13 (CDR2).

SEQ ID NO: 6 is an amino acid sequence of complementarity determining region 3 of the light chain of 26/05-7D10-17-13 (CDR3).

SEQ ID NO: 7 is an amino acid sequence of the heavy chain variable region of 26/05-7D10-17-13 antibody.

SEQ ID NO: 8 is an amino acid sequence of the light chain variable region of 26/05-7D10-17-13 antibody.

SEQ ID NO: 9 is an amino acid sequence of an epitope within the α1-α2 loop of Bak that when bound by a Bak binding protein changes the conformation of Bak from a non-activated to an activated conformation.

SEQ ID NO: 10 is an amino acid sequence of an epitope within the α1-α2 loop of Bak that when bound by a Bak binding protein changes the conformation of Bak from a non-activated to an activated conformation.

SEQ ID NO: 11 is a DNA sequence encoding the heavy chain variable region of 26/05-7D10-17-13.

SEQ ID NO: 12 is a DNA sequence encoding the light chain variable region of 26/05-7D10-17-13.

SEQ ID NO: 13 is a mutated amino acid sequence of an epitope within the α1-α2 loop of Bak.

SEQ ID NO: 14 is a mutated amino acid sequence of an epitope within the α1-α2 loop of Bak.

SEQ ID NO: 15 is a mutated amino acid sequence of an epitope within the α1-α2 loop of Bak.

SEQ ID NO: 16 is a mutated amino acid sequence of an epitope within the α1-α2 loop of Bak.

SEQ ID NO: 17 is a Drosophila penetratin targeting sequence.

SEQ ID NO: 18 is a G317-2 Bak binding region.

SEQ ID NO: 19 is a refined G317-2 Bak binding region.

SEQ ID NO: 20 is a Ab-1 and Ab-2 binding peptide.

SEQ ID NO: 21 is a loop peptide bound by 26/05-7D10-17-13.

SEQ ID NO: 22 is a Bim BH3 peptide.

DETAILED DESCRIPTION

General

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or groups of compositions of matter.

Those skilled in the art will appreciate that the present disclosure is susceptible to variations and modifications other than those specifically described. It is to be understood that the disclosure includes all such variations and modifications. The disclosure also includes all of the steps, features, compositions and compounds referred to or indicated in this specification, individually or collectively, and any and all combinations or any two or more of said steps or features.

The present disclosure is not to be limited in scope by the specific examples described herein, which are intended for the purpose of exemplification only. Functionally-equivalent products, compositions and methods are clearly within the scope of the present disclosure.

Any example of the present disclosure herein shall be taken to apply mutatis mutandis to any other example of the disclosure unless specifically stated otherwise.

Unless specifically defined otherwise, all technical and scientific terms used herein shall be taken to have the same meaning as commonly understood by one of ordinary skill in the art (for example, in cell culture, molecular genetics, immunology, immunohistochemistry, protein chemistry, and biochemistry).

Unless otherwise indicated, the recombinant protein, cell culture, and immunological techniques utilized in the present disclosure are standard procedures, well known to those skilled in the art. Such techniques are described and explained throughout the literature in sources such as, J. Perbal, A Practical Guide to Molecular Cloning, John Wiley and Sons (1984), J. Sambrook et al. Molecular Cloning: A Laboratory Manual, Cold Spring Harbor Laboratory Press (1989), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), and F. M. Ausubel et al. (editors), Current Protocols in Molecular Biology, Greene Pub. Associates and Wiley-Interscience (1988, including all updates until present), Ed Harlow and David Lane (editors) Antibodies: A Laboratory Manual, Cold Spring Harbor Laboratory, (1988), and J. E. Coligan et al. (editors) Current Protocols in Immunology, John Wiley & Sons (including all updates until present).

The description and definitions of variable regions and parts thereof, immunoglobulins, antibodies and fragments thereof herein may be further clarified by the discussion in Kabat Sequences of Proteins of Immunological Interest, National Institutes of Health, Bethesda, Md., 1987 and 1991, Bork et al., J Mol. Biol. 242, 309-320, 1994, Chothia and Lesk J. Mol Biol. 196:901-917, 1987, Chothia et al. Nature 342, 877-883, 1989 and/or or Al-Lazikani et al., J Mol Biol 273, 927-948, 1997.

The term "and/or", e.g., "X and/or Y" shall be understood to mean either "X and Y" or "X or Y" and shall be taken to provide explicit support for both meanings or for either meaning.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

As used herein the term "derived from" shall be taken to indicate that a specified integer may be obtained from a particular source albeit not necessarily directly from that source.

Selected Definitions

For the purposes of nomenclature only and not limitation, the amino acid sequence of a Bak is taught in NCBI RefSeq NP 001179.1 (SwissProt Accession No. Q16611.1). In one example, Bak is human Bak. The structure of non-activated Bak comprises 9 α-helices (α1-α9) that form a tight bundle with a surface hydrophobic groove and a buried BH3 domain.

Bak activation during apoptosis involves a change in the conformation of Bak from the "non-activated" conformation to several "activated" states. In the context of the present disclosure the terms "activated Bak" or "activated conformation" refer to a Bak conformation that promotes apoptosis of a cell or population of cells. In contrast, the terms "non-activated Bak" or a "non-activated conformation" refer to a Bak conformation that does not promote apoptosis, or restricts or inhibits apoptosis of a cell or population of cells. It is envisaged that the binding proteins of the present disclosure can bind Bak and upon binding change the conformation of Bak. In one example, such binding proteins can change the conformation of Bak from a non-activated to an activated conformation. In one example, binding proteins can change the conformation of Bak from a non-activated to an activated conformation by binding to an epitope within the α1-α2 loop of Bak.

Accordingly, Bak binding proteins of the present disclosure have an antigen binding domain that recognise an epitope within the α1-α2 loop of Bak. In one example, the antigen binding domain recognises an epitope within the α1-α2 loop of Bak comprising a sequence at least about 70% or 80% or 85% or 86% or 90% or 95% or 99% or 100% identical to a sequence set forth in SEQ ID NO: 9.

In one example, the antigen binding domain recognises an epitope within the α1-α2 loop of Bak comprising a sequence at least about 70% or 80% or 85% or 86% or 90% or 95% or 99% or 100% identical to a sequence set forth in SEQ ID NO: 10.

For example, the Bak binding protein binds to one or more or all of the following mutant polypeptides:
    (i) a mutant polypeptide comprising a sequence set forth in SEQ ID NO: 13 (P55X variant), wherein X is any other amino acid;
    (ii) a mutant polypeptide comprising a sequence set forth in SEQ ID NO: 14 (P55C variant) that has not been oligmerised by tBid;
    (iii) a mutant polypeptide comprising a sequence set forth in SEQ ID NO: 14 (P55C variant) that has been oligmerised by tBid;
    (iv) a mutant polypeptide comprising a sequence set forth in SEQ ID NO: 15 (G51X variant) wherein X is any other amino acid; or
    (v) a mutant polypeptide comprising a sequence set forth in SEQ ID NO: 16 (G51C variant) that has not been oligmerised by tBid;
at a level that is reduced compared to the level of binding of the Bak binding protein to a polypeptide comprising a sequence set forth in SEQ ID NO: 9 or SEQ ID NO: 10.

In one example, the antigen binding domain recognises an epitope within the α1-α2 loop of Bak having a sequence identical to the sequence set forth in SEQ ID NO: 10.

The term "immunoglobulin" will be understood to include any antigen binding protein comprising an immunoglobulin domain. Exemplary immunoglobulins are antibodies. Additional proteins encompassed by the term "immunoglobulin" include domain antibodies, camelid antibodies and antibodies from cartilaginous fish (i.e., immunoglobulin new antigen receptors (IgNARs)). Generally, camelid antibodies and IgNARs comprise a $V_H$, however lack a $V_L$ and are often referred to as heavy chain immunoglobulins. Other "immunoglobulins" include T cell receptors.

The skilled artisan will be aware that an "antibody" is generally considered to be a protein that comprises a variable region made up of a plurality of polypeptide chains, e.g., a polypeptide comprising a $V_L$ and a polypeptide comprising a $V_H$. An antibody also generally comprises constant domains, some of which can be arranged into a constant region or constant fragment or fragment crystallizable (Fc). A $V_H$ and a $V_L$ interact to form a Fv comprising an antigen binding region that specifically binds to one or a few closely related antigens. Generally, a light chain from mammals is either κ light chain or a λ light chain and a heavy chain from mammals is α, δ, ε, γ, or μ. Antibodies can be of any type (e.g., IgG, IgE, IgM, IgD, IgA, and IgY), class (e.g., IgG1, IgG2, IgG3, IgG4, IgA1 and IgA2) or subclass. The term "antibody" also encompasses humanized antibodies, primatized antibodies, human antibodies and chimeric antibodies.

The terms "full-length antibody", "intact antibody" or "whole antibody" are used interchangeably to refer to an antibody in its substantially intact form, as opposed to an antigen binding fragment of an antibody. Specifically, whole antibodies include those with heavy and light chains including an Fc region. The constant domains may be wild-type sequence constant domains (e.g., human wild-type sequence constant domains) or amino acid sequence variants thereof.

The term "naked antibody" refers to an antibody that is not conjugated to another compound, e.g., a toxic compound or radiolabel.

In one example, the antibodies of the present disclosure are "naked" antibodies. Put another way, the antibodies of the present disclosure may be un-conjugated antibodies.

An "antigen binding fragment" of an antibody comprises one or more variable regions of an intact antibody. Examples of antibody fragments include Fab, Fab', F(ab')2 and Fv fragments; diabodies; linear antibodies; single-chain antibody molecules and multispecific antibodies formed from antibody fragments. Such fragments can be produced via various methods known in the art. For example, Fab encompassed by the present disclosure can be produced by the methods described in Example 15 below.

As used herein, "variable region" refers to the portions of the light and/or heavy chains of an antibody as defined herein that specifically binds to an antigen and, for example, includes amino acid sequences of CDRs; i.e., CDR1, CDR2, and CDR3, and framework regions (FRs). For example, the variable region comprises three or four FRs (e.g., FR1, FR2, FR3 and optionally FR4) together with three CDRs. $V_H$ refers to the variable region of the heavy chain. $V_L$ refers to the variable region of the light chain.

As used herein, the term "complementarity determining regions" (syn. CDRs; i.e., CDR1, CDR2, and CDR3) refers to the amino acid residues of an antibody variable region the presence of which are major contributors to specific antigen binding. Each variable region typically has three CDR regions identified as CDR1, CDR2 and CDR3. In one example, the amino acid positions assigned to CDRs and FRs are defined according to Kabat Sequences of Proteins of Immunological Interest, National Institutes of Health, Bethesda, Md., 1987 and 1991 (also referred to herein as "the Kabat numbering system".

"Framework regions" (Syn. FR) are those variable domain residues other than the CDR residues.

The term "constant region" as used herein, refers to a portion of heavy chain or light chain of an antibody other than the variable region. In a heavy chain, the constant region generally comprises a plurality of constant domains and a hinge region, e.g., a IgG constant region comprises the following linked components, a constant heavy (CH)1, a linker, a CH2 and a CH3. In a heavy chain, a constant region comprises a Fc. In a light chain, a constant region generally comprise one constant domain (a CL1).

The term "fragment crystalizable" or "Fc" or "Fc region" or "Fc portion" (which can be used interchangeably herein) refers to a region of an antibody comprising at least one constant domain and which is generally (though not necessarily) glycosylated and which is capable of binding to one or more Fc receptors and/or components of the complement cascade. The heavy chain constant region can be selected from any of the five isotypes: α, δ, ε, γ, or μ. Exemplary heavy chain constant regions are gamma 1 (IgG1), gamma 2 (IgG2) and gamma 3 (IgG3), or hybrids thereof.

A "constant domain" is a domain in an antibody the sequence of which is highly similar in antibodies/antibodies of the same type, e.g., IgG or IgM or IgE. A constant region of an antibody generally comprises a plurality of constant domains, e.g., the constant region of γ, α δ heavy chain comprises two constant domains.

The term "EU numbering system of Kabat" will be understood to mean the numbering of an antibody heavy chain is according to the EU index as taught in Kabat et al., 1991, Sequences of Proteins of Immunological Interest, 5th Ed., United States Public Health Service, National Institutes of Health, Bethesda. The EU index is based on the residue numbering of the human IgG1 EU antibody.

As used herein, the term "binds" in reference to the interaction of a binding protein with an antigen means that the interaction is dependent upon the presence of a particular structure (e.g., an antigenic determinant or epitope) on the antigen. For example, a compound, such as an antibody, recognizes and binds to a specific protein structure rather than to proteins generally. If a binding protein binds to epitope "A", the presence of a molecule containing epitope "A" (or free, unlabeled "A"), in a reaction containing labeled "A" and the binding protein, will reduce the amount of labeled "A" bound to the binding protein.

As used herein, the term "specifically binds" shall be taken to mean that the binding interaction between an antibody or antigen binding fragment thereof and Bak chain is dependent on the presence of the antigenic determinant or epitope of an Bak chain bound by the antibody or antigen binding fragment thereof. Accordingly, the antibody or antigen binding fragment thereof preferentially binds or recognizes an Bak chain antigenic determinant or epitope even when present in a mixture of other molecules or organisms. In one example, the antibody or antigen binding fragment thereof reacts or associates more frequently, more rapidly, with greater duration and/or with greater affinity with Bak or cell expressing same than it does with alternative antigens or cells. It is also understood by reading this definition that, for example, an antibody or antigen binding fragment thereof specifically binds to Bak may or may not specifically bind to a second antigen. As such, "specific binding" does not necessarily require exclusive binding or non-detectable binding of another antigen. The term "specifically binds" can be used interchangeably with "selectively binds" herein. Generally, reference herein to binding means specific binding, and each term shall be understood to provide explicit support for the other term. Methods for determining specific binding will be apparent to the skilled person. For example, a binding protein of the disclosure is contacted with Bak or a cell expressing same or a mutant form thereof or an alternative antigen. The binding of the binding protein to the Bak or mutant form or alternative antigen is then determined and a binding protein that binds as set out above to the Bak rather than the mutant or alternative antigen is considered to specifically bind to Bak.

As used herein, the term "treatment" refers to clinical intervention designed to alter the natural course of the individual or cell being treated during the course of clinical pathology. Desirable effects of treatment include decreasing the rate of disease progression, ameliorating or palliating the disease state, and remission or improved prognosis. An individual is successfully "treated", for example, if one or more symptoms associated with a disease are mitigated or eliminated.

As used herein, the term "prevention" includes providing prophylaxis with respect to occurrence or recurrence of a disease in an individual. An individual may be predisposed to or at risk of developing the disease or disease relapse but has not yet been diagnosed with the disease or the relapse.

An "effective amount" refers to at least an amount effective, at dosages and for periods of time necessary, to achieve the desired therapeutic or prophylactic result. An effective amount can be provided in one or more administrations. In some examples of the present disclosure, the term "effective amount" is meant an amount necessary to effect treatment of a disease or condition as hereinbefore described. The effective amount may vary according to the disease or condition to be treated and also according to the weight, age, racial background, sex, health and/or physical condition and other factors relevant to the mammal being treated. Typically, the effective amount will fall within a relatively broad range (e.g. a "dosage" range) that can be determined through routine trial and experimentation by a medical practitioner. The effective amount can be administered in a single dose or in a dose repeated once or several times over a treatment period.

A "therapeutically effective amount" is at least the minimum concentration required to effect a measurable improvement of a particular disorder (e.g. cancer). A therapeutically effective amount herein may vary according to factors such as the disease state, age, sex, and weight of the patient, and the ability of the binding protein (e.g., antibody or antigen binding fragment thereof) to elicit a desired response in the individual. A therapeutically effective amount is also one in which any toxic or detrimental effects of the antibody or antigen binding fragment thereof are outweighed by the therapeutically beneficial effects. In the case of cancer, the therapeutically effective amount of the binding protein may reduce the number of cancer cells; reduce the primary tumor size; inhibit (i.e., slow to some extent and, in some examples, stop) cancer cell infiltration into peripheral organs; inhibit (i.e., slow to some extent and, in some examples, stop) tumor metastasis; inhibit or delay, to some extent, tumor growth or tumor progression; and/or relieve to some extent one or more of the symptoms associated with the disorder. To the extent the binding protein may prevent growth and/or kill existing cancer cells, it may be cytostatic and/or cytotoxic. For cancer therapy, efficacy in vivo can, for example, be measured by assessing the duration of survival, time to disease progression (TTP), the response rates (RR), duration of response, and/or quality of life.

The "mammal" treated according to the present disclosure may be a mammal, such as a non-human primate or a human. In one example, the mammal is a human.

Antibodies

Immunization-Based Methods

Methods for generating antibodies are known in the art and/or described in Harlow and Lane (editors) Antibodies: A Laboratory Manual, Cold Spring Harbor Laboratory, (1988). Generally, in such methods an Bak binding protein or immunogenic fragment or epitope thereof or a cell expressing and displaying same (i.e., an immunogen), optionally formulated with any suitable or desired carrier, adjuvant, or pharmaceutically acceptable excipient, is administered to a non-human animal, for example, a mouse, chicken, rat, rabbit, guinea pig, dog, horse, cow, goat or pig. The immunogen may be administered intranasally, intramuscularly, sub-cutaneously, intravenously, intradermally, intraperitoneally, or by other known route.

The production of polyclonal antibodies may be monitored by sampling blood of the immunized animal at various points following immunization. One or more further immunizations may be given, if required to achieve a desired antibody titer. The process of boosting and titering is repeated until a suitable titer is achieved. When a desired level of immunogenicity is obtained, the immunized animal is bled and the serum isolated and stored, and/or the animal is used to generate monoclonal antibodies (Mabs).

Monoclonal antibodies are one exemplary form of antibody contemplated by the present disclosure. The term "monoclonal antibody" or "MAb" refers to a homogeneous antibody population capable of binding to the same antigen (s), for example, to the same epitope within the antigen. This term is not intended to be limited as regards to the source of the antibody or the manner in which it is made.

For the production of Mabs any one of a number of known techniques may be used, such as, for example, the procedure exemplified in U.S. Pat. No. 4,196,265 or Harlow and Lane (1988), supra.

For example, a suitable animal is immunized with an immunogen under conditions sufficient to stimulate antibody producing cells. Rodents such as rabbits, mice and rats are exemplary animals. Mice genetically-engineered to express human immunoglobulin proteins and, for example, do not express murine immunoglobulin proteins, can also be used to generate an antibody of the present disclosure (e.g., as described in WO2002/066630). Following immunization, somatic cells with the potential for producing antibodies, specifically B lymphocytes (B cells), are selected for use in the mAb generating protocol. These cells may be obtained from biopsies of spleens, tonsils or lymph nodes, or from a peripheral blood sample. The B cells from the immunized animal are then fused with cells of an immortal myeloma cell, generally derived from the same species as the animal that was immunized with the immunogen.

Hybrids are amplified by culture in a selective medium comprising an agent that blocks the de novo synthesis of nucleotides in the tissue culture media. Exemplary agents are aminopterin, methotrexate and azaserine.

The amplified hybridomas are subjected to a functional selection for antibody specificity and/or titer, such as, for example, by flow cytometry and/or immunohistochemstry and/or immunoassay (e.g. radioimmunoassay, enzyme immunoassay, cytotoxicity assay, plaque assay, dot immunoassay, and the like).

Alternatively, ABL-MYC technology (NeoClone, Madison Wis. 53713, USA) is used to produce cell lines secreting MAbs (e.g., as described in Largaespada et al, J. Immunol. Methods. 197: 85-95, 1996).

Library-Based Methods

The present disclosure also encompasses screening of libraries of antibodies or antigen binding fragments thereof (e.g., comprising variable regions thereof).

Examples of libraries contemplated by this disclosure include naïve libraries (from unchallenged subjects), immunized libraries (from subjects immunized with an antigen) or synthetic libraries. Nucleic acid encoding antibodies or regions thereof (e.g., variable regions) are cloned by conventional techniques (e.g., as disclosed in Sambrook and Russell, eds, Molecular Cloning: A Laboratory Manual, 3rd Ed, vols. 1-3, Cold Spring Harbor Laboratory Press, 2001)

and used to encode and display proteins using a method known in the art. Other techniques for producing libraries of proteins are described in, for example in U.S. Pat. No. 6,300,064 (e.g., a HuCAL library of Morphosys AG); U.S. Pat. No. 5,885,793; 6,204,023; 6,291,158; or 6,248,516.

The antigen binding fragments according to the disclosure may be soluble secreted proteins or may be presented as a fusion protein on the surface of a cell, or particle (e.g., a phage or other virus, a ribosome or a spore). Various display library formats are known in the art. For example, the library is an in vitro display library (e.g., a ribosome display library, a covalent display library or a mRNA display library, e.g., as described in U.S. Pat. No. 7,270,969). In yet another example, the display library is a phage display library wherein proteins comprising antigen binding fragments of antibodies are expressed on phage, e.g., as described in U.S. Pat. No. 6,300,064; 5,885,793; 6,204,023; 6,291,158; or 6,248,516. Other phage display methods are known in the art and are contemplated by the present disclosure. Similarly, methods of cell display are contemplated by the disclosure, e.g., bacterial display libraries, e.g., as described in U.S. Pat. No. 5,516,637; yeast display libraries, e.g., as described in U.S. Pat. No. 6,423,538 or a mammalian display library.

Methods for screening display libraries are known in the art. In one example, a display library of the present disclosure is screened using affinity purification, e.g., as described in Scopes (In: Protein purification: principles and practice, Third Edition, Springer Verlag, 1994). Methods of affinity purification typically involve contacting proteins comprising antigen binding fragments displayed by the library with a target antigen (e.g., Bak) and, following washing, eluting those domains that remain bound to the antigen.

Any variable regions or scFvs identified by screening are readily modified into a complete antibody, if desired. Exemplary methods for modifying or reformatting variable regions or scFvs into a complete antibody are described, for example, in Jones et al., J Immunol Methods. 354:85-90, 2010; or Jostock et al., J Immunol Methods, 289: 65-80, 2004; or WO2012/040793. Alternatively, or additionally, standard cloning methods are used, e.g., as described in Ausubel et al (In: Current Protocols in Molecular Biology. Wiley Interscience, ISBN 047 150338, 1987), and/or (Sambrook et al (In: Molecular Cloning: Molecular Cloning: A Laboratory Manual, Cold Spring Harbor Laboratories, New York, Third Edition 2001).

Deimmunized, Chimeric, Humanized, Synhumanized, Primatized and Human Antibodies or Antigen Binding Fragments The antibodies or antigen binding fragments of the present disclosure may be may be humanized.

The term "humanized antibody" shall be understood to refer to a protein comprising a human-like variable region, which includes CDRs from an antibody from a non-human species (e.g., mouse or rat or non-human primate) grafted onto or inserted into FRs from a human antibody (this type of antibody is also referred to a "CDR-grafted antibody"). Humanized antibodies also include antibodies in which one or more residues of the human protein are modified by one or more amino acid substitutions and/or one or more FR residues of the human antibody are replaced by corresponding non-human residues. Humanized antibodies may also comprise residues which are found in neither the human antibody or in the non-human antibody. Any additional regions of the antibody (e.g., Fc region) are generally human. Humanization can be performed using a method known in the art, e.g., U.S. Pat. No. 5,225,539, 6,054,297, 7,566,771 or 5,585,089. The term "humanized antibody" also encompasses a super-humanized antibody, e.g., as described in U.S. Pat. No. 7,732,578. A similar meaning will be taken to apply to the term "humanized antigen binding fragment".

The antibodies or antigen binding fragments thereof of the present disclosure may be human antibodies or antigen binding fragments thereof. The term "human antibody" as used herein refers to antibodies having variable and, optionally, constant antibody regions found in humans, e.g. in the human germline or somatic cells or from libraries produced using such regions. The "human" antibodies can include amino acid residues not encoded by human sequences, e.g. mutations introduced by random or site directed mutations in vitro (in particular mutations which involve conservative substitutions or mutations in a small number of residues of the protein, e.g. in 1, 2, 3, 4 or 5 of the residues of the protein). These "human antibodies" do not necessarily need to be generated as a result of an immune response of a human, rather, they can be generated using recombinant means (e.g., screening a phage display library) and/or by a transgenic animal (e.g., a mouse) comprising nucleic acid encoding human antibody constant and/or variable regions and/or using guided selection (e.g., as described in or U.S. Pat. No. 5,565,332). This term also encompasses affinity matured forms of such antibodies. For the purposes of the present disclosure, a human antibody will also be considered to include a protein comprising FRs from a human antibody or FRs comprising sequences from a consensus sequence of human FRs and in which one or more of the CDRs are random or semi-random, e.g., as described in U.S. Pat. No. 6,300,064 and/or U.S. Pat. No. 6,248,516. A similar meaning will be taken to apply to the term "human antigen binding fragment".

The antibodies or antigen binding fragments thereof of the present disclosure may be synhumanized antibodies or antigen binding fragments thereof. The term "synhumanized antibody" refers to an antibody prepared by a method described in WO2007/019620. A synhumanized antibody includes a variable region of an antibody, wherein the variable region comprises FRs from a New World primate antibody variable region and CDRs from a non-New World primate antibody variable region.

The antibody or antigen binding fragment thereof of the present disclosure may be primatized. A "primatized antibody" comprises variable region(s) from an antibody generated following immunization of a non-human primate (e.g., a cynomolgus macaque). Optionally, the variable regions of the non-human primate antibody are linked to human constant regions to produce a primatized antibody. Exemplary methods for producing primatized antibodies are described in U.S. Pat. No. 6,113,898.

In one example an antibody or antigen binding fragment thereof of the disclosure is a chimeric antibody or fragment. The term "chimeric antibody" or "chimeric antigen binding fragment" refers to an antibody or fragment in which one or more of the variable domains is from a particular species (e.g., murine, such as mouse or rat) or belonging to a particular antibody class or subclass, while the remainder of the antibody or fragment is from another species (such as, for example, human or non-human primate) or belonging to another antibody class or subclass. In one example, a chimeric antibody comprising a $V_H$ and/or a $V_L$ from a non-human antibody (e.g., a murine antibody) and the remaining regions of the antibody are from a human antibody. The production of such chimeric antibodies and antigen binding fragments thereof is known in the art, and may be achieved by standard means (as described, e.g., in U.S. Pat. Nos. 6,331,415; 5,807,715; 4,816,567 and 4,816,397).

The present disclosure also contemplates a deimmunized antibody or antigen binding fragment thereof, e.g., as described in WO2000/34317 and WO2004/108158. Deimmunized antibodies and fragments have one or more epitopes, e.g., B cell epitopes or T cell epitopes removed (i.e., mutated) to thereby reduce the likelihood that a subject will raise an immune response against the antibody or protein. For example, an antibody of the disclosure is analyzed to identify one or more B or T cell epitopes and one or more amino acid residues within the epitope is mutated to thereby reduce the immunogenicity of the antibody.

Antibody Fragments
Single-Domain Antibodies

In some examples, an antigen binding fragment of an antibody of the disclosure is or comprises a single-domain antibody (which is used interchangeably with the term "domain antibody" or "dAb"). A single-domain antibody is a single polypeptide chain comprising all or a portion of the heavy chain variable domain of an antibody.

Diabodies, Triabodies, Tetrabodies

In some examples, an antigen binding fragment of the disclosure is or comprises a diabody, triabody, tetrabody or higher order protein complex such as those described in WO98/044001 and/or WO94/007921.

For example, a diabody is a protein comprising two associated polypeptide chains, each polypeptide chain comprising the structure $V_L$-X-$V_H$ or $V_H$-X-$V_L$, wherein X is a linker comprising insufficient residues to permit the $V_H$ and $V_L$ in a single polypeptide chain to associate (or form an Fv) or is absent, and wherein the $V_H$ of one polypeptide chain binds to a $V_L$ of the other polypeptide chain to form an antigen binding site, i.e., to form a Fv molecule capable of specifically binding to one or more antigens. The $V_L$ and $V_H$ can be the same in each polypeptide chain or the $V_L$ and $V_H$ can be different in each polypeptide chain so as to form a bispecific diabody (i.e., comprising two Fvs having different specificity).

Single Chain Fv (scFv) Fragments

The skilled artisan will be aware that scFvs comprise $V_H$ and $V_L$ regions in a single polypeptide chain and a polypeptide linker between the $V_H$ and $V_L$ which enables the scFv to form the desired structure for antigen binding (i.e., for the $V_H$ and $V_L$ of the single polypeptide chain to associate with one another to form a Fv). For example, the linker comprises in excess of 12 amino acid residues with (Gly4Ser)3 being one of the more favored linkers for a scFv.

The present disclosure also contemplates a disulfide stabilized Fv (or diFv or dsFv), in which a single cysteine residue is introduced into a FR of $V_H$ and a FR of $V_L$ and the cysteine residues linked by a disulfide bond to yield a stable Fv.

Alternatively, or in addition, the present disclosure encompasses a dimeric scFv, i.e., a protein comprising two scFv molecules linked by a non-covalent or covalent linkage, e.g., by a leucine zipper domain (e.g., derived from Fos or Jun). Alternatively, two scFvs are linked by a peptide linker of sufficient length to permit both scFvs to form and to bind to an antigen, e.g., as described in US20060263367.

Other Antibodies and Antibody Fragments

The present disclosure also contemplates other antibodies and antibody fragments, such as:
  (i) "key and hole" bispecific proteins as described in U.S. Pat. No. 5,731,168;
  (ii) heteroconjugate proteins, e.g., as described in U.S. Pat. No. 4,676,980;
  (iii) heteroconjugate proteins produced using a chemical cross-linker, e.g., as described in U.S. Pat. No. 4,676,980; and
  (iv) Fab$_3$ (e.g., as described in EP19930302894).

Immunoglobulins and Immunoglobulin Fragments

An example of a binding protein of the present disclosure is a protein (e.g., an antibody mimetic) comprising a variable region of an immunoglobulin, such as a T cell receptor or a heavy chain immunoglobulin (e.g., an IgNAR, a camelid antibody).

Heavy Chain Inununoglobulins

Heavy chain immunoglobulins differ structurally from many other forms of immunoglobulin (e.g., antibodies), in so far as they comprise a heavy chain, but do not comprise a light chain. Accordingly, these immunoglobulins are also referred to as "heavy chain only antibodies". Heavy chain immunoglobulins are found in, for example, camelids and cartilaginous fish (also called IgNAR).

The variable regions present in naturally occurring heavy chain immunoglobulins are generally referred to as "$V_H$ domains" in camelid Ig and V-NAR in IgNAR, in order to distinguish them from the heavy chain variable regions that are present in conventional 4-chain antibodies (which are referred to as "$V_H$ domains") and from the light chain variable regions that are present in conventional 4-chain antibodies (which are referred to as "$V_L$ domains").

Heavy chain immunoglobulins do not require the presence of light chains to bind with high affinity and with high specificity to a relevant antigen. This means that single domain binding fragments can be derived from heavy chain immunoglobulins, which are easy to express and are generally stable and soluble.

A general description of heavy chain immunoglobulins from camelids and the variable regions thereof and methods for their production and/or isolation and/or use is found inter alia in the following references WO94/04678, WO97/49805 and WO 97/49805.

A general description of heavy chain immunoglobulins from cartilaginous fish and the variable regions thereof and methods for their production and/or isolation and/or use is found inter alia in WO2005/118629.

V-Like Proteins

An example of a binding protein of the disclosure is a T-cell receptor. T cell receptors have two V-domains that combine into a structure similar to the Fv module of an antibody. Novotny et al., Proc Natl Acad Sci USA 88: 8646-8650, 1991 describes how the two V-domains of the T-cell receptor (termed alpha and beta) can be fused and expressed as a single chain polypeptide and, further, how to alter surface residues to reduce the hydrophobicity directly analogous to an antibody scFv. Other publications describing production of single-chain T-cell receptors or multimeric T cell receptors comprising two V-alpha and V-beta domains include WO1999/045110 or WO2011/107595.

Other non-antibody proteins comprising antigen binding domains include proteins with V-like domains, which are generally monomeric. Examples of proteins comprising such V-like domains include CTLA-4, CD28 and ICOS. Further disclosure of proteins comprising such V-like domains is included in WO1999/045110.

Adnectins

In one example, a binding protein of the disclosure is an adnectin. Adnectins are based on the tenth fibronectin type III (10Fn3) domain of human fibronectin in which the loop regions are altered to confer antigen binding. For example, three loops at one end of the β-sandwich of the 10Fn3 domain can be engineered to enable an Adnectin to specifically recognize an antigen. For further details see US20080139791 or WO2005/056764.

Anticalins

In a further example, a binding protein of the disclosure is an anticalin. Anticalins are derived from lipocalins, which are a family of extracellular proteins which transport small hydrophobic molecules such as steroids, bilins, retinoids and lipids. Lipocalins have a rigid β-sheet secondary structure with a plurality of loops at the open end of the conical structure which can be engineered to bind to an antigen. Such engineered lipocalins are known as anticalins. For further description of anticalins see U.S. Pat. No. 7,250, 297B1 or US20070224633.

Affibodies

In a further example, a binding protein of the disclosure is an affibody. An affibody is a scaffold derived from the Z domain (antigen binding domain) of Protein A of Staphylococcus aureus which can be engineered to bind to antigen. The Z domain consists of a three-helical bundle of approximately 58 amino acids. Libraries have been generated by randomization of surface residues. For further details see EP1641818.

Avimers

In a further example, a binding protein of the disclosure is an Avimer. Avimers are multidomain proteins derived from the A-domain scaffold family. The native domains of approximately 35 amino acids adopt a defined disulfide bonded structure. Diversity is generated by shuffling of the natural variation exhibited by the family of A-domains. For further details see WO2002088171.

DARPins

In a further example, a binding protein of the disclosure is a Designed Ankyrin Repeat Protein (DARPin). DARPins are derived from Ankyrin which is a family of proteins that mediate attachment of integral membrane proteins to the cytoskeleton. A single ankyrin repeat is a 33 residue motif consisting of two α-helices and a β-turn. They can be engineered to bind different target antigens by randomizing residues in the first α-helix and a β-turn of each repeat. Their binding interface can be increased by increasing the number of modules (a method of affinity maturation). For further details see US20040132028.

Other Non-Antibody Polypeptides

Other non-antibody proteins comprising binding domains include those based on human γ-crystallin and human ubiquitin (affilins), kunitz type domains of human protease inhibitors, PDZ-domains of the Ras-binding protein AF-6, scorpion toxins (charybdotoxin), C-type lectin domain (tetranectins).

Constant Regions

The present disclosure encompasses binding proteins (e.g., antibodies and antigen binding fragments thereof) comprising a constant region of an antibody and/or a Fc region of an antibody.

Sequences of constant regions and/or Fc regions useful for producing the immunoglobulins, antibodies or antigen binding fragments of the present disclosure may be obtained from a number of different sources. In some examples, the constant region, Fc or portion thereof of the binding protein is derived from a human antibody. The constant region, Fc or portion thereof may be derived from any antibody class, including IgA, IgM, IgG, IgD, IgA and IgE, and any antibody isotype, including IgG1, IgG2, IgG3 and IgG4. In one example, the constant region or Fc is human isotype IgG1 or human isotype IgG2 or human isotype IgG3 or a hybrid of any of the foregoing.

Stabilized Proteins

Neutralizing proteins of the present disclosure can comprise an IgG4 constant region or a stabilized IgG4 constant region. The term "stabilized IgG4 constant region" will be understood to mean an IgG4 constant region that has been modified to reduce Fab arm exchange or the propensity to undergo Fab arm exchange or formation of a half-antibody or a propensity to form a half antibody. "Fab arm exchange" refers to a type of protein modification for human IgG4, in which an IgG4 heavy chain and attached light chain (half-molecule) is swapped for a heavy-light chain pair from another IgG4 molecule. Thus, IgG4 molecules may acquire two distinct Fab arms recognizing two distinct antigens (resulting in bispecific molecules). Fab arm exchange occurs naturally in vivo and can be induced in vitro by purified blood cells or reducing agents such as reduced glutathione. A "half antibody" forms when an IgG4 antibody dissociates to form two molecules each containing a single heavy chain and a single light chain.

In one example, a stabilized IgG4 constant region comprises a proline at position 241 of the hinge region according to the system of Kabat (Kabat et al., Sequences of Proteins of Immunological Interest Washington D.C. United States Department of Health and Human Services, 1987 and/or 1991). This position corresponds to position 228 of the hinge region according to the EU numbering system (Kabat et al., Sequences of Proteins of Immunological Interest Washington D.C. United States Department of Health and Human Services, 2001 and Edelman et al., Proc. Natl. Acad. USA, 63, 78-85, 1969). In human IgG4, this residue is generally a serine. Following substitution of the serine for proline, the IgG4 hinge region comprises a sequence CPPC. In this regard, the skilled person will be aware that the "hinge region" is a proline-rich portion of an antibody heavy chain constant region that links the Fc and Fab regions that confers mobility on the two Fab arms of an antibody. The hinge region includes cysteine residues which are involved in inter-heavy chain disulfide bonds. It is generally defined as stretching from Glu226 to Pro243 of human IgG1 according to the numbering system of Kabat. Hinge regions of other IgG isotypes may be aligned with the IgG1 sequence by placing the first and last cysteine residues forming inter-heavy chain disulphide (S—S) bonds in the same positions (see for example WO2010/080538).

Additional Modifications

The present disclosure also contemplates additional modifications to constant regions or Fc regions of binding proteins (e.g., antibodies or antigen binding fragments).

For example, constant region of Fc region comprises one or more amino acid substitutions that increase the half-life of the antibody or fragment. For example, the constant region or Fc region comprises one or more amino acid substitutions that increase the affinity of the constant region or Fc region for the neonatal Fc region (FcRn). For example, the constant region or Fc region has increased affinity for FcRn at lower pH, e.g., about pH 6.0, to facilitate Fc/FcRn binding in an endosome. In one example, the constant region or Fc region has increased affinity for FcRn at about pH 6 compared to its affinity at about pH 7.4, which facilitates the re-release of constant region or Fc into blood following cellular recycling. These amino acid substitutions are useful for extending the half-life of a Fc containing or constant region containing binding protein, by reducing clearance from the blood.

Exemplary amino acid substitutions include T250Q and/or M428L according to the EU numbering system of Kabat. Additional or alternative amino acid substitutions are described, for example, in US20070135620.

Peptides

In one example, a binding molecule is a peptide, e.g., isolated from a random peptide library. To identify a suitable peptide, a random peptide library is generated and screened as described in U.S. Pat. Nos. 5,733,731, 5,591,646 and 5,834,318. Generally, such libraries are generated from short random oligonucleotides that are expressed either in vitro or in vivo and displayed in such a way to facilitate screening of the library to identify a peptide that. is capable of specifically binding to an antigen described herein. Methods of display include, phage display, retroviral display, bacterial surface display, bacterial flagellar display, bacterial spore display, yeast surface display, mammalian surface display, and methods of in vitro display including, mRNA display, ribosome display and covalent display.

A peptide that is capable of binding an antigen described herein is identified by any of a number of methods known in the art, such as, for example, standard affinity purification methods as described, for example in Scopes, 1994) purification using FACS analysis as described in U.S. Pat. No. 645,563.

Protein Production
Recombinant Expression

In one example, a binding protein as described herein is a peptide or polypeptide (e.g., is an antibody or antigen binding fragment thereof). In one example, the binding protein is recombinant.

In the case of a recombinant peptide or polypeptide, nucleic acid encoding same can be cloned into expression vectors, which are then transfected into host cells, such as *E. coli* cells, yeast cells, insect cells, or mammalian cells, such as simian COS cells, Chinese Hamster Ovary (CHO) cells, human embryonic kidney (HEK) cells, or myeloma cells that do not otherwise produce immunoglobulin or antibody protein.

Exemplary cells used for expressing a peptide or polypeptide are CHO cells, myeloma cells or HEK cells. The cell may further comprise one or more genetic mutations and/or deletions that facilitate expression of a peptide or polypeptide (e.g., antibody or antigen binding fragment thereof). One non-limiting example is a deletion of a gene encoding an enzyme required for fucosylation of an expressed peptide or polypeptide (e.g., comprising a Fc region of an antibody). For example, the deleted gene encodes FUT8. A commercially available source of FUT8-deleted CHO cells is Biowa (Potelligent™ cells). For example, the cells used for expression of an afucosylated peptide or polypeptide are FUT8-deleted CHO cells, such as, Biowa's Potelligent™ cells. Molecular cloning techniques to achieve these ends are known in the art and described, for example in Ausubel et al., (editors), Current Protocols in Molecular Biology, Greene Pub. Associates and Wiley-Interscience (1988, including all updates until present) or Sambrook et al., Molecular Cloning: A Laboratory Manual, Cold Spring Harbor Laboratory Press (1989). A wide variety of cloning and in vitro amplification methods are suitable for the construction of recombinant nucleic acids. Methods of producing recombinant antibodies are also known in the art. See U.S. Pat. No. 4,816,567 or 5,530,101.

Following isolation, the nucleic acid is inserted operably linked to a promoter in an expression construct or expression vector for further cloning (amplification of the DNA) or for expression in a cell-free system or in cells. Thus, another example of the disclosure provides an expression construct that comprises an isolated nucleic acid of the disclosure and one or more additional nucleotide sequences. Suitably, the expression construct is in the form of, or comprises genetic components of, a plasmid, bacteriophage, a cosmid, a yeast or bacterial artificial chromosome as are understood in the art. Expression constructs may be suitable for maintenance and propagation of the isolated nucleic acid in bacteria or other host cells, for manipulation by recombinant DNA technology and/or for expression of the nucleic acid or a binding protein of the disclosure.

As used herein, the term "promoter" is to be taken in its broadest context and includes the transcriptional regulatory sequences of a genomic gene, including the TATA box or initiator element, which is required for accurate transcription initiation, with or without additional regulatory elements (e.g., upstream activating sequences, transcription factor binding sites, enhancers and silencers) that alter expression of a nucleic acid. e.g., in response to a developmental and/or external stimulus, or in a tissue specific manner. In the present context, the term "promoter" is also used to describe a recombinant, synthetic or fusion nucleic acid, or derivative which confers, activates or enhances the expression of a nucleic acid to which it is operably linked. Exemplary promoters can contain additional copies of one or more specific regulatory elements to further enhance expression and/or alter the spatial expression and/or temporal expression of said nucleic acid.

As used herein, the term "operably linked to" means positioning a promoter relative to a nucleic acid such that expression of the nucleic acid is controlled by the promoter.

Many vectors for expression in cells are available. The vector components generally include, but are not limited to, one or more of the following: a signal sequence, a sequence encoding the binding protein (e.g., derived from the information provided herein), an enhancer element, a promoter, and a transcription termination sequence. Exemplary signal sequences include prokaryotic secretion signals (e.g., pelB, alkaline phosphatase, penicillinase, Ipp, or heat-stable enterotoxin II), yeast secretion signals (e.g., invertase leader, a factor leader, or acid phosphatase leader) or mammalian secretion signals (e.g., herpes simplex gD signal).

Exemplary promoters active in mammalian cells include cytomegalovirus immediate early promoter (CMV-IE), human elongation factor 1-α promoter (EF1), small nuclear RNA promoters (U1a and U1b), α-myosin heavy chain promoter, Simian virus 40 promoter (SV40), Rous sarcoma virus promoter (RSV), Adenovirus major late promoter, β-actin promoter; hybrid regulatory element comprising a CMV enhancer/β-actin promoter or an immunoglobulin or antibody promoter or active fragment thereof. Examples of useful mammalian host cell lines are monkey kidney CV1 line transformed by SV40 (COS-7, ATCC CRL 1651); human embryonic kidney line (293 or 293 cells subcloned for growth in suspension culture; baby hamster kidney cells (BHK, ATCC CCL 10); or Chinese hamster ovary cells (CHO).

Typical promoters suitable for expression in yeast cells such as for example a yeast cell selected from the group comprising *Pichia pastoris, Saccharomyces cerevisiae* and *S. pombe*, include, but are not limited to, the ADH1 promoter, the GAL1 promoter, the GAL4 promoter, the CUP1 promoter, the PHO5 promoter, the nmt promoter, the RPR1 promoter, or the TEF1 promoter.

Means for introducing the isolated nucleic acid or expression construct comprising same into a cell for expression are known to those skilled in the art. The technique used for a given cell depends on the known successful techniques. Means for introducing recombinant DNA into cells include microinjection, transfection mediated by DEAE-dextran, transfection mediated by liposomes such as by using lipofectamine (Gibco, Md., USA) and/or cellfectin (Gibco, Md., USA), PEG-mediated DNA uptake, electroporation and microparticle bombardment such as by using DNA-coated tungsten or gold particles (Agracetus Inc., Wis., USA) amongst others.

The host cells used to produce the binding protein (e.g., antibody or antigen binding fragment) may be cultured in a variety of media, depending on the cell type used. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing mammalian cells. Media for culturing other cell types discussed herein are known in the art.

The skilled artisan will understand from the foregoing description that the present disclosure also provides an isolated nucleic acid encoding a binding protein (e.g., a peptide or polypeptide binding protein or an antibody or antigen binding fragment thereof) of the present disclosure. For example, a nucleic acid comprising the sequences set forth in SEQ ID NO: 11 and SEQ ID NO: 12.

The present disclosure also provides an expression construct comprising an isolated nucleic acid of the disclosure operably linked to a promoter. In one example, the expression construct is an expression vector.

In one example, the expression construct of the disclosure comprises a nucleic acid encoding a polypeptide (e.g., comprising a $V_H$) operably linked to a promoter and a nucleic acid encoding another polypeptide (e.g., comprising a $V_L$) operably linked to a promoter.

In another example, the expression construct is a bicistronic expression construct, e.g., comprising the following operably linked components in 5' to 3' order:
(i) a promoter
(ii) a nucleic acid encoding a first polypeptide;
(iii) an internal ribosome entry site; and
(iv) a nucleic acid encoding a second polypeptide.

For example, the first polypeptide comprises a $V_H$ and the second polypeptide comprises a $V_L$, or the first polypeptide comprises a $V_L$ and the second polypeptide comprises a $V_H$.

The present disclosure also contemplates separate expression constructs one of which encodes a first polypeptide (e.g., comprising a $V_H$) and another of which encodes a second polypeptide (e.g., comprising a $V_L$). For example, the present disclosure also provides a composition comprising:
(i) a first expression construct comprising a nucleic acid encoding a polypeptide (e.g., comprising a $V_H$) operably linked to a promoter; and
(ii) a second expression construct comprising a nucleic acid encoding a polypeptide (e.g., comprising a $V_L$) operably linked to a promoter.

The disclosure also provides a host cell comprising an expression construct according to the present disclosure.

The present disclosure also provides an isolated cell expressing a binding protein (e.g., a peptide or polypeptide binding protein or an antibody or antigen binding fragment thereof of the disclosure or a recombinant cell genetically-modified to express the binding protein.

In one example, the cell comprises the expression construct of the disclosure or:
(i) a first genetic construct comprising a nucleic acid encoding a polypeptide (e.g., comprising a $V_H$) operably linked to a promoter; and
(ii) a second genetic construct comprising a nucleic acid encoding a polypeptide (e.g., comprising a $V_L$) operably linked to a promoter, wherein the first and second polypeptides form an antibody or antigen binding fragment of the present disclosure.

The genetic construct can be integrated into the cell or remain episomal.

Examples of cells of the present disclosure include bacterial cells, yeast cells, insect cells or mammalian cells.

The present disclosure additionally provides a method for producing a binding protein (e.g., a peptide or polypeptide binding protein or an antibody or antigen binding fragment thereof) of the disclosure, the method comprising maintaining the genetic construct(s) of the disclosure under conditions sufficient for the binding protein to be produced.

In one example, the method for producing a binding protein of the disclosure comprises culturing the cell of the disclosure under conditions sufficient for the binding protein to be produced and, optionally, secreted.

In one example, the method for producing a binding protein of the disclosure additionally comprises isolating the binding protein thereof.

In one example, a method for producing a binding protein of the disclosure additionally comprises formulating the binding protein with a pharmaceutically acceptable carrier.

Isolation of Proteins

Methods for purifying a peptide or polypeptide (e.g., an antibody or antigen binding fragment) are known in the art and/or described herein.

Where a peptide or polypeptide is secreted into the medium, supernatants from such expression systems can be first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The peptide or polypeptide prepared from cells can be purified using, for example, ion exchange, hydroxyapatite chromatography, hydrophobic interaction chromatography, gel electrophoresis, dialysis, affinity chromatography (e.g., protein A affinity chromatography or protein G chromatography), or any combination of the foregoing. These methods are known in the art and described, for example in WO99/57134 or Ed Harlow and David Lane (editors) Antibodies: A Laboratory Manual, Cold Spring Harbor Laboratory, (1988).

Peptide Synthesis

A peptide is synthesized using a chemical method known to the skilled artisan. For example, synthetic peptides are prepared using known techniques of solid phase, liquid phase, or peptide condensation, or any combination thereof, and can include natural and/or unnatural amino acids. Amino acids used for peptide synthesis may be standard Boc (Nα-amino protected Nα-t-butyloxycarbonyl) amino acid resin with the deprotecting, neutralization, coupling and wash protocols of the original solid phase procedure of Merrifield, *J. Am. Chem. Soc.,* 85:2149-2154, 1963, or the base-labile Nα-amino protected 9-fluorenylmethoxycarbonyl (Fmoc) amino acids described by Carpino and Han, *J. Org. Chem.,* 37:3403-3409, 1972. Both Fmoc and Boc Na-amino protected amino acids can be obtained from various commercial sources, such as, for example, Fluka, Bachem, Advanced Chemtech, Sigma, Cambridge Research Biochemical, Bachem, or Peninsula Labs.

Generally, chemical synthesis methods comprise the sequential addition of one or more amino acids to a growing peptide chain. Normally, either the amino or carboxyl group of the first amino acid is protected by a suitable protecting group. The protected or derivatized amino acid can then be either attached to an inert solid support or utilized in solution by adding the next amino acid in the sequence having the complementary (amino or carboxyl) group suitably protected, under conditions that allow for the formation of an amide linkage. The protecting group is then removed from the newly added amino acid residue and the next amino acid (suitably protected) is then added, and so forth. After the desired amino acids have been linked in the proper sequence, any remaining protecting groups (and any solid support, if solid phase synthesis techniques are used) are removed sequentially or concurrently, to render the final polypeptide. By simple modification of this general procedure, it is possible to add more than one amino acid at a time to a growing chain, for example, by coupling (under conditions which do notracemize chiral centers) a protected tripeptide with a properly protected dipeptide to form, after deprotection, a pentapeptide. See, e.g., J. M. Stewart and J. D. Young, Solid Phase Peptide Synthesis (Pierce Chemical Co., Rockford, Ill. 1984) and G. Barany and R. B. Merrifield, The Peptides: Analysis, Synthesis, Biology, editors E. Gross and J. Meienhofer, Vol. 2, (Academic Press, New York, 1980), pp. 3-254, for solid phase peptide synthesis techniques; and M. Bodansky, Principles of Peptide Synthesis, (Springer-Verlag, Berlin 1984) and E. Gross and J. Meienhofer, Eds., The Peptides: Analysis. Synthesis. Biology, Vol. 1, for classical solution synthesis. These methods are suitable for synthesis of a peptide of the present disclosure.

A peptide as described herein can also be chemically prepared by other methods such as by the method of simultaneous multiple peptide synthesis. See, e.g., Houghten *Proc. Natl. Acad. Sci. USA* 82: 5131-5135, 1985 or U.S. Pat. No. 4,631,211.

Targeting Binding Proteins to the Cytoplasm

Various methods of targeting the binding proteins of the present disclosure to the cytoplasm of cells are available to those of skill in the art (e.g. as summarised in Marschall et al., mAbs, 3(1), 3-16, 2011).

For example, the binding protein of the present disclosure may have or be conjugated to a protein transduction domain (PTD). As used herein, a "protein transduction domain" or "PTD" is a sequence of amino acids that facilitates uptake of the binding protein into a cell.

For example, the amino acid sequence capable of enhancing, increasing or assisting uptake is the Drosophila penetratin targeting sequence. This peptide sequence at least comprises the amino acid sequence CysArgGlnIleLysIleTrpPheGlnAsnArgArg-MetLysTrpLysLys (SEQ ID NO: 17), further comprising (Xaa)n after the final Lys residue and followed by Cys wherein Xaa is any amino acid and n has a value greater than or equal to 1. In another example, a homologue, derivative or analogue of said sequence is used.

Alternative protein transduction domains are known in the art, and include, for example, a protein transduction domain from the HIV-I TAT protein, or a homolog, derivative or analog of the TAT4S-OO fragment.

Alternate protein transduction domains include non-inverted and retroinverted forms of a Kaposi fibroblast growth factor (FGF) hydrophobic peptide, optionally with a glycine spacer added; a non-inverted form of the signal sequence based peptide 1 and a retroinverted form thereof; a non-inverted form of the signal sequence based peptide 2 and a retroinverted form thereof, a non-inverted form of transportan protein transduction domain and a retroinverted form thereof; a non-inverted form of the an amphiphilic model peptide and a retroinverted form thereof, and a non-inverted form of a polyarginine peptide and a retroinverted form thereof.

In another example, the protein transduction domains includes amino acids 43-58 of Drosophila antennapedia, poly-arginine, PTD-5, Transportan and KALA (reviewed in Kabouridis, TRENDS in Biotechnology, 21: 498-503, 2003).

As explained herein, the protein transduction domain peptide may be produced with a glycine spacer residue that is endogenous to the peptide sequence and/or added to the C-terminus or N-terminus of the endogenous peptide sequence. In on example, if the peptide is not a retroinverted peptide, the spacer occurs in the native sequence or is added to the C-terminus of the peptide's native sequence during synthesis. In one example, if the peptide is a retroinverted peptide comprising D-amino acids other than glycine, the spacer is occurs at the C-terminus of the corresponding native sequence such that it is introduced at the N-terminus of the retroinverted sequence or is added to the N-terminus of the retroinverted peptide sequence during synthesis.

Attachment of the protein transduction domain can be effected using conventional techniques. For example, the binding protein can be produced recombinantly by expression of a nucleic acid encoding a fusion protein containing the binding protein fused to the transduction domain. In some examples, the transduction domain can be attached to the therapeutic antibody by chemical means using methods known in the art. Further, the protein transduction domain can be conjugated to the antibody either directly or indirectly via peptide or other chemical linkers.

Conjugates

In one example, a binding protein of the present disclosure is conjugated to an agent. For example, the agent is selected from the group consisting of a radioisotope, a detectable label, a therapeutic compound, a colloid, a toxin, a nucleic acid, a peptide, a protein, an agent that increases the half-life of the binding protein in a subject and mixtures thereof.

The binding protein can be directly or indirectly bound to the compound (e.g., can comprise a linker in the case of indirect binding). Examples of compounds include, a radioisotope (e.g., iodine-131, yttrium-90 or indium-111), a detectable label (e.g., a fluorophore or a fluorescent nanocrystal or quantum dot), a therapeutic compound (e.g., a chemotherapeutic or an anti-inflammatory), a colloid (e.g., gold), a toxin (e.g., ricin or tetanus toxoid), a nucleic acid, a peptide (e.g., a serum albumin binding peptide), a protein (e.g., a protein comprising an antigen binding domain of an antibody or serum albumin), an agent that increases the half-life of the compound in a subject (e.g., polyethylene glycol or other water soluble polymer having this activity) and mixtures thereof. Exemplary binding proteins that can be conjugated to a compound of the disclosure and methods for such conjugation are known in the art and described, for example, in WO2010/059821.

The binding protein may be conjugated to nanoparticles (for example as reviewed in Kogan et al., *Nanoinedicine (Lond)*. 2: 287-306, 2007). The nanoparticles may be metallic nanoparticles.

Some exemplary compounds that can be conjugated to a binding protein of the present disclosure are listed in Table 1.

TABLE 1

Compounds useful in conjugation.

| Group | Detail |
|---|---|
| Radioisotopes (either directly or indirectly) | $^{123}$I, $^{125}$I, $^{130}$I, $^{133}$I, $^{135}$I, $^{47}$Sc, $^{72}$As, $^{72}$Sc, $^{90}$Y, $^{88}$Y, $^{97}$Ru, $^{100}$Pd, $^{101m}$Rh, $^{101m}$Rh, $^{119}$Sb, $^{128}$Ba, $^{197}$Hg, $^{211}$At, $^{212}$Bi, $^{153}$Sm, $^{169}$Eu, $^{212}$Pb, $^{109}$Pd, $^{111}$In, $^{67}$Gu, $^{68}$Gu, $^{67}$Cu, $^{75}$Br, $^{76}$Br, $^{77}$Br, $^{99m}$Tc, $^{11}$C, $^{13}$N, $^{15}$O, $^{18}$I, $^{188}$Rc, $^{203}$Pb, $^{64}$Cu, $^{105}$Rh, $^{198}$Au, $^{199}$Ag or $^{177}$Lu |
| Half-life extenders | Polyethylene glycol<br>Glycerol<br>Glucose |
| Fluorescent probes | Phycoerythrin (PE)<br>Allophycocyanin (APC)<br>Alexa Fluor 488<br>Cy5.5 |
| Biologics | fluorescent proteins such as Renilla luciferase, GFP<br>immune modulators or proteins, such as cytokines, e.g.,<br>an interferon<br>toxins<br>an immunoglobulin or antibody or antibody variable region<br>half-life extenders such as albumin or antibody variable regions or peptides that bind to albumin |
| Chemotherapeutics | Taxol<br>5-FU<br>Doxorubicin<br>Idarubicin |

In one example, a binding protein of the disclosure is conjugated to a chemotherapy agent.

In one example, a binding protein of the disclosure is conjugated to a maytansinoid, e.g., DM1 or DM4.

In another example, a binding protein of the disclosure is conjugated to an auristatin, e.g., MMAE or MMAD.

In one example, a binding protein of the present disclosure is conjugated to an internalising moiety. An "internalising moiety" may direct the antibody inside a cell. In an example, an "internalising moiety" directs antibodies of the present disclosure into the cytoplasm or to an organelle (e.g. mitochondria) of a cell.

Alternatively, internalising moieties conjugated to antibodies of the present disclosure may assist or improve the penetration of an antibody into a cell, in particular into the cytoplasm or to an organelle of a cell.

For example, the binding protein of the present disclosure may be conjugated to a cell penetrating peptide or antibody such as a "transmab". In an example, the internalising moiety is antibody 3E10 (Weisbart et al. (2012) Mol Cancer Ther. 11(10), 2169-2173).

Assessing Therapeutic Efficacy

Various in vitro assays are available to assess the ability of a binding protein of the disclosure to treat a disease or condition described herein.

In one example, the efficacy of a binding protein to treat a disease or condition is assessed using an in vivo assay.

In one example, a xenotransplantation model of a cancer is used to assess therapeutic efficacy. For example, mice (e.g., NOD/SCID mice) are administered cancer cells and a binding protein of the disclosure is administered to the mice and the level of size of any tumor or the presence of any tumor or metastases thereof is assessed. A reduction in the size or number of tumors or metastases in the presence of the binding protein compared to in the absence of the binding protein indicates therapeutic efficacy.

Bak Binding Antibodies

An example of an antibody that can bind Bak and change the conformation of Bak from a non-activated to an activated conformation is 26/05-7D10-17-13. The 26/05-7D10-17-13 antibody is a rat IgG monoclonal antibody produced by the hybridoma SW1 (Accession #15041601). 26/05-7D10-17-13 specifically binds to the α1-α2 loop of Bak, triggering Bak activation, oligomerisation and cytochrome c release.

Predicted CDRs in the heavy chain variable region sequence set forth as SEQ ID NO:7 are denoted herein as CDR1 (SEQ ID NO:1), CDR2 (SEQ ID NO:2) and CDR3 (SEQ ID NO:3). Predicted CDRs in the light chain variable region sequence set forth as SEQ ID NO:8 are denoted herein as CDR1 (SEQ ID NO:4), CDR2 (SEQ ID NO:5) and CDR3 (SEQ ID NO:6). The location of additional regions, such as D- and J-regions are known to the skilled artisan.

The CDR sequences of 26/05-7D10-17-13 comprise or consist essentially of the following:

```
Heavy chain CDR1
                                          (SEQ ID NO: 1)
GFTFSNLAMA Heavy chain CDR2
                                          (SEQ ID NO: 2)
SISPAGITTYYRDSVKG;
and Heavy chain CDR3
                                          (SEQ ID NO: 3)
HTGKSSFFDY.

Light chain CDR1
                                          (SEQ ID NO: 4)
KATENINTYLA Light chain CDR2
                                          (SEQ ID NO: 5)
SGSTLQS;
and Light chain CDR3
                                          (SEQ ID NO: 6)
QQHNEYPLT
```

Other examples of Bak binding antibodies or binding fragments thereof encompassed by the present disclosure include antibodies or binding fragments thereof comprising a heavy chain variable region sequence, wherein the heavy chain variable region sequence is at least 70%, at least 80%, at least 85%, at least 90%, at least 95%, at least 99%, identical to the sequence shown in SEQ ID NO: 7 and a light chain variable region sequence, wherein the antibody or binding fragment thereof binds to SEQ ID NO: 9 and/or SEQ ID NO: 10.

In another example, the Bak binding antibody or binding fragment thereof comprises a heavy chain variable region sequence and a light chain variable region sequence, wherein the light chain variable region sequence is at least 70%, at least 80%, at least 85%, at least 90%, at least 95%, at least 99%, identical to the sequence shown in SEQ ID NO: 8, wherein the antibody or binding fragment thereof binds to SEQ ID NO: 9 and/or SEQ ID NO: 10.

In another example, the Bak binding antibody or binding fragment thereof comprises a heavy chain variable region sequence, wherein the heavy chain variable region sequence is at least 70%, at least 80%, at least 85%, at least 90%, at least 95%, at least 99%, identical to the sequence shown in SEQ ID NO: 7, and a light chain variable region sequence, wherein the light chain variable region sequence is at least 70%, at least 80%, at least 85%, at least 90%, at least 95%, at least 99%, identical to the sequence shown in SEQ ID NO: 8, wherein the antibody or binding fragment thereof binds to SEQ ID NO: 9 and/or SEQ ID NO: 10.

In another example, the Bak binding antibody or binding fragment thereof comprises a heavy chain variable region sequence, wherein the heavy chain variable region sequence is identical to the sequence shown in SEQ ID NO: 7, and a light chain variable region sequence, wherein the light chain variable region sequence is identical to the sequence shown in SEQ ID NO: 8, wherein the antibody or binding fragment thereof binds to SEQ ID NO: 9 and/or SEQ ID NO: 10.

In another example, the Bak binding antibody or binding fragment thereof comprises a heavy chain variable region sequence, wherein the heavy chain variable region sequence comprises an amino acid sequence as shown in SEQ ID NO: 7 with up to three amino acid substitutions and a light chain variable region sequence, wherein the antibody or binding fragment thereof binds to SEQ ID NO: 9 and/or SEQ ID NO: 10.

In another example, the Bak binding antibody or binding fragment thereof comprises a heavy chain variable region sequence and a light chain variable region sequence, wherein the light chain variable region sequence comprises an amino acid sequence as shown in SEQ ID NO: 8 with up to three amino acid substitutions, wherein the antibody or binding fragment thereof binds to SEQ ID NO: 9 and/or SEQ ID NO: 10.

In another example, the Bak binding antibody or binding fragment thereof comprises a heavy chain variable region sequence, wherein the heavy chain variable region sequence comprises an amino acid sequence as shown in SEQ ID NO: 7 with up to three amino acid substitutions, and a light chain variable region sequence, wherein the light chain variable region sequence comprises an amino acid sequence as shown in SEQ ID NO: 8 with up to three amino acid substitutions, wherein the antibody or binding fragment thereof binds to SEQ ID NO: 9 and/or SEQ ID NO: 10.

In another example, the Bak binding antibody or binding fragment thereof comprises a heavy chain variable region sequence, wherein the heavy chain variable region sequence comprises an amino acid sequence as shown in SEQ ID NO: 7 with up to two amino acid substitutions and a light chain variable region sequence, wherein the antibody or binding fragment thereof binds to SEQ ID NO: 9 and/or SEQ ID NO: 10.

In another example, the Bak binding antibody or binding fragment thereof comprises a heavy chain variable region sequence and a light chain variable region sequence, wherein the light chain variable region sequence comprises an amino acid sequence as shown in SEQ ID NO: 8 with up to two amino acid substitutions, wherein the antibody or binding fragment thereof binds to SEQ ID NO: 9 and/or SEQ ID NO: 10.

In another example, the Bak binding antibody or binding fragment thereof comprises a heavy chain variable region sequence, wherein the heavy chain variable region sequence comprises an amino acid sequence as shown in SEQ ID NO: 7 with up to two amino acid substitutions, and a light chain variable region sequence, wherein the light chain variable region sequence comprises an amino acid sequence as shown in SEQ ID NO: 8 with up to two amino acid substitutions, wherein the antibody or binding fragment thereof binds to SEQ ID NO: 9 and/or SEQ ID NO: 10.

In another example, the Bak binding antibody or binding fragment thereof comprises a heavy chain variable region sequence, wherein the heavy chain variable region sequence comprises an amino acid sequence as shown in SEQ ID NO: 7 with up to one amino acid substitution and a light chain variable region sequence, wherein the antibody or binding fragment thereof binds to SEQ ID NO: 9 and/or SEQ ID NO: 10.

In another example, the Bak binding antibody or binding fragment thereof comprises a heavy chain variable region sequence and a light chain variable region sequence, wherein the light chain variable region sequence comprises an amino acid sequence as shown in SEQ ID NO: 8 with up to one amino acid substitution, wherein the antibody or binding fragment thereof binds to SEQ ID NO: 9 and/or SEQ ID NO: 10.

In another example, the Bak binding antibody or binding fragment thereof comprises a heavy chain variable region sequence, wherein the heavy chain variable region sequence comprises an amino acid sequence as shown in SEQ ID NO: 7 with up to one amino acid substitution, and a light chain variable region sequence, wherein the light chain variable region sequence comprises an amino acid sequence as shown in SEQ ID NO: 8 with up to one amino acid substitution, wherein the antibody or binding fragment thereof binds to SEQ ID NO: 9 and/or SEQ ID NO: 10.

In another example, the Bak binding antibody or binding fragment thereof comprises a heavy chain variable region sequence, wherein the heavy chain variable region sequence comprises SEQ ID NO: 1, SEQ ID NO: 2 and SEQ ID NO: 3 and a light chain variable region sequence, wherein the antibody or binding fragment thereof binds to SEQ ID NO: 9 and/or SEQ ID NO: 10.

In another example, the Bak binding antibody or binding fragment thereof comprises a heavy chain variable region sequence, wherein the heavy chain variable region sequence comprises SEQ ID NO: 1, SEQ ID NO: 2 and SEQ ID NO: 3 and a light chain variable region sequence, wherein the light chain variable region sequence comprises an amino acid sequence as shown in SEQ ID NO: 8, wherein the antibody or binding fragment thereof binds to SEQ ID NO: 9 and/or SEQ ID NO: 10.

In another example, the Bak binding antibody or binding fragment thereof comprises a heavy chain variable region sequence and a light chain variable region sequence, wherein the light chain variable region sequence comprises SEQ ID NO: 4, SEQ ID NO: 5 and SEQ ID NO: 6, wherein the antibody or binding fragment thereof binds to SEQ ID NO: 9 and/or SEQ ID NO: 10.

In another example, the Bak binding antibody or binding fragment thereof comprises a heavy chain variable region sequence, wherein the heavy chain variable region sequence comprises an amino acid sequence as shown in SEQ ID NO: 7 and a light chain variable region sequence, wherein the light chain variable region sequence comprises, SEQ ID NO: 4, SEQ ID NO: 5 and SEQ ID NO: 6, wherein the antibody or binding fragment thereof binds to SEQ ID NO: 9 and/or SEQ ID NO: 10.

In another example, the Bak binding antibody or binding fragment thereof comprises a heavy chain variable region sequence, wherein the heavy chain variable region sequence comprises SEQ ID NO: 1, SEQ ID NO: 2 and SEQ ID NO: 3 and a light chain variable region sequence, wherein the light chain variable region sequence comprises, SEQ ID NO: 4, SEQ ID NO: 5 and SEQ ID NO: 6, wherein the antibody or binding fragment thereof binds to SEQ ID NO: 9 and/or SEQ ID NO: 10.

Selection of Binding Proteins that Specifically Bind to Bak

Suitable methods for selecting a binding protein (e.g., an antibody or antigen binding fragment thereof) that specifically binds to Bak, or an epitope thereof, and changes the conformation of Bak are available to those skilled in the art.

For example, a screen may be conducted to identify binding proteins capable of binding to Bak. Any binding protein that binds to Bak is then screened to identify those that do not substantially bind to a related protein, e.g., Bax.

For example, a phage display library displaying antibody fragments is screened with Bak or a soluble form thereof to identify proteins that bind thereto. One or more proteins related to Bak to which the antibody fragment is not to be able to detectably bind are then used to remove cross-reactive proteins. Identified binding proteins are then screened for activation of Bak.

The binding proteins of the present disclosure include those that compete for binding to an epitope of Bak with the antibody 26/05-7D10-17-13. The ability of a particular binding protein to recognize the same epitope as another antibody can be determined by the ability of one binding protein to competitively inhibit binding of the second antibody (e.g., competitively bind) to the antigen (e.g. as determined by competitive binding assays such as those disclosed in US patent publication No. 20090291085). Competitive inhibition of binding may also be referred to as cross-reactivity.

Any of a number of competitive binding assays can be used to measure competition between binding proteins and antibodies for the same antigen. For example, a sandwich ELISA assay can be used for this purpose. Means of assaying for cross-reactivity are well known to those of skill in the art (see, e.g., Dowbenko et al. (1988) J. Virol. 62: 4703-4711).

A binding protein is considered to competitively inhibit binding of a second antibody to an antigen if binding of the second antibody to the antigen is reduced by at least 30%, usually at least about 40%, 50%, 60% or 75%, and often by at least about 90%, in the presence of the first binding protein using any of the assays used to assess competitive binding.

Competitive binding can be ascertained by providing isolated Bak, for example, Bak attached to a solid support and assaying the ability of a binding protein to bind to Bak or to compete with an antibody described herein for binding to Bak (e.g. using surface plasmon resonance).

Determining Affinity

Optionally, the dissociation constant ($K_D$)) or association constant ($K_A$) or equilibrium constant ($K_D$)) of a binding protein for Bak or an epitope thereof is determined. These constants for a binding protein (e.g., an antibody or antigen binding fragment) are, in one example, measured by a radiolabeled or fluorescently-labeled Bak-binding assay. This assay equilibrates the binding protein with a minimal concentration of labeled Bak (or a soluble form thereof, e.g., comprising an extracellular region of Bak fused to an Fc region) in the presence of a titration series of unlabeled Bak. Following washing to remove unbound Bak, the amount of label is determined.

Affinity measurements can be determined by standard methodology for antibody reactions, for example, immunoassays, surface plasmon resonance (SPR) (Rich and Myszka *Curr. Opin. Biotechnol* 11:54, 2000; Englebienne *Analyst.* 123: 1599, 1998), isothermal titration calorimetry (ITC) or other kinetic interaction assays known in the art.

In one example, the constants are measured by using surface plasmon resonance assays, e.g., using BIAcore surface plasmon resonance (BIAcore, Inc., Piscataway, N.J.) with immobilized Bak or a region thereof. Exemplary SPR methods are described in U.S. Pat. No. 7,229,619.

Subject binding proteins can have a binding affinity for Bak comparable to about 5 nM or less, or about 4.9 nM, or about 4.8 nM, or about 4.7 nM, or about 4.6 nM, or about 4.7 nM, or about 4.6 nM, or about 4.5 nM, or about 4.4 nM, or about 4.3 nM, or about 4.2 nM, or about 4.1 nM, or about 4.0 nM, or about 3.9 nM, or about 3.8 nM, or about 3.7 nM, or about 3.6 nM, or about 3.5 nM, or about 3.4 nM, or about 3.3 nM, or about 3.2 nM, or about 3.1 nM, or about 3.0 nM.

In an example, subject binding proteins can have a binding affinity for full length human Bak (SwissProt Accession No. Q16611.1) comparable to about 100 pM, or about 150 pM, or about 200 pM, or about 250 pM, or about 300 pM, or about 350 pM, or about 400 pM, or about 450 pM, or about 466 pM as measured by surface plasmon resonance (e.g. using a BlAcore 3000 instrument).

In an example, subject binding proteins can have a binding affinity for human BakΔC25 (residues 1-186 of SwissProt Accession No. Q16611.1) comparable to about 100 pM, or about 150 pM, or about 200 pM, or about 250 pM, or about 300 pM, or about 350 pM, or about 400 pM, or about 450 pM, or about 466 pM as measured by surface plasmon resonance (e.g. using a BlAcore 3000 instrument).

In an example, subject binding proteins can have a binding affinity for residues E46 to S69 of human Bak comparable to about 1.5 nM, or about 2.0 nM, or about 2.5 nM, or about 2.7 nM or about 2.9 nM as measured by surface plasmon resonance (e.g. using a BIAcore 3000 instrument).

Moreover, the binding proteins of the present disclosure encompass those that bind to the same epitope on Bak as 26/05-7D10-17-13. Epitopes of antibodies can be ascertained by a number of standard techniques (see, e.g., Geysen et al (1987) J. Immunol. Meth 102:259-274). This technique involves the synthesis of large numbers of overlapping peptides of Bak. The synthesized peptides are then screened against 26/05-7D10-17-13 and the characteristic epitopes specifically bound by these antibodies can be identified by binding specificity and affinity. The epitopes thus identified can be conveniently used for the competitive assays described herein to identify cross-reacting binding proteins.

The peptides for epitope mapping can be conveniently prepared using "Multipin" peptide synthesis techniques (see, e.g., Geysen et al (1987) Science 235: 1184-1190). Using the known sequence of Bak, overlapping polypeptide sequences can be synthesized individually in a sequential manner on plastic pins in an array of one or more 96-well microtest plate(s).

Bak Binding Protein Activity

Bak binding proteins encompassed by the present disclosure can induce cytochrome release, promote or induce apoptosis and/or reduce or inhibit inactivation of Bak.

Induction of Cytochrome c Release

During apoptosis, cytochrome c is released from mitochondria to the cytosol to activate a caspase cascade, which commits the cell to the death process. Methods for determining increased cytochrome c release would be known to those of skill in the art and may embody an in vitro or in vivo assay. In one example, the level of cytochrome c released from a population or culture of cells is determined by Western blot using, for example, anti-cytochrome c (Clone 7H8.2C12, 1:1000, BD) and anti-βactin (Clone AC-15, 1:20,000, Sigma) primary antibodies and horseradish peroxidase (HRP)-conjugated sheep anti-mouse (NXA931, 1:2000, Amersham) goat anti-rabbit (4010-05, 1:5000, Southern Biotech), and goat anti-rat (3010-05, 1:5000 Southern Biotech) IgGs as secondary antibodies. In this example, antibody binding is visualised using a HRP substrate. Other methods of detecting cytochrome c release can include, ELISA and HPLC.

Promotion or Induction of Apoptosis

The binding proteins of the present disclosure may trigger cell death by a number of different mechanisms. In one example, the binding proteins are able to induce apoptosis in unwanted, proliferative cells.

The term "apoptosis" refers to the process of programmed cell death. In every person hundreds of thousands of old or damaged cells die each day by the process of apoptosis and are replaced in the ebb and flow of maintaining a constant number of living cells in the body. Old and damaged cells die in response to a signal triggered on the cell surface for the targeted cell to self-destruct. Apoptosis is distinguished from other mechanisms of cell death, such as necrosis, which results in inflammation including swelling, redness, pain and tenderness. Apoptosis does not stimulate such reactions. In apoptosis, the cells shrivel up, break into pieces and the contents are removed by methods that do not induce inflammation. For these reasons, it is highly desirable to induce apoptosis, rather than necrosis, in rapidly proliferating cells, such as cancer cells. However, mutations in some cancer cells confer resistance of these cells to apoptosis. In an example, the binding proteins of the present disclosure induce induce apoptosis in cancer cells which, because of mutations, are otherwise resistant to apoptosis.

The terms "proliferative cells," "proliferating cells," "rapidly proliferating cells," "undesirable proliferating cells," "undesirable rapidly proliferating cells," "unwanted rapidly proliferating cells," and the like, refer to cancer cells, precancer cells, and other abnormal, rapidly dividing cells in a subject.

Methods for detecting increased apoptosis would be known to those of skill in the art and may embody an in vitro or in vivo assay. Apoptosis can be measured in a variety of ways on the basis of colorimetric, luminescent, radiometric, or fluorometric assays known in the art. Apoptosis can be measured as a reduction in cell viability. Colorimetric techniques for determining cell viability include, for example, Trypan Blue exclusion (see, Examples 1 and 2). In brief, cells are stained with Trypan Blue and counted using a hemocytometer. Viable cells exclude the dye whereas dead and dying cells take up the blue dye and are easily distinguished under a light microscope. Neutral Red is adsorbed by viable cells and concentrates in cell lysosomes; viable cells can be determined with a light microscope by quantitating numbers of Neutral Red stained cells.

Fluorometric techniques for determining cell viability include, for example, propidium iodide, a fluorescent DNA intercalating agent. Propidium iodide is excluded from viable cells but stains the nucleus of dead cells due to cell membrane disruption. Flow cytometry of propidium iodide labeled cells can then be used to quantitate viable and dead cells. Release of lactate dehydrogenase (LDH) indicates structural damage and death of cells, and can be measured by a spectrophotometric enzyme assay.

Luminescent techniques for determining cell viability include, for example, the CellTiter-Glo luminescent cell viability assay (Promega Madison Wis.). This technique quantifies the amount of ATP present to determine the number of viable cells.

Methods of assessing Bak activation are exemplified below. Further, Bak activation increases cytochrome c release and induces apoptosis and therefore, a sustained increase in cytochrome c release and/or apoptosis suggests that a binding molecule is reducing or inhibiting inactivation of Bak. Accordingly, the cytochrome c and apoptosis assays known to one of skill in the art, exemplified below and discussed above will also be useful in determining whether a Bak binding protein reduces or inhibits Bak inactivation.

In-Vitro Assays

The skilled artisan will understand from the foregoing description that the present disclosure also provides an in vitro method of activating Bak in a cell. For example, a Bak binding protein of the present disclosure can be brought into contact with a cell or population of cells in culture. Activation of Bak can then be detected, for example, via immuno assay using antibodies that bind only activated and not non-activated Bak.

Similarly, the skilled artisan will understand from the foregoing description that the present disclosure also provides an in vitro method of inducing apoptosis in a cell. For example, a Bak binding protein of the present disclosure can be brought into contact with a cell or population of cells in culture. Induction of apoptosis can then be detected via the methods outlined in the present disclosure and/or those known by one of skill in the art.

For the avoidance of doubt, the term "induces apoptosis" relates to any increase in the number of cells which undergo apoptosis relative to an untreated control. In one example, the increase is at least 25%. In another example, the increase is at least 50%. In another example, the increase is at least one-fold.

It is also envisaged that the skilled artisan will understand from the foregoing description that the present disclosure also provides a method of identifying a molecule that changes the conformation of Bak.

Compositions

Suitably, in compositions or methods for administration of the binding protein of the disclosure to a mammal, the binding protein is combined with a pharmaceutically acceptable carrier as is understood in the art. Accordingly, one example of the present disclosure provides a composition (e.g., a pharmaceutical composition) comprising the binding protein of the disclosure combined with a pharmaceutically acceptable carrier. In another example, the disclosure provides a kit comprising a pharmaceutically acceptable carrier suitable for combining or mixing with the binding protein prior to administration to the mammal. In this example, the kit may further comprise instructions for use.

In general terms, by "carrier" is meant a solid or liquid filler, binder, diluent, encapsulating substance, emulsifier, wetting agent, solvent, suspending agent, coating or lubricant that may be safely administered to any mammal, e.g., a human. Depending upon the particular route of administration, a variety of acceptable carriers, known in the art may be used, as for example described in Remington's Pharmaceutical Sciences (Mack Publishing Co. N.J. USA, 1991).

By way of example only, the carriers may be selected from a group including sugars (e.g. sucrose, maltose, trehalose, glucose), starches, cellulose and its derivatives, malt, gelatine, talc, calcium sulfate, oils inclusive of vegetable oils, synthetic oils and synthetic mono- or di-glycerides, lower alcohols, polyols, alginic acid, phosphate buffered solutions, lubricants such as sodium or magnesium stearate, isotonic saline and pyrogen-free water.

For example, the carrier is compatible with, or suitable for, parenteral administration. Parenteral administration includes any route of administration that is not through the alimentary canal. Non-limiting examples of parenteral administration include injection, infusion and the like. By way of example, administration by injection includes intravenous, intra-arterial, intramuscular and subcutaneous injection. Also contemplated is delivery by a depot or slow-release formulation which may be delivered intradermally, intramuscularly and subcutaneously.

Conditions to be Treated

In some examples of the disclosure, a method described herein is for the treatment of a cancer. The term "cancer" refers to or describes the physiological condition in mammals that is typically characterized by unregulated cell growth. Examples of cancer include but are not limited to, carcinoma, lymphoma, blastoma, sarcoma, and leukemia or lymphoid malignancies. More particular examples of such cancers include, but are not limited to, squamous cell cancer (e.g., epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer and gastrointestinal stromal cancer, pancreatic cancer, glioblastoma, cervical cancer, ovarian cancer, liver cancer, bladder cancer, cancer of the urinary tract, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, melanoma, superficial spreading melanoma, lentigo maligna melanoma, acral lentiginous melanomas, nodular melanomas, multiple myeloma and B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); hairy cell leukemia; chronic myeloblastic leukemia; and post-transplant lymphoproliferative disorder (PTLD), as well as abnormal vascular proliferation associated with phakomatoses, edema (such as that associated with brain tumors), Meigs' syndrome, brain, as well as head and neck cancer, and associated metastases.

It will be appreciated by persons skilled in the art that numerous variations and/or modifications may be made to the disclosure as shown in the specific examples without departing from the spirit or scope of the disclosure as broadly described. The present examples are, therefore, to be considered in all respects as illustrative and not restrictive. The present application claims priority from U.S. 62/002,212 and AU 2014202830 filed 23 May 2014, the disclosures of which are incorporated herein by reference.

All publications discussed and/or referenced herein are incorporated herein in their entirety.

Any discussion of documents, acts, materials, devices, articles or the like which has been included in the present specification is solely for the purpose of providing a context for the present disclosure. It is not to be taken as an admission that any or all of these matters form part of the prior art base or were common general knowledge in the field relevant to the present disclosure as it existed before the priority date of each claim of this application.

The present disclosure includes the following non-limiting Examples.

Figure 1:
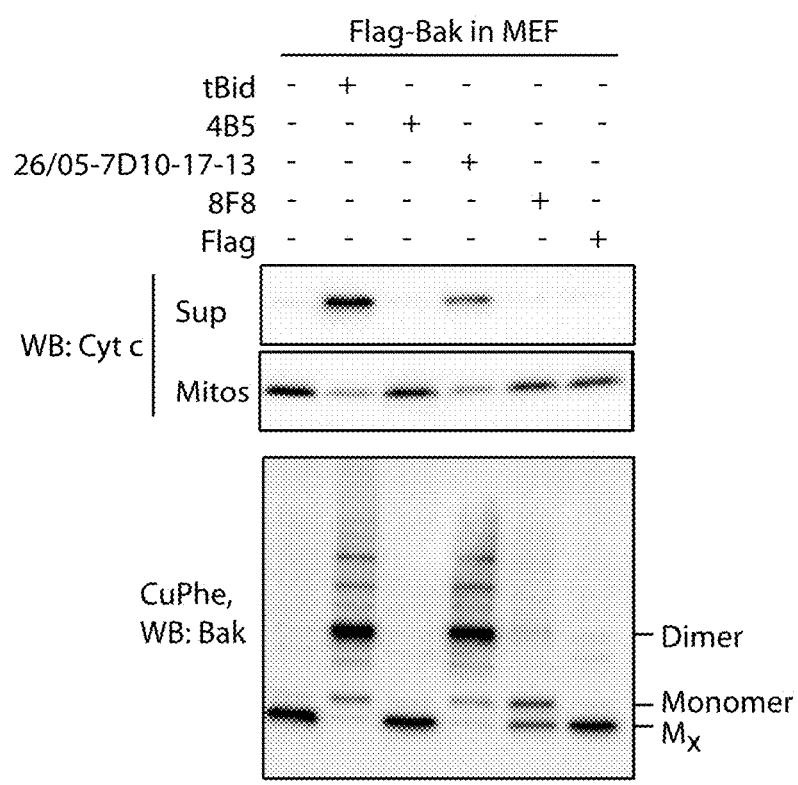
FIG. 1: The 26/05-7D10-17-13 antibody, but not other tested antibodies, can trigger Bak activation, oligomerisation and cytochrome c release. Mouse embryonic fibroblasts (MEFs) from Bak-/-Bax-/- mice that expressed FLAG-tagged human Bak were permeabilized with digitonin. Mitochondrial fractions were then incubated with tBid or one of the four indicated MAbs for 30 min at 30° C. Aliquots were then assessed for cytochrome c release (upper panels), or exposed to the oxidant copper phenanthroline (CuPhe) and run on non-reducing SDS-PAGE (lower panel). Mx marks inactive Bak monomers, which form an intra-molecular disulphide link.

Example 1: Bak can be Activated by an Antibody to Oligomerise and Form the Apoptotic Pore Incubating the 26/05-7D10-17-13 anti-Bak antibody with mitochondria (which contain Bak) promoted full activation of Bak and resulted in cytochrome c release (FIG. 1, lane 4). 26/05-7D10-17-13 was as effective as the potent natural activator tBid in eliciting Bak conformation change and oligomerisation (as indicated by cysteine linkage). In contrast, two rat monoclonal antibodies (4B5, 8F8) that recognise Bak only after it has been activated (Dewson et al., Mol Cell, 36, 696-703, 2009, Dewson et al., Mol Cell, 30, 369-703, 2008), failed to activate Bak (FIG. 1, lanes 3 and 5).

Example 2: Most Bak Antibodies Bind to Linear Epitopes

To facilitate a detailed investigation of Bak N-terminal conformation change the properties of eleven anti-Bak antibodies were compared.

Antibodies were first tested by SDS-PAGE and Western blotting to determine if their epitope was "linear" or "assembled". Assembled epitopes (also called discontinuous or 'conformational' epitopes) are disrupted during sample preparation for SDS-PAGE as they comprise residues brought together by protein folding. In contrast, linear epitopes (also called continuous or sequential epitopes) consist of residues close together in the primary sequence (Geysen et al., Journal of immunological methods 102, 259-274, 1987). All antibodies recognized human Bak on western blots (FIG. 2A), signifying linear epitopes.

Each antibody was also tested for its ability to bind mouse Bak, since the mouse Bak protein sequence is 77% similar to human Bak. Six antibodies—14-36, NT, a23-38, G317-2, 4B5 and G23—recognized mouse Bak (FIG. 2A). The epitopes of 4B5 and G23 were previously mapped to a region of 100% identity between mouse and human Bak (Dewson et al., Mol Cell, 30, 369-380, 2008). The immunogens of another three of these antibodies (14-36, NT and a23-38) contain the same stretch of conserved residues (23-36), thus explaining why those antibodies recognized both proteins. It was therefore hypothesized that the G317-2 epitope also lies in a region of sequence homology. Failure of the remaining five antibodies to recognize mouse Bak is likely due to sequence divergence in those epitopes.

Example 3: Epitopes Map to Various Sites in the Bak N-Terminus

Since most epitopes were linear, further mapping was performed using peptide arrays. Two arrays of overlapping 15-mer peptides (each offset by 10 residues) that collectively spanned the entire sequences of human and mouse Bak were designed. Biotinylated peptides were immobilized on streptavidin-coated plates and each antibody tested by ELISA.

All antibodies bound to at least one human Bak peptide (FIG. 2B), while those that showed limited recognition of mouse Bak by western blotting also failed to bind any mouse Bak peptides (FIG. 9). The one exception was 26/05-7D10-17-13 which bound peptides from both the human and mouse Bak arrays, despite only binding to human Bak during western blotting (FIG. 2A). With regard to structural domains of Bak, two antibodies (2-14 (Lifespan Bio), 8F8 (WEHI monoclonal antibody facility) bound peptides from the N-segment, six antibodies (14-36 (BD), NT (Upstate/Millipore), a23-38 (Sigma), G317-2 (BD), Ab-1 (Calbiochem), and Ab-2 (Calbiochem)) bound peptides encompassing the α1 helix, one antibody (26/05-7D10-17-13 (WEHI monoclonal antibody facility) bound peptides in the α1-2 loop, and two antibodies (4B5 (WEHI monoclonal antibody facility), G23 (Santa Cruz)) bound peptides spanning the BH3 domain.

The fragments of Bak bound by peptide-derived antibodies (2-14, 14-36, NT, aa23-38) corresponded to their immunogens (compare FIG. 2B). Binding of 8F8 to the peptide for residues 11-25 (FIG. 2B), was consistent with previous mapping of its epitope to residues 8-17 (Dewson et al, Mol Cell, 36, 696-703, 2009), but indicated the epitope comprises only residues 11-17. In contrast, the epitope of the other N-segment antibody, 2-14, includes more N-terminal residues, since it was unable to bind Bak lacking only the first 7 residues (FIG. 2C). The two antibodies to the BH3 domain (4B5, G23) bound peptides spanning that domain. The distinction between these epitopes suggested by the binding of different mouse Bak peptides by the two antibodies (FIG. 9) is also consistent with previous mapping data (Dewson et al, Mol Cell, 30, 369-380, 2008).

To better resolve the α1 epitopes, another ELISA using an array of 39 overlapping 8-mer peptides that collectively spanned residues 20-65 of human Bak was performed. With these peptides, which were offset by only 1 residue each, the minimal set of residues required for antibody binding from the residues common to all peptides bound by any particular antibody were defined. Due to being polyclonal, the 14-36, NT and α23-38 antibodies produced complex binding patterns, though each antibody bound a unique pattern of peptides (FIG. 10). In contrast, the monoclonal antibodies (G317-2, Ab-1, Ab-2 and 26/05-7D10-17-13) produced simple binding patterns. G317-2 bound four peptides in this array (FIG. 3A), confirming evidence from the 15-mer arrays (FIG. 2A and FIG. 9) that its epitope may be within TEEVFRS (SEQ ID NO: 18) of Bak but refining it further to EEVFR (SEQ ID NO: 19), and suggesting E32 and R36 are particularly important for binding since the absence of either in overlapping peptides precluded binding. Ab-1 and Ab-2 both bound predominantly to the same peptide YVFYRHQQ (residues 38-45; SEQ ID NO: 20), suggesting their epitopes are very similar, if not identical. The 26/05-7D10-17-13 epitope is also distinct, with GVAAP (SEQ ID NO: 10) the minimal set of residues required for binding. The identified binding site of 26/05-7D10-17-13 is remote from the hydrophobic groove that is the major binding site of Bid and Bim.

Example 4: Mutagenesis of α1 Identifies Residues Critical for Bak Stability, or for Antibody Recognition To gain insight into α1 function 10 mutants of Bak were generated by replacing individual residues throughout the helix (E25, A28, V34, F35, R36, S37, Y38, Y41, R42, Q44) with cysteine (FIG. 3B, C). Several mutants were present at only low levels after stable expression in Bak−/−Bax−/− MEFs, indicating those mutations destabilize (but do not activate) the protein. In particular, substitution of each of the hydrophobic residues V34, F35 and Y38 resulted in poor expression (FIG. 3C). Each of these three residues lie in the BH4 domain of Bak (FIG. 3B), i.e. the sequence motif φ1φ2XXφ3φ4, where X is any amino acid, φ is a hydrophobic residue and φ3 is an aromatic residue (Kvansakul et al., Cell Death Differ, 15, 1564-1571, 2008).

The cysteine-substituted Bak variants were also used to test whether the residues within α1 epitopes were required for antibody binding (FIG. 3D). For example, G317-2 failed to bind V34C, F35C and R36C, consistent with its epitope being at EEVFR (SEQ ID NO: 19. Ab-1 and Ab-2 failed to bind Y38C, Y41C and R42C, and only weakly bound S37C and Q44C, consistent with their epitope being within YVFYRHQQ (SEQ ID NO: 20). Among the polyclonal antibodies, both a23-38 and NT bound weakly to A28 (FIG. 3D), indicating that dominant epitopes among their collections of immunoglobulins overlap, and most immunoglobulins depend on A28 for binding. The epitopes of 14-36 seem also to be sensitive to mutation of A28 and V34 (FIG. 3D). Thus, anti-Bak antibodies bind to three distinct sites (residues 28, 34-36 and 37-44) along α1.

Example 5: The Bak N-Terminus Dissociates from Both the Core and Latch Domains During Activation In non-activated (human) Bak found in healthy cells, the α1-α2 loop of Bak is exposed at the surface of Bak (FIG. 11A) and accordingly is recognized by the 26/05-7D10-17-13 antibody (FIG. 4B). A large portion of the α1 helix is also exposed at the surface of Bak and theoretically accessible to antibodies (FIG. 11A). However, when Bak α1 epitopes are visualized in the X-ray structure of non-activated Bak (FIG. 11B) two residues (Y38 and R42) are important for binding by the Ab-1 antibody that is widely used to monitor Bak 'activation' (Griffiths et al., Journal of Cell Biology, 144, 903-914, 1999), are clearly located on the buried hydrophobic surface of α1, facing towards α3 and α5 in the core of Bak. Thus, as Ab-1 only binds activated Bak, this central region of α1 must become exposed during apoptosis by dissociating from the α2-5 core of Bak. Similarly, the N-terminal region of α1 likely becomes exposed during apoptosis by dissociating from the α6-8 latch of Bak since A28, the key residue in the epitopes of the polyclonal NT antibody that also recognizes only activated human Bak (Cuconati et al., Genes & development, 17, 2922-2932, 2002), lies on the buried hydrophobic surface of α1, facing toward α6 (FIG. 11B). As the 8F8 antibody also binds preferentially to activated Bak, indicating that the N-segment is at least partially structured (Dewson et al., Mol Cell, 36, 696-703, 2009), residues in at least 3 distinct sites within the Bak N-terminus (11-17, 28, and 38-44) become exposed during activation.

To confirm the extent of the region dissociating from the Bak α2-5 core and α6-8 latch during activation, other antibodies mapping to the N-segment and α1-helix (2-14, 14-36, a23-38 and G317-2) were tested to assess whether they were specific for activated human Bak, and whether they, and NT, were similarly specific for activated mouse Bak. Each antibody was used to immunoprecipitate Bak incubated with or without Bid (FIG. 4). Four of the five antibodies clearly bound more efficiently to both activated human and mouse Bak, though the 14-36 and G317-2 antibodies were superior to NT and a23-38 in their binding (FIG. 4, compare bound and unbound fractions). The human Bak-specific 2-14 antibody gave variable results but still suggests any weak interactions between the N-terminus and either the core or latch domains are decreased by activation. Thus, effectively the entire N-terminus (ie N-segment+α1) dissociates from the remainder of Bak during activation and, from a functional point of view, Bak N-terminal conformation change may be considered synonymous with "BH4 exposure", much as α2 conformation changes (detected by the 4B5 and G23 antibodies) represent "BH3 exposure".

Example 6: BH4 Exposure is Initiated by Movement of the α2 Helix

Having determined that the central region of α1 dissociates from the α2-5 core of Bak during apoptosis, BH4 exposure was assessed to determine whether BH4 exposure occurs before or after apoptosis induction by different stimuli. This was done by placing disulfide tethers at three positions within the N-terminus (FIG. 5A) and measuring the degree of exposure of α1 and α2 epitopes after an apoptotic stimulus.

Figure 5:
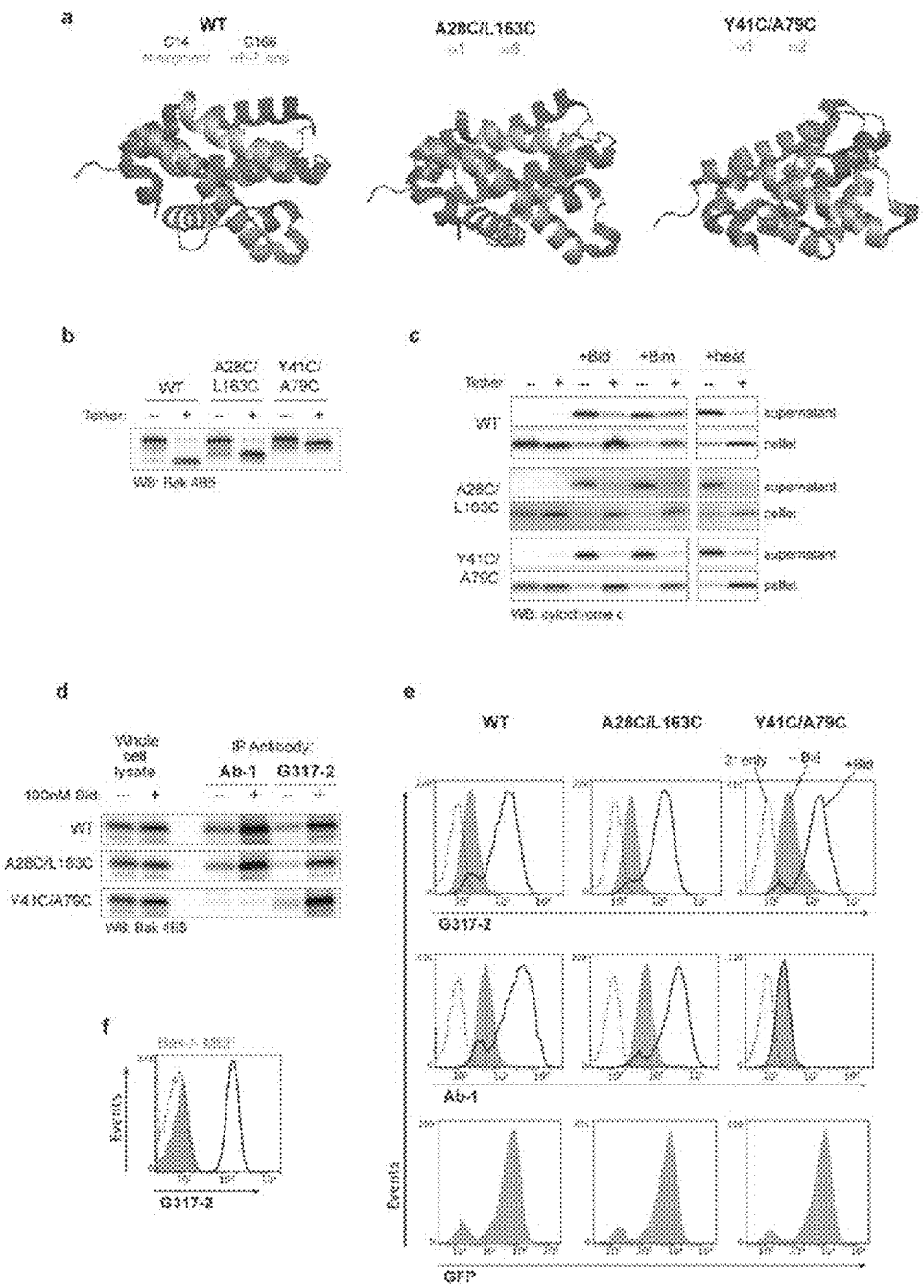
FIG. 5A-5F: N-terminal tethers. (A) Position of residues (red) in the inactive Bak structure (2IMS) that can be cross linked with the oxidant CuPhe to generate tethers; α1 is shown in yellow, α6 in cyan and a2 in lilac. Note, as the inactive structure was derived using calpain truncated Bak (Moldoveanu et al., Molecular Cell, 24, 677-688, 2006), in the case of WT Bak the most N-terminal residue present (S21) is marked red as a surrogate for C14 (whose exact position is not known). (B) Tethers were efficiently induced by CuPhe cross-linking of cysteines in non-activated Bak. DKO MEFs expressing WT human Bak or the A28C/L163C and Y41C/A79C double mutants were incubated with (+) or without (−) 200 uM CuPhe (at least 5 min, on ice) and Bak tethering was assayed by western blot (after non-reducing SDS-PAGE) using the 4B5 antibody (n>3). Cross-linked Bak appears as a faster migrating fragment, with differences in migration between cells reflecting the differing positions of the tethers (C) All tethers block cytochrome c release in response to apoptotic stimuli. After treating (or not) with CuPhe to induce tethers (as in B), membrane fractions were incubated (30 min) with or without either 100 nM Bid (30°
Figure 6:
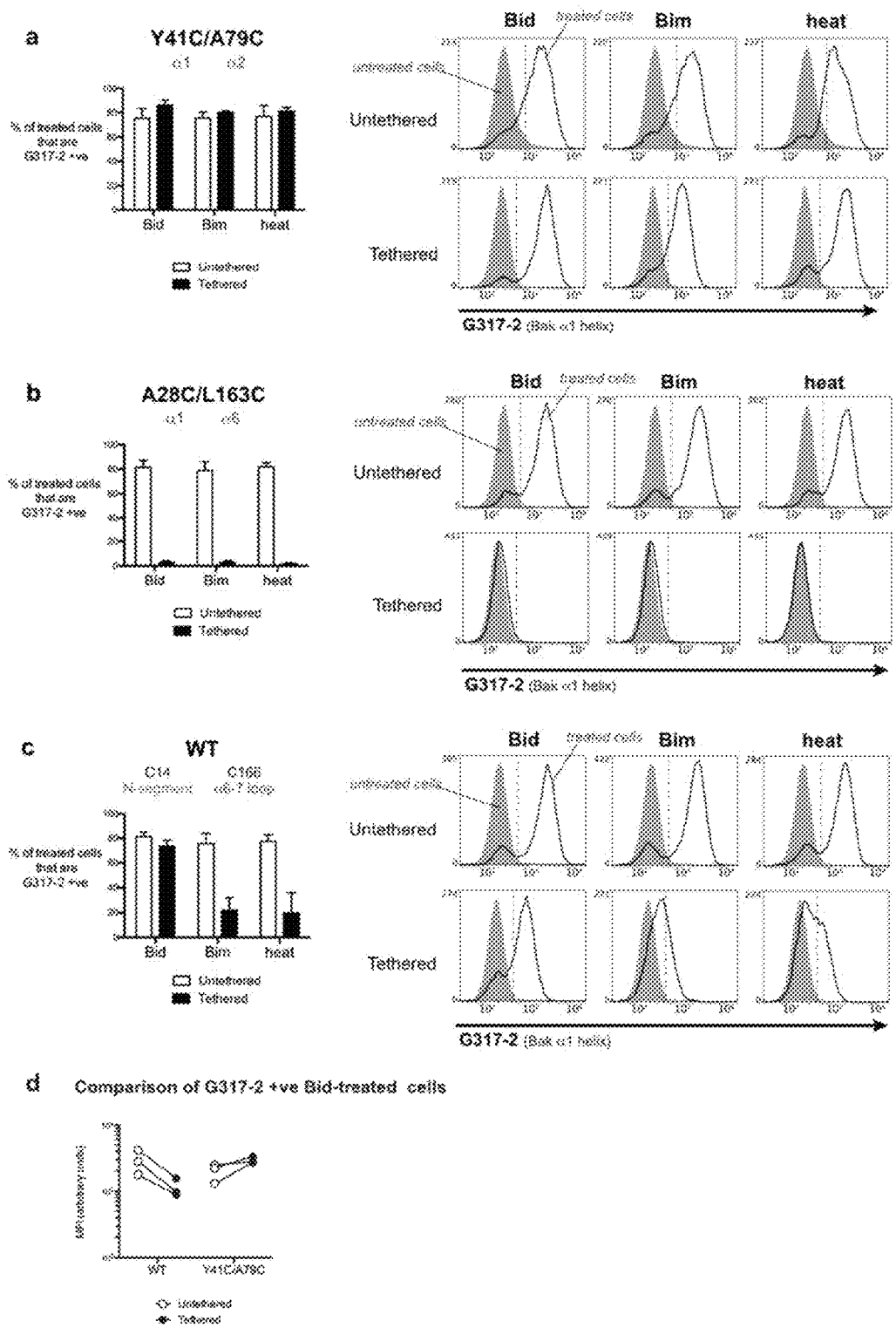

One tether utilized the native cysteines in human Bak, C14 in the N-segment and C166 in the α6-7 loop. The two other tethers involved cysteine substitutions at Y41 and A79 (α1-α2 tether) or A28 and L163 (α1-α6 tether), generated in cysteine-less human Bak (C14S/C166S). Each tether was induced with high efficiency by addition of the oxidizing agent CuPhe, and results in faster migration of monomeric Bak during SDS PAGE (FIG. 5B). In the absence of CuPhe, A28C/L163C and Y41C/A79C Bak were as efficient as WT Bak in releasing cytochrome c in response to Bak activators, indicating both mutants are functional. Upon induction with CuPhe each tether blocked cytochrome c release in response to the direct activator Bid, indicating that N terminal conformation change is required for Bak pore formation. Each tether also prevented cytochrome c release in response to other Bak activators, i.e. Bim BH3 peptide and heat (44° C.)(FIG. 5C).

To assess which Bak conformation changes are hindered by these tethers epitope exposure was assessed by flow cytometry. As the Y41C substitution lies within the Ab 1 epitope (FIG. 3D, FIG. 12) and prevents Ab-1 from binding to Bid-activated Y41C/A79C Bak (FIG. 5D-E) the G317-2 antibody, whose epitope in α1 is immediately N-terminal to that of Ab-1 (FIG. 3D, FIG. 12), was tested to determine whether it could substitute for Ab-1. Only G317-2 bound to Bid-treated Y41C/A79C Bak, though Ab-1 and G317-2 bound equally to Bid-treated WT and A28/L163C Bak (FIG. 5D-E). G317-2 binding of activated mouse Bak could also be detected by FACS (FIG. 5F) and thus G317-2 represents a novel means to assess BH4 exposure of human and mouse Bak by FACS and was used in experiments to determine whether tethering at the N-terminus blocks BH4 exposure.

Further tethering the α1 and α2 helices (Y41C/A79C) immediately prior to apoptotic stimulation (Bid, Bim BH3 peptide, or heat), G317-2 bound equally well to tethered and non-tethered Bak (FIG. 6A). This suggested the α1-α2 tether did not affect Bak's ability to undergo N-terminal conformation change. In other words, though tied together, α1 and α2 were both able to dissociate from α5 in the core and α6-8 of the latch domain to expose the hydrophobic BH4 domain in α1.

In contrast, the α1-α6 tether of A28C/L163C Bak completely blocked G317-2 epitope exposure in response to Bid, Bim BH3 peptide or heat (FIG. 6B). However the N segment—α6-7 loop tether of WT Bak did not similarly block G317-2 epitope exposure in response to Bid (FIG. 6C). Instead, equal proportions of cells with tethered or untethered WT Bak responded to Bid, though the mean fluorescence intensity for G317-2 was consistently lower in cells with tethered versus untethered WT Bak (FIG. 6D) suggesting access to the G317-2 epitope was restricted by this tether. It is unclear why Bim peptide or heat were less efficient than Bid in exposing the BH4 domain in cells with tethered WT Bak, but it may be that the small size of the Bim peptide or its failure to anchor to the membrane limits its ability to distort the hydrophobic groove when the N-segment is constrained. Nevertheless, since the tether in WT Bak specifically limits movement of the N segment rather than α1, it presumably allows α1 greater freedom to move or rotate than when tethered to α6 in A28C/L163C Bak. Thus, tethering of α1 to α2, α1 to α6 and the N-segment to the α6-7 loop collectively suggest the dissociation of the Bak N-terminus from the hydrophobic core might be occurring in the sequence: (1) α2 (BH3 domain), (2) α1 (BH4 domain), (3) Nsegment.

To verify whether α2 movement might precede α1 movement in response to apoptotic stimuli, exposure of the 4B5 epitope in the Bak BH3 domain at the C-terminus of α2 was examined to determine whether exposure could occur without dissociation of the BH4 domain from the Bak hydrophobic core, a scenario made plausible by the length of the loop linking α1 to α2. To do this the intracellular FACS assay was modified by adding the 4B5 antibody to permeabilized cells immediately after CuPhe addition but before Bid addition. This enabled 4B5 to capture BH3 domains exposed in response to Bid, before they became buried in the BH3:groove dimer interface, as observed in each Bak variant when untethered (FIG. 6A, upper panels).

In contrast to the results for the BH4 domain (FIG. 6), the 4B5 antibody bound to all three Bak variants when tethered (FIG. 7A), suggesting that BH3 exposure is a very early step in activation-associated Bak conformation changes. Of particular note, the α1-α6 tether of A28C/L163C Bak allowed BH3 exposure in most cells, despite its complete restriction of BH4 exposure (FIG. 6B), thereby supporting the hypothesis that α2 movement precedes α1 dissociation from the hydrophobic core of Bak.

However, when evaluating BH3 domain exposure by A28C/L163C and WT Bak in response to BID, in both cases (although equal proportions of tethered and untethered cells responded to Bid), the mean fluorescence intensity of 4B5 binding was consistently lower in cells with tethered Bak (FIG. 7B). This suggests that flexion of the α1-2 loop alone is insufficient for complete BH3 exposure. Since complete BH3 exposure did, however, occur in the α1-α2 tether (Y41C/A79C) it appears that full BH3 exposure requires movement of the N-segment and α1 away from α6.

In summary, these findings indicate that BH3 exposure precedes BH4 exposure (ie N terminal conformation change), but that α1 dissociation from the α6-8 latch of Bak is needed for complete BH3 exposure. It is proposed that Bak conformation change in response to apoptotic stimuli is initiated by movement of the C-terminus of the α2 (caused by a BH3-only protein interacting with the groove), which consequently drags the α1 helix and N-segment away from the the α6-8 latch of Bak (and α5 in the core) and also drives the eversion of the BH3 domain from the α2-5 core of Bak.

Example 7: BH3:Groove Dimer Formation Requires Dissociation of α1 from α2

Previously we've shown that after 30 min incubation with Bid, the BH3 domain of most Bak molecules is not available for binding by 4B5 due to its insertion into the hydrophobic groove of another activated Bak molecule (Dewson et al, Mol Cell, 30, 369-380, 2008). Therefore it was hypothesised that if tethered Y41C/A79C Bak had everted its BH3 domain but could no longer dimerize, it would still be able to bind 4B5 added after 30 minutes treatment with BID. When tested by intracellular FACS (FIG. 7C) at least double the number of cells with tethered Y41C/A79C Bak bound 4B5, compared to cells with non-tethered Y41C/A79C Bak. This suggests the α1-α2 tether prevents Y41C/A79C Bak from completing the conformation change required for dimerization and infers that, in addition to BH3 domain exposure, the Bak α1 and α2 helices must also dissociate for dimerization to occur.

Altogether, these results suggest that activation-associated Bak conformation change is driven by movement of α2, and that dissociation of α1 from α2 and α5 in the core domain, and α6 in the latch domain is required for dimerization to occur.

Example 8: Model of Bak Conformation Change Initiated at Two Distinct Sites—Groove or Loop While tBid and certain other BH3-only proteins trigger Bak activation by binding to the hydrophobic groove, the 26/05-7D10-17-13 MAb binds instead to the α1-α2 loop (FIG. 12). Both events trigger major conformation changes, including exposure of α1 and BH3 domains, and Core/Latch separation. Two Bak molecules with an exposed BH3 domain can then form a symmetric BH3-to-groove dimer. Multimers of these dimers then porate the mitochondrial outer membrane to kill the cell.

Example 9: Activation of Bak by 26/05-7D10-17-13 Requires the Stretch of Residues Shown in SEQ ID NO: 9

Variations of the $^{51}$GVAAPAD$^{57}$ (SEQ ID NO: 9) stretch of hBak residues were placed in the loop of mouse Bak and the proteins stably expressed in Bak−/−Bax−/−MEFs. Mitochondrial membrane fractions were then incubated with either tBid or 26/05-7D10-17-13 and tested for cytochrome c release. Generating GV/AAAPAD in mouse Bak allowed their activation by 26/05-7D10-17-13 (FIG. 13).

The α1-α2 loop, and the 26/05-7D10-17-13 epitope in particular, is thus a unique tool for exploring Bak activation. The crystal structures of Bak (2IMT, 2YVT, 2JCN) indicate that the loop is unstructured except for the α1' helix 58PEMVT62 which positions above a pocket lined by α1 and α6. As side chains project into this pocket in Bak, it is possible that targeting this pocket might dislodge the loop sufficiently to activate Bak.

Example 10: Bak Activation within and Adjacent the α1-α2 Loop

Certain cysteine substitutions prevented 26/05-7D10-17-13-activation of Bak: neither Bak G51C nor P55C were immunoprecipitated or activated by 26/05-7D10-17-13 (FIG. 14). Bak G51C also did not precipitate with 26/05-7D10-17-13 even if it had been oligomerised by tBid, supporting other evidence that G51C is a critical residue in the 26/05-7D10-17-13 epitope. In contrast, Bak P55C did bind to 26/05-7D10-17-13 after tBid treatment, indicating that P55 is not critical for 26/05-7D10-17-13 binding, but may be important for positioning the epitope for recognition in non-activated Bak. D57 also appears important for positioning the epitope, as N55D in mouse Bak allowed 26/05-7D10-17-13 activation but N55 was sufficient for binding of 26/05-7D10-17-13 after Bak activation (FIG. 14). The trend for greater 26/05-7D10-17-13 binding after Bak activation suggests that the 26/05-7D10-17-13 epitope is only partially exposed in non-activated Bak. Notably, insertion of the FLAG epitope just before or just after the 26/05-7D10-17-13 epitope conferred activation by anti-FLAG antibodies (not shown), indicating that several regions in the loop might be targeted to activate Bak.

Example 11: Determining the Structure of Bound to the Epitope

The hBakΔC:Fab complex has been generated and purified and is ready for crystal trays (FIG. 15). In parallel, complexes of the 26/05-7D10-17-13 Fab bound to a large peptide fragment spanning the epitope will provide a second opportunity to obtain crystals. NMR of the peptide in combination with either Fab or the smaller scFv should also be feasible. The structures should define the epitope and its structure once bound, and may also identify possible clashes of the antibody with the rest of the Bak structure that might initiate Bak unfolding.

Example 12: Auto-Activation, i.e. Whether Active Bak can Activate Other Bak Molecules It is proposed that Bak can auto-activate (Gavathiotis et al., Molecular Cell, 40, 481-92, 2010, Kim et al., Mol Cell, 36, 487-99, 2009, Tan et al., Chemistry, 281, 14764-75, 2006). That is, once their BH3 domain is exposed during activation, Bak can act like a BH3-only protein to trigger activation of further Bak molecules. Such a positive feedback loop would in theory ensure cells undergo rapid and complete mitochondrial permeabilisation.

FIG. 16 shows preliminary data that auto-activation can occur from human Bak to mouse Bak.

Example 13: A Fragment of 26/05-7D10-17-13, the Fab, Also Activates Bak

Figure 17:
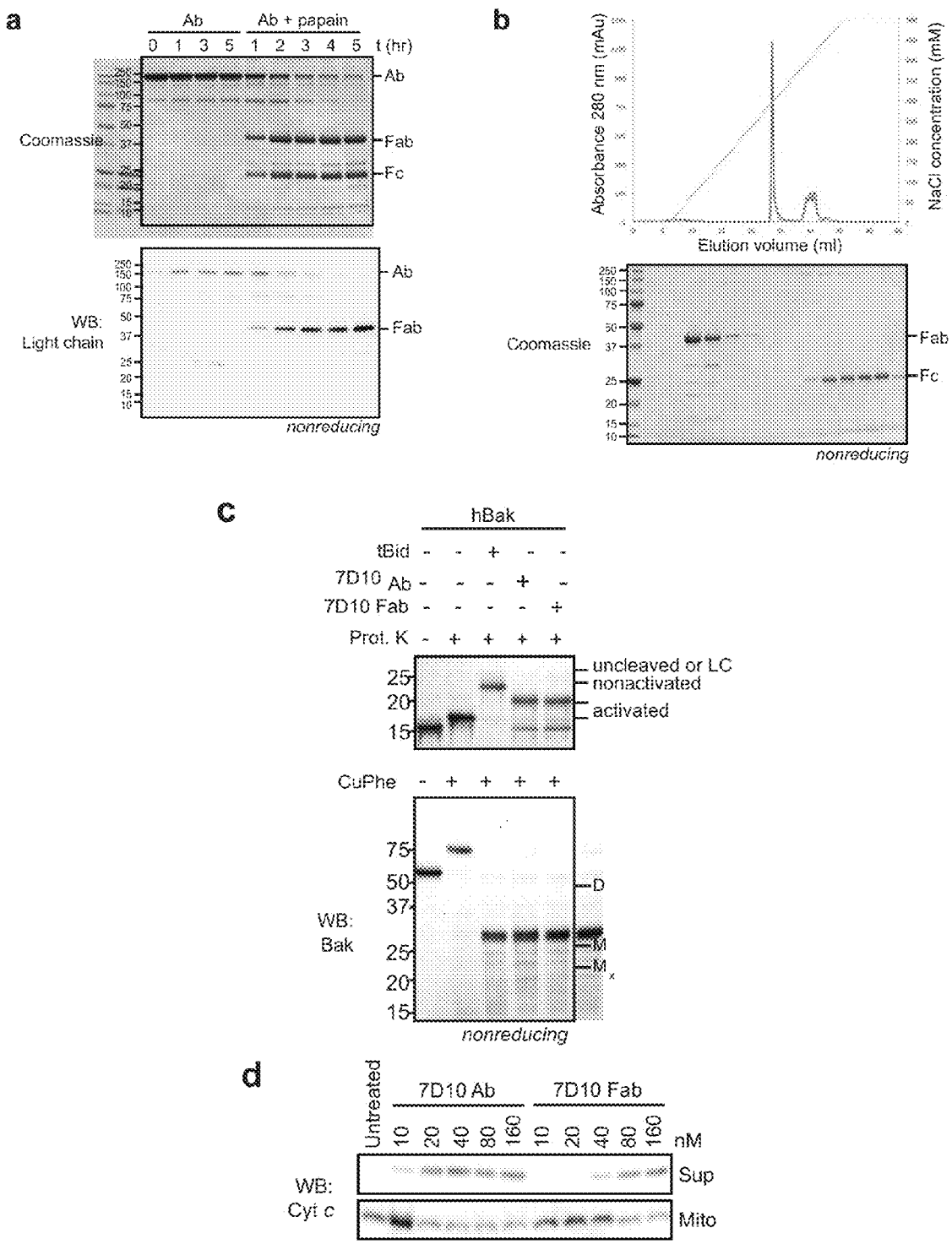

26/05-7D10-17-13 Fab (~50 kDa) was purified (FIG. 17A, 17B) and incubated with mitochondria. Bak underwent activation and oligomerization, and released cytochrome c with only slightly less molar efficiency than the 26/05-7D10-17-13 antibody (FIG. 17C, 17D). Thus, the bivalency or bulk (~150 kDa) of 26/05-7D10-17-13 does not appear to be important for Bak activation.

Notably, when microinjected into oocytes, the 26/05-7D10-17-13 Fab induced major changes in mitochondrial morphology (FIG. 18), suggesting that targeting the loop may have physiological and even clinical relevance.

Example 14: Isothermal Titration Microcalorimetry (ITC) and Surface Plasmon Resonance Binding Profile of 26/05-7D10-17-13

Two ITC experiments are shown in FIG. 19 for 26/05-7D10-17-13 antibody binding to loop peptide ($^{46}$EQEAE GVAAPADPEMVTLPLQPSS$^{69}$; SEQ ID NO: 21) at 25° C. As expected, the number of binding sites was approximately 2 (1.72 and 1.67), and affinity was stronger than 4 nM.

A BIAcore 3000 instrument was also used to examine the binding profile of 26/05-7D10-17-13. Antibody affinity for humanΔC25 Bak protein (residues 1-186 of SwissProt Accession No. Q16611.1) was: KD=466 pM. Antibody affinity for Bak peptide (residues E46 to S69 of human Bak was: KD=2.9 nM.

Example 15: Methods and Materials

Antibodies and Other Materials

Anti-Bak antibodies included 2-14 (Lifespan Bio), 8F8 (WEHI monoclonal antibody facility), 14-36 (BD), NT (Upstate/Millipore), a23-38 (Sigma), G317-2 (BD), Ab-1 (Calbiochem), and Ab-2 (Calbiochem), 26/05-7D10-17-13 (WEHI monoclonal antibody facility), 4B5 (WEHI monoclonal antibody facility), G23 (Santa Cruz). Other primary antibodies used were anti-cytochrome c (Clone 7H8.2C12, 1:1000, BD) and anti bactin (Clone AC-15, 1:20,000, Sigma). Secondary antibodies used for western blotting were horseradish peroxidase (HRP)-conjugated sheep antimouse (NXA931, 1:2000, Amersham) goat anti-rabbit (4010-05, 1:5000, Southern Biotech), and goat anti-rat (3010-05, 1:5000, Southern Biotech) IgGs. To avoid non-specific signals from the light chains of IP antibodies, which are very similar in size to Bak, FCY chain specific HRP-conjugated goat anti-mouse IgG (#115-035-008, 1:2000, Jackson ImmunoResearch) was used for IP western blots. RPElabelled goat anti-rat (3050-09, Southern Biotech) or goat anti-mouse (1031-09, Southern Biotech) IgGs were used for FACS.

Bim BH3 peptide (H-DMRPEIWIAQELRRIGDEFNAY-YARR-NH2; SEQ ID NO: 22) was synthesized by Mimotopes, reconstituted (10 mM) in DMSO and kept at −20° C.

Redox catalyst copper(II)(1,10-phenoanthroline)3 (CuPhe) stocks were prepared with 30 mM CuSO4 and 100 mM 1,10-phenoanthroline in 4:1 water:ethanol, and stored at −20° C.

Site-Directed Mutagenesis and Cell Culture

Bak mutants were generated by PCR mutagenesis, verified by sequencing, retrovirally expressed in SV40-transformed Bak−/−Bax−/− mouse embryonic fibroblasts (DKO MEFs), and GFP-positive cells selected and cultured as described previously (Dewson et al., Mol Cell, 30, 369-703, 2008). DU145 cells, obtained from the Frederick National Laboratory (USA) as part of the NCI-60 panel of cell lines (RH Shoemaker, 2006), were maintained in DME supplemented with 10% FBS.

Peptide Scanning Arrays

Three sets of N-terminally biotinylated Bak peptides (with SGSG linker sequence) were synthesized by Mimotopes: (i) 21 15-mer, with a 5-residue overlap, spanning all residues of mouse Bak; (ii) 21 15-mer, with a 5-residue overlap, spanning all residues of human Bak; (iii) 39 8-mer, with a 1 residue offset, spanning residues 20 65 of human Bak.

Each lyophilized peptide (1-3 mg each) was resuspended in 400 ul each 80% dimethylformamide (DMF) and stored at −80° C. 96-well plates (Nunc Immuno Maxisorp, #442404 or Corning Costar nontreated PVC, #2797) were coated with 5 ug/ml streptavidin (Sigma S-4762) by incubation for 16-24 h at 37° C. Plates were washed 4 times with PBS-T (0.1% Tween20 in PBS), blocked by incubating for 1 h at 20° C. in PBS-T containing 0.5% (w/v) BSA (Sigma), and again washed 4 times in PBS-T. Peptides (in DMF) were diluted 1:1000 with H2O, and 100 ul each added to wells of prepared plates. After 1 h incubation, with shaking, unbound peptides were removed by washing 4 times with PBS-T. Primary antibodies were diluted in PBS-T and 100 ul incubated with each peptide for at 1 h at room temperature on a rocking platform. Plates were washed 4 times with PBS-T and 100 ul HRP-conjugated secondary antibody, diluted with PBS-T, was added and plates incubated at room temperature for 1 h on a rocking platform. Dilutions of secondary antibodies were as for western blots, except for peptide set (iii) where the anti-rabbit and anti-rat antibodies were diluted 1:10,000. Plates were washed 4 times with PBS-T and bound secondary antibody was detected by incubating with 100 ul ABTS buffer [1 mM ABTS ((2,2'-Azino-bis(3-ethylbenzthiazoline-6-sulfonic acid)) diammonium salt, Sigma, #A1888), 100 mM citric acid, 0.03% H2O2] for 10-45 min and measuring absorbance at 405 nM using a Hidex Chameleon™ V Multitechnology Platereader.

Bak Tethering and Activation

MEFs were harvested with trypsin, washed with PBS and the outer cell membrane permeabilized by resuspending cells at 1×107 per ml in ice-cold MELB buffer [20 mM HEPES/NaOH pH 7.5, 100 mM sucrose, 2.5 mM MgCl2, 100 mM KCl, 1× Complete protease inhibitor (Roche), 4 ug/ml pepstatin A] containing 0.025% digitonin. After 5 min incubation on ice, cell permeabilization was verified by uptake of trypan blue. For cytochrome c release assays and IPs, permeabilized cells were centrifuged (13000 rpm, 5 min, 4° C.) and membrane fractions resuspended in MELB buffer and kept on ice.

Intra-molecular tethers were induced by disulfide bonding of cysteines using CuPhe diluted 500-fold into the sample. Permeabilized MEFs or membrane fractions were incubated with CuPhe at least 5 min on ice. The efficiency of induction of tethers was assessed by western blotting after mixing aliquots of untreated or CuPhe-treated samples with equal volumes of sample buffer [0.15 M Tris pH 6.8, 30% glycerol, 1.2% SDS, 0.018 mg/ml bromophenol blue) containing 25 mM EDTA to chelate the copper.

To induce Bak activation, untreated or CuPhe-treated samples were incubated with 100 nM caspase-8 cleaved human BID or 10 uM Bim BH3 peptide for 30 min at 30° C., or for 30 min at 44° C. Activation reactions were stopped by placing samples on ice.

Cytochrome c Release

Following activation of Bak in membrane fractions, samples were centrifuged at 13000 rpm, 5 mM, 4° C. The resulting supernatant and pellet fractions were each mixed with sample buffer containing 2-mercaptoethanol and western blotting performed for cytochrome c.

Immunoprecipitation of Activated Bak

Following activation of Bak in membrane fractions, samples were solubilized by incubation with 1% digitonin on ice for at least 30 min. Samples were centrifuged (13000 rpm, 5 min, 4° C.) and supernatants pre-cleared by 30 min incubation at 4° C. with Protein G Sepharose beads (Bundoora), pre-washed with Onyx buffer [20 mM TrisCl pH 7.4, 135 mM NaCl, 1.5 mM MgCl2, 1 mM EGTA, 10% glycerol, 1× Complete protease inhibitor, 4 ug/ml pepstatin A]. After removing beads by repeated washes in Onyx buffer, lysates were incubated with constant agitation for 2 h at 4° C. with 4 ug/ml anti-Bak antibody, followed by incubation for 1 h at 4° C. with additional pre-washed Sepharose G beads. Immune complexes were isolated by centrifugation (13000 rpm, 2 min, 4° C.), washed 4 times with Onyx buffer, resuspended in sample buffer containing 2-mercaptoethanol and analyzed by western blotting.

FACS

Following activation of Bak in permeabilized cells, samples were centrifuged (3000 rpm, 3 min, 4° C.), cells washed with FACS buffer (10% FBS: 90% [1.2 mM MgSO4, 7.4 mM HEPES-NaOH, 0.8 mM K2HPO4, 140 mM NaCl]) and incubated 40 70 mM on ice with anti-Bak antibodies (Ab-1, G317-2 or 4B5) diluted 1:100 in FACS buffer. To assess BH3-domain exposure during Bak activation, 10 ug/ml anti-Bak (4B5) antibody was added to untreated and CuPhe-treated samples immediately prior to the Bak activation step. After incubation with primary antibody, cells were washed with FACS buffer and incubated 40-70 mM on ice with secondary antibody diluted 1:200 in FACS buffer. Cells were washed with FACS buffer and data collected immediately using an LSRII flow cytometer (BD) fitted with FACS Diva software were subsequently analyzed using Weasel (ref).

Western Blotting

Samples were heated 5 min at >95° C., spun briefly and proteins separated by SDS-PAGE using pre-cast 12% TGX gels (BioRad) and transferred to nitrocellulose membranes. Note that transfer of proteins to PVDF rather than nitrocellulose membranes resulted in inferior signals for the majority of Bak antibodies (data not shown). Non-specific binding of antibodies was blocked by incubation for 30-45 min with 5% nonfat milk powder in TBS [20 mM TrisHCl pH7.6, 137 mM NaCl] with 0.1% Tween 20. Membranes were rinsed with TBS/0.1% Tween 20 and incubated with primary antibodies at room temperature for 1-5 h or at 4° C. overnight. The Ab-1, Ab-2 and 4B5 anti-Bak antibodies and anti-cytochrome c antibody were diluted in TBS/0.05% Tween 20, anti-b-actin antibody was diluted in TBS/5% BSA. All other primary antibodies were diluted in blocking solution. Membranes were washed 3 times 5 min in TBS/ 0.1% Tween 20 and incubated 1-2 h at room temperature with secondary antibody diluted in blocking solution, except for cytochrome c blots where the antimouse secondary was also diluted in TBS/0.05% Tween 20. Membranes were washed 3 times 5 min in TBS/0.1% Tween 20, developed with Luminata Forte HRP substrate (Millipore) and bioluminescent signals detected using a ChemiDoc™ XRS+ System fitted with ImageLab™ software (BioRad).

Structural Modeling

The inactive Bak structure (2IMS) was downloaded from PDB and manipulated using MacPyMOL (DeLano Scientific LLC). Images were saved as PNG files.

Isothermal Titration Microcalorimetly (ITC)

ITC experiments were performed using a MicroCal iTC 200 instrument from GE. Injections of 2.43 μl of peptide solution were added from a computer-controlled microsyringe at an interval of 3 min into the sample solution of antibody (cell volume=300 μl) with stirring at 1000 rpm. Titrations were done at pH 7.2 using 20 mm phosphate-buffered saline. The experimental data were fitted to a theoretical titration curve using software supplied by Microcal.

Generation and Purification of 26/05-7D10-17-13 Fab

Papain (Sigma) at 1 mg/ml was solubilised and activated in 10 mM cysteine and 20 mM EDTA in PBS for 10 min on ice followed by 10-fold dilution in PBS. Diluted papain was added to Ab at a ratio of 1 (μg):20 (μg) and incubated at 37° C. To inactivate papain after cleavage is complete, 30 mM iodoacetamide (Sigma) was added. Papain-cleaved Ab was dialysed overnight in Buffer A (10 mM acetic acid, pH 4.5) and applied to a Mono S column equilibrated in Buffer A. A linear 20 ml gradient with Buffer B (10 mM acetic acid, 500 mM NaCl, pH 4.5) was used to separate Fab and Fc in 0.5 ml fractions.

The invention claimed is:

1. A Bak binding antibody or antigen binding fragment thereof having an antigen binding domain, wherein the antigen binding domain binds to or specifically binds to Bak, and wherein, upon binding of the antigen binding domain to Bak changes the conformation of Bak and wherein; the antigen binding domain comprises:
   (i) a heavy chain variable region ($V_H$) comprising a CDR 1 comprising the sequence SEQ ID NO: 1, a CDR2 comprising the sequence SEQ ID NO: 2 and a CDR3 comprising the sequence SEQ ID NO: 3 and a light chain variable region ($V_L$) comprising a CDR 1 comprising the sequence SEQ ID NO: 4, a CDR2 comprising the sequence SEQ ID NO: 5 and a CDR3 comprising the sequence SEQ ID NO: 6;
   (ii) a heavy chain variable region ($V_H$) comprising a CDR 1 comprising the sequence SEQ ID NO: 1, a CDR2 comprising the sequence SEQ ID NO: 2 and a CDR3 comprising the sequence SEQ ID NO: 3 and a light chain variable region ($V_L$) comprising a CDR 1 comprising the sequence SEQ ID NO: 4, a CDR2 comprising the sequence SEQ ID NO: 5 and a CDR3 comprising the sequence SEQ ID NO: 6, wherein the $V_H$ comprises a sequence at least 90%, at least 95%, or at least 99% identical to the sequence set forth in SEQ ID NO: 7; or
   (iii) a heavy chain variable region ($V_H$) comprising a CDR 1 comprising the sequence SEQ ID NO: 1, a CDR2 comprising the sequence SEQ ID NO: 2 and a CDR3 comprising the sequence SEQ ID NO: 3 and a light chain variable region ($V_L$) comprising a CDR 1 comprising the sequence SEQ ID NO: 4, a CDR2 comprising the sequence SEQ ID NO: 5 and a CDR3 comprising the sequence SEQ ID NO: 6, wherein the $V_L$ comprises a sequence at least 90%, at least 95%, or at least 99% identical to the sequence set forth in SEQ ID NO: 8.

2. The Bak binding antibody or fragment thereof of claim 1, wherein the antigen binding domain comprises:
   (i) a heavy chain variable region ($V_H$) comprising a CDR 1 comprising a sequence identical to SEQ ID NO: 1, a CDR2 comprising a sequence identical to SEQ ID NO: 2 and a CDR3 comprising a sequence identical to SEQ ID NO: 3; and
   (ii) a light chain variable region ($V_L$) comprising a CDR 1 comprising a sequence identical to SEQ ID NO: 4, a CDR2 comprising a sequence identical to SEQ ID NO: 5 and a CDR3 comprising a sequence identical to SEQ ID NO: 6.

3. An in-vitro method of activating Bak in a cell, the method comprising:
   i) contacting a cell with the antibody of claim 2; and
   ii) optionally, detecting activation of Bak.

4. An in-vitro method of inducing apoptosis in a cell the method comprising contacting a cell with the antibody of claim 2 and, optionally detecting if apoptosis is induced.

5. The antibody or fragment thereof of claim 2 which is conjugated to an agent or compound.

6. A composition comprising the antibody or fragment thereof of claim 2 and a pharmaceutically acceptable carrier.

7. The Bak binding antibody or fragment thereof of claim 1, wherein the antigen binding domain comprises:
   (i) a $V_H$ comprising a sequence set forth in SEQ ID NO: 7;
   (ii) a $V_L$ comprising a sequence set forth in SEQ ID NO: 8; or
   (iii) a $V_H$ comprising a sequence set forth in SEQ ID NO: 7 and a $V_L$ comprising a sequence set forth in SEQ ID NO: 8.

8. The antibody or fragment thereof of claim 7 which is conjugated to an agent or compound.

9. A composition comprising the antibody or fragment thereof of claim 7 and a pharmaceutically acceptable carrier.

10. An in-vitro method of activating Bak in a cell, the method comprising:
    i) contacting a cell with the Bak binding antibody or fragment thereof of claim 1; and
    ii) optionally, detecting activation of Bak.

11. An in-vitro method of inducing apoptosis in a cell the method comprising contacting a cell with the Bak binding antibody or fragment thereof of claim 1 and, optionally detecting if apoptosis is induced.

12. The antibody or fragment thereof of claim 1 which is conjugated to an agent or compound.

13. The antibody or fragment thereof of claim 12, wherein the agent or compound is selected from the group consisting of a radioisotope, a detectable label, a therapeutic compound, a colloid, a toxin, a nucleic acid, a peptide, a protein, an agent that increases the half-life of the antibody or fragment in a subject, or an internalizing moiety.

14. The antibody or fragment thereof of claim 12, wherein the agent or compound is selected from a cell penetrating peptide or another antibody.

15. The antibody or fragment thereof of claim 14, wherein the another antibody is cell penetrating antibody 3E10.

16. A composition comprising the antibody of claim 1 and a pharmaceutically acceptable carrier.

17. The Bak binding antibody or fragment thereof of claim 1, wherein the antibody or fragment is a:
    (i) a single chain Fv fragment (scFv);
    (ii) a dimeric scFv (di-scFv);
    (iii) one of (i) or (ii) linked to a constant region of an antibody, Fc or a heavy chain constant domain ($C_H$) 2 and/or $C_H$3; or
    if the $V_H$ and $V_L$ are in separate polypeptide chains the antibody or fragment is:
    (i) a diabody;
    (ii) a triabody;
    (iii) a tetrabody;
    (iv) a Fab;
    (v) a F(ab')2;
    (vi) a Fv; or
    (vii) one of (i) to (vi) linked to a constant region of an antibody, Fc or a heavy chain constant domain ($C_H$) 2 and/or $C_H$3.

18. The Bak binding antibody or fragment thereof of claim 1, wherein the antibody or fragment is chimeric, humanized, synhumanized or primatized.

* * * * *